US009855349B2

(12) United States Patent
Konstantopoulos et al.

(10) Patent No.: US 9,855,349 B2
(45) Date of Patent: Jan. 2, 2018

(54) SELECTIN LIGANDS USEFUL IN THE DIAGNOSIS AND TREATMENT OF CANCER

(71) Applicants: Konstantinos Konstantopoulos, Ellicott City, MD (US); Susan Napier Thomas, Baltimore, MD (US)

(72) Inventors: Konstantinos Konstantopoulos, Ellicott City, MD (US); Susan Napier Thomas, Baltimore, MD (US)

(73) Assignees: Konstantinos Konstantopoulos, Ellicott City, MD (US); Susan Napier Thomas, Baltimore, MD (US)

(*) Notice: Subject to any disclaimer, the term of this patent is extended or adjusted under 35 U.S.C. 154(b) by 0 days.

(21) Appl. No.: 14/868,626

(22) Filed: Sep. 29, 2015

(65) Prior Publication Data

US 2016/0151519 A1    Jun. 2, 2016

Related U.S. Application Data

(63) Continuation of application No. 12/919,902, filed as application No. PCT/US2009/035724 on Mar. 2, 2009.

(Continued)

(51) Int. Cl.
*C07K 16/18* (2006.01)
*B82Y 5/00* (2011.01)
(Continued)

(52) U.S. Cl.
CPC ...... *A61K 51/1063* (2013.01); *A61K 39/3955* (2013.01); *A61K 39/39558* (2013.01);
(Continued)

(58) Field of Classification Search
CPC .......... C07K 16/28; C07K 16/2884; C07K 16/3007; C07K 16/18; C07K 16/2896; C07K 16/3046; G01N 33/5091; G01N 33/534; G01N 33/566; G01N 33/574; G01N 33/57473; G01N 33/57484;
(Continued)

(56) References Cited

U.S. PATENT DOCUMENTS 5,057,313 A * 10/1991 Shih ................. A61K 47/48692
                                                 424/1.53
5,843,708 A * 12/1998 Hardman ........... C07K 16/3007
                                                 435/69.1
(Continued)

FOREIGN PATENT DOCUMENTS

WO          99/41363      *  8/1999

OTHER PUBLICATIONS

Belov et al., 2001. Immunophenotyping of leukemias using a cluster of differentiation antibody microarray. Cancer Res. 61: 4483-4489.*
(Continued)

*Primary Examiner* — Gail R Gabel
(74) *Attorney, Agent, or Firm* — IP & T Group LLP

(57) ABSTRACT

The present invention provides methods and compositions useful in the diagnosis and treatment of cancer. More specifically, the present invention provides compositions and methods of use comprising a targeting composition comprising a solid substrate, an antibody composition, and optionally a chemotherapeutic agent.

8 Claims, 19 Drawing Sheets

Related U.S. Application Data

(60) Provisional application No. 61/072,945, filed on Apr. 3, 2008, provisional application No. 61/067,438, filed on Feb. 28, 2008.

(51) Int. Cl.
| | | |
|---|---|---|
| *A61K 51/10* | (2006.01) | |
| *A61K 39/395* | (2006.01) | |
| *A61K 47/48* | (2006.01) | |
| *C07K 16/28* | (2006.01) | |
| *C07K 16/30* | (2006.01) | |

(52) U.S. Cl.
CPC .. *A61K 47/48561* (2013.01); *A61K 47/48576* (2013.01); *A61K 47/48876* (2013.01); *A61K 51/1027* (2013.01); *A61K 51/1048* (2013.01); *A61K 51/1093* (2013.01); *B82Y 5/00* (2013.01); *C07K 16/18* (2013.01); *C07K 16/2896* (2013.01); *C07K 16/3046* (2013.01)

(58) Field of Classification Search
CPC ............. G01N 33/57492; G01N 33/60; G01N 2033/574; G01N 2033/57403; G01N 2333/705; G01N 2333/70585; G01N 2800/7028; A61K 39/395; A61K 39/39558; A61K 39/44; A61K 49/0058; A61K 49/0067; A61K 49/0428; A61K 49/16; A61K 51/02; A61K 51/10; A61K 51/1027; A61K 51/1045; A61K 51/1048; A61K 2039/505; A61K 2123/00; A61K 39/3955; A61K 47/48561; A61K 47/48576; A61K 47/48876; A61K 51/1093; A61K 51/1063; B85Y 5/00
USPC ....... 424/1.49, 9.3, 9.323, 9.34, 9.341, 9.41, 424/9.6, 143.1, 155.1, 156.1, 173.1, 424/174.1, 178.1; 435/7.21, 7.23, 975; 436/501, 504, 64, 813; 530/388.22, 530/388.7, 388.8, 388.85, 389.6, 389.7, 530/391.1, 391.3, 866
See application file for complete search history.

(56) References Cited

U.S. PATENT DOCUMENTS

| | | | | |
|---|---|---|---|---|
| 6,380,371 | B1* | 4/2002 | Sassetti | C07K 16/28 530/350 |
| 7,560,226 | B2* | 7/2009 | Christopherson | G01N 33/574 435/4 |
| 8,173,374 | B2* | 5/2012 | Choo | A61K 35/545 435/7.1 |
| 2002/0172987 | A1* | 11/2002 | Terstappen | B03C 1/01 435/7.23 |
| 2004/0038406 | A1* | 2/2004 | Unger | A61K 9/0019 435/459 |
| 2004/0180387 | A1* | 9/2004 | O'Shannessy | G01N 33/57449 435/7.23 |
| 2006/0003391 | A1* | 1/2006 | Ring | G01N 33/57415 435/7.23 |

OTHER PUBLICATIONS

Hanley et al., Dec. 13, 2005. Variant isoforms of CD44 are P- and L-selectin ligands on colon carcinoma cells. FASEB J. 20: 337-339, and downloaded full text pp. 1-22.*

Hanley et al., 2005. CD44 on LS174T colon carcinoma cells possesses E-selectin ligand activity. Cancer Res. 65: 5812-5817.*

Kuespert et al., 2006. CEACAMs: their role in physiology and pathophysiology. Curr. Opinion Cell Biol. 18: 565-571.*

Napier et al., 2007. Selectin ligand expression regulates the initial vascular interactions of colon carcinoma cells. J. Biol. Chem. 282: 3433-3441.*

Somasiri et al., 2004. Overexpression of the anti-adhesin podocalyxin is an independent predictor of breat cancer progression. Cancer Res. 64: 5068-5073.*

Wang et al., 2007. Selection of DNA aptamer that specific binding human carcinoembryonic antigen in vitro. J. Nanjing Med. Univ. 21: 277-281.*

Suzuki et al. Differential Expression of CD44 variants among meningioma subtypes. J Clin Pathol: Mol Pathol 49: M140-M146 (1996).*

\* cited by examiner

```
                         SEQUENCE LISTING

<160> NUMBER OF SEQ ID NOS: 5

<210> SEQ ID NO 1
<211> LENGTH: 6007
<212> TYPE: DNA
<213> ORGANISM: Homo sapiens

<400> SEQUENCE: 1
agccgcgcag acgccgccca ggacgcagcc gccgccgccg ccgctcctct gccactggct      60
ctgcgcccca gcccggctct gctgcagcgg cagggaggaa gagccgccgc agcgcgactc     120
gggagccccg ggccacagcc tggcctccgg agccacccac aggcctcccc gggcggcgcc     180
cacgctccta ccgcccggac gcgcggatcc tccgccggca ccgcagccac ctgctcccgg     240
cccagaggcg acgacacgat gcgctgcgcg ctggcgctct cggcgctgct gctactgttg     300
tcaacgccgc cgctgctgcc gtcgtcgccg tcgccgtcgc cgtcgccctc ccagaatgca     360
acccagacta ctacggactc atctaacaaa acagcaccga ctccagcatc cagtgtcacc     420
atcatggcta cagatacagc ccagcagagc acagtcccca cttccaaggc caacgaaatc     480
ttggcctcgg tcaaggcgac cacccttggt gtatccagtg actcaccggg gactacaacc     540
ctggctcagc aagtctcagg cccagtcaac actaccgtgg ctagaggagg cggctcaggc     600
aaccctacta ccaccatcga gagccccaag agcacaaaaa gtgcagacac cactacagtt     660
gcaacctcca cagccacagc taaacctaac accacaagca gccagaatgg agcagaagat     720
acaacaaact ctgggggggaa aagcagccac agtgtgacca cagacctcac atccactaag     780
gcagaacatc tgacgacccc tcaccctaca agtccactta gccccgaca acccacttcg     840 acgcatcctg tggccacccc aacaagctcg ggacatgacc atcttatgaa aatttcaagc     900
agttcaagca ctgtggctat ccctggctac accttcacaa gcccggggat gaccaccacc     960
ctactagaga cagtgtttca ccatgtcagc caggctggtc ttgaactcct gacctcgggt    1020
gatctgccca ccttggcctc ccaaagtgct gggattacag cgtcatcggt tatctcgcaa    1080
agaactcaac agacctccag tcagatgcca gccagctcta cggccccttc ctcccaggag    1140
acagtgcagc ccacgagccc ggcaacggca ttgagaacac ctaccctgcc agagaccatg    1200
agctccagcc ccacagcagc atcaactacc caccgatacc ccaaaacacc ttctcccact    1260
gtggctcatg agagtaactg ggcaaagtgt gaggatcttg agacacagac acagagtgag    1320
aagcagctcg tcctgaacct cacaggaaac accctctgtg caggggcgc ttcggatgag    1380
```

```
aaattgatct cactgatatg ccgagcagtc aaagccacct tcaacccggc ccaagataag    1440
tgcggcatac ggctggcatc tgttccagga agtcagaccg tggtcgtcaa agaaatcact    1500
attcacacta agctccctgc caaggatgtg tacgagcggc tgaaggacaa atgggatgaa    1560
ctaaaggagg caggggtcag tgacatgaag ctaggggacc aggggccacc ggaggaggcc    1620
gaggaccgct tcagcatgcc cctcatcatc accatcgtct gcatggcatc attcctgctc    1680
ctcgtggcgg ccctctatgg ctgctgccac cagcgcctct cccagaggaa ggaccagcag    1740
cggctaacag aggagctgca gacagtggag aatggttacc atgacaaccc aacactggaa    1800
gtgatggaga cctcttctga gatgcaggag aagaaggtgg tcagcctcaa cggggagctg    1860
ggggacagct ggatcgtccc tctggacaac ctgaccaagg acgacctgga tgaggaggaa    1920
gacacacacc tctagtccgg tctgccggtg gcctccagca gcaccacaga gctccagacc    1980
aaccacccca gtgccgtttt ggatggggaa gggaaagact ggggagggag agtgaactcc    2040
gaggggtgtc ccctcccaat cccccccaggg ccttaatttt tccctttttca acctgaacaa    2100 atcacattct gtccagattc ctcttgtaaa ataacccact agtgcctgag ctcagtgctg    2160
ctggatgatg agggagatca agaaaaagcc acgtaaggga ctttatagat gaactagtgg    2220
aatcccttca ttctgcagtg agattgccga gacctgaaga gggtaagtga cttgcccaag    2280
gtcagagcca cttggtgaca gagccaggat gagaacaaag attccatttg caccatgcca    2340
cactgctgtg ttcacatgtg ccttccgtcc agagcagtcc cggggcagggg tgaaactcca    2400 gcaggtggct gggctggaaa ggagggcagg gctacatcct ggctcggtgg gatctgacga    2460
cctgaaagtc cagctcccaa gttttccttc tcctacccca gcctcgtgta cccatcttcc    2520
caccctctat gttcttaccc ctccctacac tcagtgtttg ttcccactta ctctgtcctg    2580
gggcctctgg gattagcaca ggttattcat aaccttgaac cccttgttct ggattcggat    2640
tttctcacat ttgcttcgtg agatgggggc ttaacccaca caggtctccg tgcgtgaacc    2700
aggtctgctt aggggacctg cgtgcaggtg aggagagaag gggacactcg agtccaggct    2760
ggtatctcag ggcagctgat gaggggtcag caggaacact ggcccattgc ccctggcact    2820
ccttgcagag gccacccacg atcttctttg ggcttccatt tccaccaggg actaaaatct    2880
gctgtagcta gtgagagcag cgtgttcctt ttgttgttca ctgctcagct gatgggagtg    2940
attccctgag acccagtatg aaagagcagt ggctgcagga gaggccttcc cggggccccc    3000
catcagcgat gtgtcttcag agacaatcca ttaaagcagc caggaaggac aggctttccc    3060
ctgtatatca taggaaactc agggacattt caagttgctg agagttttgt tatagttgtt    3120
ttctaaccca gccctccact gccaaaggcc aaaagctcag acagttggca gacgtccagt    3180
tagctcatct cactcactct gattctcctg tgccacagga aaagagggcc tggaaagcgc    3240
agtgcatgct gggtgcatga agggcagcct gggggacaga ctgttgtggg aacgtccac    3300 tgtcctggcc tggagctagg ccttgctgtt cctcttctct gtgagcctag tggggctgct    3360
gcggttctct tgcagtttct ggtggcatct caggggaaca caaagctatg tctattcccc    3420
aatataggac ttttatgggc tcggcagtta gctgccatgt agaaggctcc taagcagtgg    3480
gcatggtgag gtttcatctg attgagaagg gggaatcctg tgtggaatgt tgaactttcg    3540
ccatggtctc catcgttctg ggcgtaaatt ccctgggatc aagtaggaaa atgggcagaa    3600
ctgcttaggg gaatgaaatt gccatttttc gggtgaaacg ccacacctcc agggtcttaa    3660
gagtcaggct ccggctgtag tagctctgat gaaataggct atcccactcgg gatggcttac    3720 tttttaaaag ggtaggggga ggggctgggg aagatctgtc ctgcaccatc tgcctaattc    3780
```

```
cttcctcaca gtctgtagcc atctgatatc ctaggggaaa aggaaggcca ggggttcaca    3840
tagggcccca gcgagtttcc caggagttag agggatgcga ggctaacaag ttccaaaaac    3900
atctgccccg atgctctagt gtttggaggt gggcaggatg agaacagtg cctgtttggg     3960 ggaaaacagg aaatcttgtt aggcttgagt gaggtgtttg cttccttctt gcccagcgct    4020
gggttctctc cacccagtag gttttctgtt gtggtcccgt gggagaggcc agactggatt    4080
attcctcctt tgctgatcct gggtcacact tcaccagcca gggcttttga cggagacagc    4140
aaataggcct ctgcaaatca atcaaaggct gcaaccctat ggcctcttgg agacagatga    4200
tgactggcaa ggactagaga gcaggagtgc ctggccaggt cggtcctgac tctcctgact    4260
ctccatcgct ctgtccaagg agaacccgga gaggctctgg gctgattcag aggttactgc    4320
tttatattcg tccaaactgt gttagtctag gcttaggaca gcttcagaat ctgcacsctt    4380
gccttgctct tgccaccagg acacctatgt caacaggcca acagccatg catctataaa     4440 ggtcatcatc ttctgccacc tttactgggt tctaaatgct ctctgataat tcagagagca    4500
ttgggtctgg gaagaggtaa gaggaacact agaagctcag catgacttaa acaggttgta    4560
gcaaagacag tttatcatca gctctttcag tggtaaactg tggttttccc aagctgcaca    4620
ggaggccaga aaccacaagt atgatgacta ggaagcctac tgtcatgaga gtggggagac    4680
aggcagcaaa gcttatgaag gaggtacaga atattctttg cgttgtaaga cagaatacgg    4740
gtttaatcta gtctaggcac cagattttttt tcccgcttga taaggaaagc tagcagaaag    4800
tttatttaaa ccacttcttg agctttatct tttttgacaa tatactggag aaactttgaa    4860
gaacaagttc aaactgatac atatacacat atttttttga taatgtaaat acagtgacca    4920
tgttaaccta ccctgcactg ctttaagtga acatactttg aaaaagcatt atgttagctg    4980
agtgatggcc aagttttttc tctggacagg aatgtaaatg tcttactgga aatgacaagt    5040
ttttgcttga tttttttttt taaacaaaaa atgaaatata acaagacaaa cttatgataa    5100
agtatttgtc ttgtagatca ggtgtttgt tttgttttt taattttaaa atgcaaccct      5160 gcccctccc cagcaaagtc acagctccat ttcagtaaag gttggagtca atatgctctg     5220
gttggcaggc aaccctgtag tcatggagaa aggtatttca agatctagtc caatcttttt    5280
ctagagaaaa agataatctg aagctcacaa agatgaagtg acttcctcaa atcacatgg     5340 ttcaggacag aaacaagatt aaaacctgga tccacagact gtgcgcctca gaaggaataa    5400
tcggtaaatt aagaattgct actcgaaggt gccagaatga cacaaaggac agaattcctt    5460
tcccagttgt taccctagca aggctaggga gggcatgaac acaaacataa gaactggtct    5520
tctacacttt ctctgaatca tttaggtta agatgtaagt gaacaattct ttctttctgc     5580
caagaaacaa agttttggat gagctttat atatggaact tactccaaca ggactgaggg     5640
accaaggaaa catgatgggg gaggcagaga gggcaagagt aaaactgtag catagctttt    5700
gtcacggtca ctagctgatc cctcaggtct gctgcaaaca cagcatggag gacacagatg    5760
actctttggt gttggtcttt ttgtctgcag tgaatgttca acagtttgcc caggaactgg    5820
gggatcatat atgtcttagt ggacaggggc tgaagtaca ctggaattta ctgagaaact     5880
tgtttgtaaa aactatagtt aataattatt gcatttttctt acaaaatat atttttggaaa   5940 attgtatact gtcaattaaa gtgttttttgt gtaaactggt tcaaaaaaaa aaaaaaaaa    6000 aaaaaaa                                                              6007
```

<210> SEQ ID NO 2

<211> LENGTH: 5911
<212> TYPE: DNA
<213> ORGANISM: Homo sapiens

<400> SEQUENCE: 2

```
agccgcgcag acgccgccca ggacgcagcc gccgccgccg ccgctcctct gccactggct      60
ctgcgcccca gcccggctct gctgcagcgg cagggaggaa gagccgccgc agcgcgactc     120
gggagcccg ggccacagcc tggcctccgg agccacccac aggcctcccc gggcggcgcc      180
cacgctccta ccgcccggac gcgcggatcc tccgccggca ccgcagccac ctgctcccgg     240
cccagaggcg acgacacgat gcgctgcgcg ctggcgctct cggcgctgct gctactgttg     300
tcaacgccgc cgctgctgcc gtcgtcgccg tcgccgtcgc cgtcgccctc ccagaatgca     360
acccagacta ctacggactc atctaacaaa acagcaccga ctccagcatc cagtgtcacc     420
atcatggcta cagatacagc ccagcagagc acagtcccca cttccaaggc caacgaaatc     480
ttggcctcgg tcaaggcgac cacccttggt gtatccagtg actcaccggg gactacaacc     540
ctggctcagc aagtctcagg cccagtcaac actaccgtgg ctagaggagg cggctcaggc     600
aaccctacta ccaccatcga gagccccaag agcacaaaaa gtgcagacac cactacagtt     660
gcaacctcca cagccacagc taaacctaac accacaagca gccagaatgg agcagaagat     720
acaacaaact ctgggggaa aagcagccac agtgtgacca cagacctcac atccactaag     780
gcagaacatc tgacgacccc tcaccctaca agtccactta gccccgaca cccacttcg      840
acgcatcctg tggccacccc aacaagctcg ggacatgacc atcttatgaa aatttcaagc     900
agttcaagca ctgtggctat ccctggctac accttcacaa gcccggggat gaccaccacc     960
ctaccgtcat cggttatctc gcaaagaact caacagacct ccagtcagat gccagccagc    1020
tctacggccc cttcctccca ggagacagtg cagcccacga gccggcaac ggcattgaga     1080
acacctaccc tgccagagac catgagctcc agcccacag cagcatcaac tacccaccga    1140
taccccaaaa caccttctcc cactgtggct catgagagta actgggcaaa gtgtgaggat    1200
cttgagacac agacacagag tgagaagcag ctcgtcctga acctcacagg aaacaccctc    1260
tgtgcagggg gcgcttcgga tgagaaattg atctcactga tatgccgagc agtcaaagcc    1320
accttcaacc cggcccaaga taagtgcggc atacggctgg catctgttcc aggaagtcag    1380
accgtggtcg tcaaagaaat cactattcac actaagctcc ctgccaagga tgtgtacgag    1440
cggctgaagg acaaatggga tgaactaaag gaggcagggg tcagtgacat gaagctaggg    1500
gaccaggggc caccggagga ggccgaggac cgcttcagca tgcccctcat catcaccatc    1560
gtctgcatgg catcattcct gctcctcgtg gcggccctct atggctgctg ccaccagcgc    1620
ctctcccaga ggaaggacca gcagcggcta acagaggagc tgcagacagt ggagaatggt    1680
taccatgaca acccaacact ggaagtgatg gagacctctt ctgagatgca ggagaagaag    1740
gtggtcagcc tcaacgggga gctggggac agctggatcg tccctctgga caacctgacc    1800
aaggacgacc tggatgagga ggaagacaca cacctctagt ccggtctgcc ggtggcctcc    1860
agcagcacca cagagctcca gaccaaccac cccaagtgcc gtttggatgg ggaagggaaa    1920
gactggggag ggagagtgaa ctccgagggg tgtcccctcc caatcccccc agggccttaa    1980
tttttccctt ttcaacctga acaaatcaca ttctgtccag attcctcttg taaaataacc    2040
cactagtgcc tgagctcagt gctgctggat gatgagggag atcaagaaaa agccacgtaa    2100
gggactttat agatgaacta gtggaatccc ttcattctgc agtgagattg ccagacctg     2160
aagagggtaa gtgacttgcc caaggtcaga gcccacttggt gacagagcca ggatgagaac    2220
```

```
aaagattcca tttgcaccat gccacactgc tgtgttcaca tgtgccttcc gtccagagca    2280
gtcccgggca ggggtgaaac tccagcaggt ggctgggctg gaaaggaggg cagggctaca    2340
tcctggctcg gtgggatctg acgacctgaa agtccagctc ccaagttttc cttctcctac    2400
cccagcctcg tgtacccatc ttcccaccct ctatgttctt acccctccct acactcagtg    2460
tttgttccca cttactctgt cctggggcct ctgggattag cacaggttat tcataacctt    2520
gaaccccttg ttctggattc ggattttctc acatttgctt cgtgagatgg gggcttaacc    2580
cacacaggtc tccgtgcgtg aaccaggtct gcttagggga cctgcgtgca ggtgaggaga    2640
gaaggggaca ctcgagtcca ggctggtatc tcagggcagc tgatgagggg tcagcaggaa    2700
cactggccca ttgcccctgg cactccttgc agaggccacc cacgatcttc tttgggcttc    2760
catttccacc agggactaaa atctgctgta gctagtgaga gcagcgtgtt cctttttgttg   2820 ttcactgctc agctgatggg agtgattccc tgagacccag tatgaaagag cagtggctgc    2880
aggagaggcc ttcccggggc cccccatcag cgatgtgtct tcagagacaa tccattaaag    2940
cagccaggaa ggacaggctt tcccctgtat atcataggaa actcagggac atttcaagtt    3000
gctgagagtt ttgttatagt tgttttctaa cccagccctc cactgccaaa ggccaaaagc    3060
tcagacagtt ggcagacgtc cagttagctc atctcactca ctctgattct cctgtgccac    3120
aggaaaagag ggcctggaaa gcgcagtgca tgctgggtgc atgaagggca gcctggggga    3180
cagactgttg tgggaacgtc ccactgtcct ggcctggagc taggccttgc tgttcctctt    3240
ctctgtgagc ctagtggggc tgctgcggtt ctcttgcagt ttctggtggc atctcagggg    3300
aacacaaagc tatgtctatt ccccaatata ggactttat gggctcggca gttagctgcc     3360
atgtagaagg ctcctaagca gtgggcatgg tgaggtttca tctgattgag aaggggggaat   3420 cctgtgtgga atgttgaact ttcgccatgg tctccatcgt tctgggcgta aattccctgg    3480
gatcaagtag gaaaatgggc agaactgctt aggggaatga aattgccatt tttcgggtga    3540
aacgccacac ctccagggtc ttaagagtca ggctccggct gtagtagctc tgatgaaata    3600
ggctatccac tcgggatggc ttactttta aaagggtagg gggaggggct ggggaagatc     3660
tgtcctgcac catctgccta attccttcct cacagtctgt agccatctga tatcctaggg    3720
gaaaaggaag gccaggggtt cacatagggc cccagcgagt ttcccaggag ttagagggat    3780
gcgaggctaa caagttccaa aaacatctgc cccgatgctc tagtgtttgg aggtgggcag    3840
gatggagaac agtgcctgtt tgggggaaaa caggaaatct tgttaggctt gagtgaggtg    3900
tttgcttcct tcttgcccag cgctgggttc tctccaccca gtaggttttc tgttgtggtc    3960
ccgtgggaga ggccagactg gattattcct cctttgctga tcctgggtca cacttcacca   4020
gccagggctt ttgacggaga cagcaaatag gcctctgcaa atcaatcaaa ggctgcaacc   4080
ctatggcctc ttggagacag atgatgactg gcaaggacta gagagcagga gtgcctggcc   4140
aggtcggtcc tgactctcct gactctccat cgctctgtcc aaggagaacc cggagaggct   4200
ctgggctgat tcagaggtta ctgctttata ttcgtccaaa ctgtgttagt ctaggcttag   4260
gacagcttca gaatctgaca ccttgccttg ctcttgccac caggacacct atgtcaacag   4320
gccaaacagc catgcatcta taaggtcat catcttctgc cacctttact gggttctaaa    4380
tgctctctga taattcagag agcattgggt ctgggaagag gtaagaggaa cactagaagc   4440
tcagcatgac ttaaacaggt tgtagcaaag acagtttatc atcagctctt tcagtggtaa   4500
actgtggttt ccccaagctg cacaggaggc cagaaaccac aagtatgatg actaggaagc   4560
```

```
ctactgtcat gagagtgggg agacaggcag caaagcttat gaaggaggta cagaatattc    4620
tttgcgttgt aagacagaat acgggtttaa tctagtctag gcaccagatt tttttcccgc    4680
ttgataagga aagctagcag aaagtttatt taaaccactt cttgagcttt atctttttg     4740 acaatatact ggagaaactt tgaagaacaa gttcaaactg atacatatac acatatttt     4800 ttgataatgt aaatacagtg accatgttaa cctaccctgc actgctttaa gtgaacatac    4860
tttgaaaaag cattatgtta gctgagtgat ggccaagttt tttctctgga caggaatgta    4920
aatgtcttac tggaaatgac aagttttgc ttgattttt tttttaaaca aaaatgaaa       4980 tataacaaga caaacttatg ataaagtatt tgtcttgtag atcaggtgtt ttgttttgtt    5040
tttttaattt taaaatgcaa ccctgccccc tccccagcaa agtcacagct ccatttcagt    5100
aaaggttgga gtcaatatgc tctggttggc aggcaaccct gtagtcatgg agaaaggtat    5160
ttcaagatct agtccaatct ttttctagag aaaaagataa tctgaagctc acaaagatga    5220
agtgacttcc tcaaaatcac atggttcagg acagaaacaa gattaaaacc tggatccaca    5280
gactgtgcgc ctcagaagga ataatcggta aattaagaat tgctactcga aggtgccaga    5340
atgacacaaa ggacagaatt ccttttccag ttgttaccct agcaaggcta gggagggcat    5400
gaacacaaac ataagaactg gtcttctaca ctttctctga atcatttagg tttaagatgt    5460
aagtgaacaa ttctttcttt ctgccaagaa acaaagtttt ggatgagctt ttatatatgg    5520
aacttactcc aacaggactg agggaccaag gaaacatgat gggggaggca gagagggcaa    5580
gagtaaaact gtagcatagc ttttgtcacg gtcactagct gatccctcag gtctgctgca    5640
aacacagcat ggaggacaca gatgactctt tggtgttggt cttttttgtct gcagtgaatg    5700 ttcaacagtt tgcccaggaa ctgggggatc atatatgtct tagtggacag gggtctgaag    5760
tacactggaa tttactgaga aacttgtttg taaaaactat agttaataat tattgcattt    5820
tcttacaaaa atatattttg gaaaattgta tactgtcaat taaagtgttt tgtgtaaac     5880 tggttcaaaa aaaaaaaaa aaaaaaaaa a                                     5911
```

<210> SEQ ID NO 3
<211> LENGTH: 3600
<212> TYPE: DNA
<213> ORGANISM: Homo sapiens

<400> SEQUENCE: 3

```
gaagagactc agggcagagg gaggaaggac agcagaccag acagtcacag cagccttgac      60
aaaacgttcc tggaactcaa gctcttctcc acagaggagg acagagcaga cagcagagac     120
catggagtct ccctcggccc ctccccacag atggtgcatc ccctggcaga ggctcctgct     180
cacagcctca cttctaacct tctggaaccc gcccaccact gccaagctca ctattgaatc     240
cacgccgttc aatgtcgcag aggggaagga ggtgcttcta cttgtccaca atctgcccca    300
gcatcttttt ggctacagct ggtacaaagg tgaaagagtg gatggcaacc gtcaaattat    360
aggatatgta ataggaactc aacaagctac cccagggccc gcatacagtg gtcgagagat    420 aatataccccc aatgcatccc tgctgatcca gaacatcatc cagaatgaca caggattcta    480
cacccctaca cgtcataaagt cagatcttgt gaatgaagaa gcaactggcc agttccgggt    540 ataccccggag ctgcccaagc cctccatctc cagcaacaac tccaaacccg tggaggacaa    600
ggatgctgtg gccttcacct gtgaacctga gactcaggac gcaacctacc gtgggtgggt    660
aaacaatcag agcctcccgg tcagtcccag gctgcagctg tccaatggca acaggaccct    720
cactctattc aatgtcacaa gaaatgacac agcaagctac aaatgtgaaa cccagaaccc    780
```

```
agtgagtgcc aggcgcagtg attcagtcat cctgaatgtc ctctatggcc cggatgcccc     840
caccatttcc cctctaaaca catcttacag atcaggggaa aatctgaacc tctcctgcca     900
cgcagcctct aacccacctg cacagtactc ttggtttgtc aatgggactt ccagcaatc     960 cacccaagag ctctttatcc ccaacatcac tgtgaataat agtggatcct atacgtgcca    1020
agcccataac tcagacactg gcctcaatag gaccacagtc acgacgatca cagtctatgc    1080
agagccaccc aaacccttca tcaccagcaa caactccaac cccgtggagg atgaggatgc    1140
tgtagcctta acctgtgaac ctgagattca gaacacaacc tacctgtggt gggtaaataa    1200
tcagagcctc ccggtcagtc ccaggctgca gctgtccaat gacaacagga ccctcactct    1260
actcagtgtc acaaggaatg atgtaggacc ctatgagtgt ggaatccaga acaaattaag    1320
tgttgaccac agcgacccag tcatcctgaa tgtcctctat ggcccagacg accccaccat    1380 ttcccctca tacacctatt accgtccagg ggtgaacctc agcctctcct gccatgcagc    1440
ctctaaccca cctgcacagt attcttggct gattgatggg aacatccagc aacacacaca    1500
agagctcttt atctccaaca tcactgagaa gaacagcgga ctctataccct gccaggccaa    1560 taactcagcc agtggccaca gcaggactac agtcaagaca atcacagtct ctgcggagct    1620
gcccaagccc tccatctcca gcaacaactc caaacccgtg gaggacaagg atgctgtggc    1680
cttcacctgt gaacctgagg ctcagaacac aacctacctg tggtgggtaa atggtcagag    1740
cctcccagtc agtcccaggc tgcagctgtc caatggcaac aggaccctca ctctattcaa    1800
tgtcacaaga aatgacgcaa gagcctatgt atgtggaatc cagaactcag tgagtgcaaa    1860
ccgcagtgac ccagtcaccc tggatgtcct ctatgggccg gacacccca tcatttcccc    1920 cccagactcg tcttaccttt cgggagcgaa cctcaacctc tcctgccact cggcctctaa    1980
cccatccccg cagtattctt ggcgtatcaa tgggataccg cagcaacaca cacaagttct    2040
ctttatcgcc aaaatcacgc caaataataa cgggacctat gcctgttttg tctctaactt    2100
ggctactggc cgcaataatt ccatagtcaa gagcatcaca gtctctgcat ctggaacttc    2160
tcctggtctc tcagctgggg ccactgtcgg catcatgatt ggagtgctgg ttggggttgc    2220
tctgatatag cagccctggt gtagtttctt catttcagga agactgacag ttgttttgct    2280
tcttccttaa agcatttgca acagctacag tctaaaattg cttctttacc aaggatattt    2340
acagaaaaga ctctgaccag agatcgagac catcctagcc aacatcgtga aaccccatct    2400
ctactaaaaa tacaaaaatg agctgggctt ggtggcgcgc acctgtagtc ccagttactc    2460
gggaggctga ggcaggagaa tcgcttgaac ccgggaggtg gagattgcag tgagcccaga    2520
tcgcaccact gcactccagt ctggcaacag agcaagactc catctcaaaa agaaaagaaa    2580
agaagactct gacctgtact cttgaataca agtttctgat accactgcac tgtctgagaa    2640
tttccaaaac tttaatgaac taactgacag cttcatgaaa ctgtccacca agatcaagca    2700
gagaaaataa ttaatttcat gggactaaat gaactaatga ggataatatt ttcataattt    2760
tttatttgaa atttttgctga ttctttaaat gtcttgtttc ccagatttca ggaaacttttt    2820 tttcttttaa gctatccaca gcttacagca atttgataaa atatactttt gtgaacaaaa    2880
attgagacat ttcatttttc tccctatgtg gtcgctccag acttgggaaa ctattcatga    2940
atatttatat tgtatggtaa tatagttatt gcacaagttc aataaaaatc tgctctttgt    3000
atgacagaat acatttgaaa acattggtta tattaccaag actttgacta gaatgtcgta    3060
tttgaggata taaacccata ggtaataaac ccacaggtac tacaaacaaa gtctgaagtc    3120
```

| | |
|---|---|
| agccttggtt tggcttccta gtgtcaatta aacttctaaa agtttaatct gagattcctt | 3180 |
| ataaaaactt ccagcaaagc aactttaaaa aagtctgtgt gggccgggcg cggtggctca | 3240 |
| cgcctgtaat cccagcactt tgatccgccg aggcgggcgg atcacgaggt caggagatcc | 3300 |
| agaccatcct ggctaacaca gtgaaacccc gtctctacta aaaatacaaa aaagttagc | 3360 |
| cgggcgtggt ggtgggggcc tgtagtccca gctactcagg aggctgaggc aggagaacgg | 3420 |
| catgaacccg ggaggcaggg cttgcagtga gccaagatca tgccgctgca ctccagcctg | 3480 |
| ggagacaaag tgagactccg tcaaaaaaaa aaaaagtct atgtggtcag tcactactct | 3540 |
| tgctgcagtt atgaaagaa tgaggccaag tctgatgaaa ataaacttat tttgaaaaca | 3600 |

<210> SEQ ID NO 4
<211> LENGTH: 5748
<212> TYPE: DNA
<213> ORGANISM: Homo sapiens

<400> SEQUENCE: 4

| | |
|---|---|
| gagaagaaag ccagtgcgtc tctgggcgca ggggccagtg gggctcggag gcacaggcac | 60 |
| cccgcgacac tccaggttcc ccgacccacg tccctggcag ccccgattat ttacagcctc | 120 |
| agcagagcac ggggcggggg cagaggggcc cgcccgggag ggctgctact tcttaaaacc | 180 |
| tctgcgggct gcttagtcac agcccccctt gcttgggtgt gtccttcgct cgctccctcc | 240 |
| ctccgtctta ggtcactgtt ttcaacctcg aataaaaact gcagccaact tccgaggcag | 300 |
| cctcattgcc cagcggaccc cagcctctgc caggttcggt ccgccatcct cgtcccgtcc | 360 |
| tccgccggcc cctgccccgc gcccagggat cctccagctc cttcgcccg cgccctccgt | 420 |
| tcgctccgga caccatggac aagttttggt ggcacgcagc ctgggactc tgcctcgtgc | 480 |
| cgctgagcct ggcgcagatc gatttgaata taacctgccg cttgcaggt gtattccacg | 540 |
| tggagaaaaa tggtcgctac agcatctctc ggacggaggc cgctgacctc tgcaaggctt | 600 |
| tcaatagcac cttgcccaca atgggcccaga tggagaaagc tctgagcatc ggatttgaga | 660 |
| cctgcaggta tgggttcata gaagggcacg tggtgattcc ccggatccac cccaactcca | 720 |
| tctgtgcagc aaacaacaca ggggtgtaca tcctcacatc caacacctcc cagtatgaca | 780 |
| catattgctt caatgcttca gctccacctg aagaagattg tacatcagtc acagacctgc | 840 |
| ccaatgcctt tgatggacca attaccataa ctattgttaa ccgtgatggc acccgctatg | 900 |
| tccagaaagg agaatacaga acgaatcctg aagacatcta ccccagcaac cctactgatg | 960 |
| atgacgtgag cagcggctcc tccagtgaaa ggagcagcac ttcaggaggt tacatctttt | 1020 |
| acacctttc tactgtacac cccatcccag acgaagacag tcctggatc accgacagca | 1080 |
| cagacagaat ccctgctacc actttgatga gcactagtgc tacagcaact gagacagcaa | 1140 |
| ccaagaggca agaaacctgg gattggtttt catggttgtt tctaccatca gagtcaaaga | 1200 |
| atcatcttca cacaacaaca caaatggctg gtacgtcttc aaataccatc tcagcaggct | 1260 |
| gggagccaaa tgaagaaat gaagatgaaa gagacagaca cctcagtttt tctgatcag | 1320 |
| gcattgatga tgatgaagat tttatctcca gcaccatttc aaccacacca cgggcttttg | 1380 |
| accacacaaa acagaaccag gactggaccc agtggaaccc aagccattca aatccggaag | 1440 |
| tgctacttca dacaaccaca aggatgactg atgtagacag aaatggcacc actgcttatg | 1500 |
| aaggaaactg gaacccagaa gcacaccctc cctcattca ccatgagcat catgaggaag | 1560 |
| aagagacccc acattctaca agcacaatcc aggcaactcc tagtagtaca acggaagaaa | 1620 |
| cagctaccca gaaggaacag tggtttggca acagatggca tgagggatat cgccaaacac | 1680 |

```
ccaaagaaga ctcccattcg acaacaggga cagctgcagc ctcagctcat accagccatc   1740
caatgcaagg aaggacaaca ccaagcccag aggacagttc ctggactgat ttcttcaacc   1800
caatctcaca ccccatggga cgaggtcatc aagcaggaag aaggatggat atggactcca   1860
gtcatagtat aacgcttcag cctactgcaa atccaaacac aggtttggtg gaagatttgg   1920
acaggacagg acctctttca atgcaacgc agcagagtaa ttctcagagc ttctctacat   1980
cacatgaagg cttggaagaa gataaagacc atccaacaac ttctactctg acatcaagca   2040
ataggaatga tgtcacaggt ggaagaagag acccaaatca ttctgaaggc tcaactactt   2100
tactggaagg ttatacctct cattacccac acacgaagga aagcaggacc ttcatcccag   2160
tgacctcagc taagactggg tcctttggag ttactgcagt tactgttgga gattccaact   2220
ctaatgtcaa tcgttcctta tcaggagacc aagacacatt ccaccccagt gggggtccc    2280 ataccactca tggatctgaa tcagatggac actcacatgg gagtcaagaa ggtggagcaa   2340
acacaacctc tggtcctata aggacacccc aaattccaga atggctgatc atcttggcat   2400
ccctcttggc cttggctttg attcttgcag tttgcattgc agtcaacagt cgaagaaggt   2460
gtgggcagaa gaaaaagcta gtgatcaaca gtggcaatgg agctgtggag acagaaagc    2520 caagtggact caacggagag gccagcaagt ctcaggaaat ggtgcatttg gtgaacaagg   2580
agtcgtcaga aactccagac cagttttatga cagctgatga gacaaggaac ctgcagaatg   2640
tggacatgaa gattggggtg taacacctac accattatct tggaaagaaa caaccgttgg   2700
aaacataacc attacaggga gctgggacac ttaacagatg caatgtgcta ctgattgttt   2760
cattgcgaat cttttttagc ataaaattt ctactctttt tgtttttgt gttttgttct     2820 ttaaagtcag gtccaatttg taaaaacagc attgctttct gaaattaggg cccaattaat   2880
aatcagcaag aatttgatcg ttccagttcc cacttggagg cctttcatcc ctcgggtgtg   2940
ctatggatgg cttctaacaa aaactacaca tatgtattcc tgatcgccaa cctttccccc   3000
accagctaag gacatttccc agggttaata gggcctggtc cctgggagga aatttgaatg   3060
ggtccatttt gcccttccat agcctaatcc ctgggcattg cttccactg aggttggggg    3120 ttggggtgta ctagttacac atcttcaaca gacccctct agaaatttt cagatgcttc     3180 tgggagacac ccaaagggtg aagctattta tctgtagtaa actatttatc tgtgtttttg   3240
aaatattaaa ccctggatca gtcctttgat cagtataatt ttttaaagtt actttgtcag   3300
aggcacaaaa gggtttaaac tgattcataa taaatatctg tacttcttcg atcttcacct   3360
tttgtgctgt gattcttcag tttctaaacc agcactgtct gggtccctac aatgtatcag   3420
gaagagctga gaatggtaag gagactcttc taagtcttca tctcagagac cctgagttcc   3480
cactcagacc cactcagcca aatctcatgg aagaccaagg agggcagcac tgttttgtt    3540 ttttgttttt tgtttttttt ttttgacact gtccaaaggt tttccatcct gtcctggaat   3600
cagagttgga agctgaggag cttcagcctc ttttatggtt taatggccac ctgttctctc   3660
ctgtgaaagg cttttgcaaag tcacattaag tttgcatgac ctgttatccc tggggcccta   3720
tttcatagag gctggcccta ttagtgattt ccaaaaacaa tatggaagtg ccttttgatg   3780
tcttacaata agagaagaag ccaatggaaa tgaaagagat tggcaaaggg gaaggatgat   3840
gccatgtaga tcctgtttga cattttatg gctgtatttg taaacttaaa cacaccagtg    3900
tctgttcttg atgcagttgc tatttaggat gagttaagtg cctggggagt ccctcaaaag   3960
gttaaaggga ttcccatcat tggaatctta tcaccagata ggcaagttta tgaccaaaca   4020
```

-continued

```
agagagtact ggctttatcc tctaacctca tattttctcc cacttggcaa gtcctttgtg    4080
gcatttattc atcagtcagg gtgtccgatt ggtcctagaa cttccaaagg ctgcttgtca    4140
tagaagccat tgcatctata aagcaacggc tcctgttaaa tggtatctcc tttctgaggc    4200
tcctactaaa agtcatttgt tacctaaact tatgtgctta acaggcaatg cttctcagac    4260
cacaaagcag aaagaagaag aaaagctcct gactaaatca gggctgggct tagacagagt    4320
tgatctgtag aatatcttta aaggagagat gtcaactttc tgcactattc ccagcctctg    4380
ctcctccctg tctaccctct cccctccctc tctccctcca cttcacccca caatcttgaa    4440
aaacttcctt tctcttctgt gaacatcatt ggccagatcc attttcagtg gtctggattt    4500 cttttattt tcttttcaac ttgaaagaaa ctggacatta ggccactatg tgttgttact    4560
gccactagtg ttcaagtgcc tcttgttttc ccagagattt cctgggtctg ccagaggccc    4620
agacaggctc actcaagctc tttaactgaa aagcaacaag ccactccagg acaaggttca    4680
aaatggttac aacagcctct acctgtcgcc ccagggagaa aggggtagtg atacaagtct    4740
catagccaga gatggttttc cactccttct agatattccc aaaaagaggc tgagacagga    4800
ggttattttc aattttattt tggaattaaa tacttttttc cctttattac tgttgtagtc    4860
cctcacttgg atatacctct gttttcacga tagaaataag ggaggtctag agcttctatt    4920
ccttggccat tgtcaacgga gagctggcca agtcttcaca aacccttgca acattgcctg    4980
aagtttatgg aataagatgt attctcactc ccttgatctc aagggcgtaa ctctggaagc    5040
acagcttgac tacacgtcat ttttaccaat gattttcagg tgacctgggc taagtcattt    5100
aaactgggtc tttataaaag taaaaggcca acatttaatt attttgcaaa gcaacctaag    5160
agctaaagat gtaattttc ttgcaattgt aaatcttttg tgtctcctga agacttccct    5220
taaaattagc tctgagtgaa aaatcaaaag agacaaaaga catcttcgaa tccatatttc    5280
aagcctggta gaattggctt ttctagcaga acctttccaa aagttttata ttgagattca    5340
taacaacacc aagaattgat tttgtagcca acattcattc aatactgtta tatcagagga    5400
gtaggagaga ggaaacattt gacttatctg gaaaagcaaa atgtacttaa gaataagaat    5460
aacatggtcc attcacctt atgttataga tatgtctttg tgtaaatcat ttgttttgag    5520
ttttcaaaga atagcccatt gttcattctt gtgctgtaca atgaccactg ttattgttac    5580
tttgactttt cagagcacac ccttcctctg gtttttgtat atttattgat ggatcaataa    5640
taatgaggaa agcatgatat gtatattgct gagttgaaag cacttattgg aaaatattaa    5700
aaggctaaca ttaaaagact aaaggaaaca gaaaaaaaaa aaaaaaa                  5748
```

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5

```
gatccccgga ccctcactct attcaattca agagattgaa tagagtgagg gtccttttc      60
```

SELECTIN LIGANDS USEFUL IN THE DIAGNOSIS AND TREATMENT OF CANCER

REFERENCE TO RELATED APPLICATIONS

This application is a Continuation application of U.S. patent application Ser. No. 12/919,902, filed Aug. 27, 2010, which is a U.S. national stage application under 35 U.S.C. §371 of PCT/US2009/035724 filed Mar. 2, 2009, and claims the benefit of U.S. Provisional Application Ser. No. 61/067,438, filed Feb. 28, 2008, and U.S. Provisional Application Ser. No. 61/072,945, filed Apr. 3, 2008, each of which is incorporated herein by reference.

STATEMENT OF GOVERNMENTAL INTEREST

This invention was made with U.S. government support under grant no. RO1 CA101135 from the National Institutes of Health. The U.S. government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Oct. 26, 2012, is named 22428977.txt and is 28,681 bytes in size.

FIELD OF THE INVENTION

The present invention relates to the field of cancer. More specifically, the present invention relates to diagnosis and treatment of cancer.

BACKGROUND OF THE INVENTION

Blood-borne metastasis is a highly orchestrated and dynamic process initiated when cancerous cells disassociate from a primary tumor and migrate across vessel walls into the circulation. During their passage through the vascular system, tumor cells are exposed to mechanical and immunological stresses, which affect their ability to metastasize. Only tumor cells uniquely fit to overcome or even exploit the detrimental effects of hemodynamic forces and immunosurveillance will adhere to the vascular endothelium of distant organs, extravasate and successfully colonize these sites.

The adhesive interactions of circulating tumor cells (CTCs) with host cells including platelets, leukocytes and endothelial cells may regulate their extravasation from the vasculature. Platelets, by forming heterotypic complexes with tumor cells, may mask them from immune-mediated mechanisms of clearance. Palumbo et al., 105 BLOOD 178-185 (2005); Borsig et al., 99 PROC. NATL. ACAD. SCI. USA 2193-2198 (2002); Borsig et al., 98 PROC. NATL. ACAD. SCI. USA 3352-3357 (2001); and Nieswandt et al., 59 CANCER RES. 1295-1300 (1999) Alternatively, platelets may potentiate tumor cell adhesion to the vessel wall (Burdick et al., 287 J. PHYSIOL. CELL. PHYSIOL. 539-547 (2004) and release an array of bioactive compounds such as vascular endothelial growth factor at points of attachment to endothelium, thereby promoting vascular hyperpermeability and extravasation (Nash et al., 3 LANCET ONCOL. 425-430 (2002)). Moreover, polymorphonuclear leukocytes (PMNs) facilitate tumor cell extravasation in vitro (Slattery et al., 106 INT. J. CANCER 713-722 (2003); Starkey et al., 34 INT. J. CANCER 535-543 (1984)), and promote the arrest and deposition of tumors in the microvasculature of target organs in animal models (Starkey et al., 34 INT. J. CANCER 535-543 (1984)). PMN-facilitated tumor cell extravasation under dynamic flow conditions involves initial PMN tethering on the endothelium and subsequent arrest of free-flowing tumor cells by tethered PMNs. Lian et al., 295 AM. J. PHYSIOL. CELL PHSIOL. C701-707 (2008).

Selectins may facilitate cancer metastasis and tumor cell arrest in the microvasculature by mediating specific interactions between selectin-expressing host cells and ligands on tumor cells. The molecular and biochemical underpinnings of selectin-ligand interactions involved in heterotypic tumor cell-host cell adhesion events are not well understood. There is a need for new therapeutics and diagnostics for metastatic cancer.

SUMMARY OF THE INVENTION

The invention provides therapeutics and diagnostics for cancer metastasis using selectin ligands as biomarkers for the tissue specific biochemistry of malignant versus normal tissue.

The invention provides therapeutics and diagnostics for cancer metastasis using selectin ligands as biomarkers for the tissue specific biochemistry of malignant versus normal tissue. In one embodiment, the present invention provides a targeting composition comprising (a) a solid substrate; and (b) an antibody composition bound to the substrate, comprising at least one antibody to one or more E-selectin and L-selectin ligand antigens, the antigens comprising podocalyxin-like protein (PCLP) or two or more of PCLP, carcinoembryonic antigen (CEA), and CD44v, the antibody composition binding specifically to metastatic tumor cells having E-selectin and L-selectin binding activity, wherein the substrate is a patterned array and/or the composition further comprises a therapeutic or imaging agent bound to the substrate or antibody.

In a particular embodiment, the substrate may be a particle suspendable in a biocompatible medium. The particle may be selected from the group consisting of a nanoparticle, a quantum dot, a liposome, a micelle and a polymersome. In a specific embodiment, the substrate is a quantum dot. In another embodiment, the nanoparticle is a gold nanoparticle. Alternatively, the substrate may be an array.

In another embodiment, the at least one antibody is selected from the group consisting of a polyclonal antibody, a monoclonal antibody, a recombinant antibody, a humanized antibody, a single chain antibody, and a Fab fragment. In a specific embodiment, the antibody composition comprises an antibody to CEA, an antibody to PCLP, and an antibody to CD44v. The antibody composition may comprise an antibody to PCLP and an antibody to CEA. In another embodiment, the antibody composition may comprise an antibody to PCLP and CD44v. The antibody composition may also comprise an antibody to CEA and CD44v. Furthermore, each of the at least one antibody may be conjugated to the substrate via at least one linker molecule.

In another aspect, the present invention provides a method for treating cancer comprising administering to a subject with cancer a therapeutically effective amount of a composition comprising a targeting composition, wherein the substrate is a particle suspendable in biocompatible medium, and further comprises at least one chemotherapeutic agent conjugated to the suspendable particle. In the method, the cancer may be a primary tumor. The targeting composition may also prevent migration of the cancer from the primary tumor site. In another embodiment, the cancer is a metastatic cancer. In a further embodiment, the targeting composition prevents formation of a secondary tumor.

The chemotherapeutic agent may be selected from the group consisting of paclitaxel, docetaxel, daunorubicin, cisplatin, carboplatin, oxaliplatin, colchicine, dolastatin 15, nocodazole podophyllotoxin, rhizoxin, vinblastine, vindesine, vinorelbine (navelbine), the epothilones, the mitomycins, bleomycin chlorambucil, cannustine, melphalan, mitoxantrone 5-fluoro-5'-deoxyuridine, camptothecin, topotecan, irinotecanetoposide, tenoposide, geldanamycin, methotrexate, adriamycin, actinomycin D, mifepristone, raloxifene, 5-azacytidine, 5-aza-2'-deoxycytidine, zebularine, tamoxifen, 4-hydroxytamoxifen apigenin, rapamycin, angiostatin K1-3, staurosporine, genistein, fumagillin, endostatin, thalidomide, analogs thereof and combinations thereof.

The present invention also provides a method for imaging a cancer cell in a patient comprising administering to a subject a pharmaceutically acceptable composition comprising a targeting composition, wherein the substrate is at least one particle suspendable in a biocompatible medium, and further comprises at least one imaging agent conjugated to the at least one particle; and detecting the at least one imaging agent. In one embodiment, the detecting step comprises using an imaging device. In a particular embodiment, the imaging agent may be selected from the group consisting of a radiologic contrast agent, diatrizoic acid sodium salt dihydrate, an iodine-containing agent, a barium-containing agent, a fluorescent imaging agent, Lissamine Rhodamine PE, a stain, a dye, a radioisotope, a metal, a ferromagnetic compound, a paramagnetic compound, gadolinium, a superparamagnetic compound, iron oxide, a diamagnetic compound, and barium sulfate.

In the method, the at least one antibody may be selected from the group consisting of a polyclonal antibody, a monoclonal antibody, a recombinant antibody, a humanized antibody, a single chain antibody, and a Fab fragment. More particularly, the antibody composition comprises an antibody to CEA, an antibody to PCLP, and an antibody to CD44v. In a specific embodiment, the antibody composition comprises an antibody to PCLP and an antibody to CEA. The antibody composition may also comprise an antibody to PCLP and CD44v. In an alternative embodiment, the antibody composition comprises an antibody to CEA and CD44v. Furthermore, the at least one antibody may be conjugated to the particle via at least one linker molecule.

With regard to the methods, the particle may be a nanoparticle, a quantum dot, a liposome, a micelle and a polymersome. In one embodiment, the particle is a quantum dot. In another embodiment, the particle is a gold nanoparticle.

The present invention further provides an array comprising a fixed matrix and an antibody composition bound to the fixed matrix in a predetermined pattern, comprising at least one antibody to one or more E-selectin and L-selectin ligand antigens, the antigens comprising podocalyxin-like protein (PCLP) or two or more of PCLP, carcinoembryonic antigen (CEA), and CD44v, the antibody composition binding specifically to metastatic tumor cells having E-selectin and L-selectin binding activity.

In one embodiment, the present invention provides a method for diagnosing metastatic cancer comprising obtaining a biological sample from a patient and contacting the sample with an array, wherein the specific binding by the targeting composition indicates the presence of metastatic cancer cells. In a specific embodiment, the array is a microarray. In another embodiment, the biological sample is blood.

The present invention further provides a method for preparing a targeting composition for metastatic tumor cells comprising binding an antibody composition to a substrate, the substrate being selected from a particle suspendable in a biocompatible medium and an array, and the antibody composition comprising at least one antibody to an E-selectin and L-selectin ligand antigen. The antigen may be selected from the group consisting of CEA, PCLP and CD44v.

The present invention also provides a composition comprising an antibody to PCLP, CEA, and/or CD44v conjugated with an imaging agent. The imaging agent may be a radioactive isotope. In a specific embodiment, the radioactive isotope is Iodine 131. The antibody may be selected from the group consisting of a polyclonal antibody, a monoclonal antibody, a recombinant antibody, a humanized antibody, a single chain antibody, and a Fab fragment. In a particular embodiment, the antibody is to PCLP.

In yet another embodiment, a method for imaging a cancer cell in a patient comprises administering to a subject a composition; and detecting the at least one imaging agent. The imaging agent may be selected from the group consisting of a radiologic contrast agent, diatrizoic acid sodium salt dihydrate, an iodine-containing agent, a barium-containing agent, a fluorescent imaging agent, Lissamine Rhodamine PE, a stain, a dye, a radioisotope, a metal, a ferromagnetic compound, a paramagnetic compound, gadolinium, a superparamagnetic compound, iron oxide, a diamagnetic compound, and barium sulfate.

Moreover, the antibody may be selected from the group consisting of a polyclonal antibody, a monoclonal antibody, a recombinant antibody, a humanized antibody, a single chain antibody, and a Fab fragment. In another embodiment, the detecting step comprises using an imaging device.

The present invention also provides a method of identifying a biomarker specific for metastatic cancer cells comprising selecting a putative glycopolypeptide selectin ligand found in a lysate of carcinoma cells; detecting selectin binding activity of the putative ligand in a blot rolling assay under shear flow conditions; identifying the putative glycopolypeptide selectin ligand, and measuring selectin binding activity of the identified glycopolypeptide selectin ligand in a cell-free flow-based adhesion study. The method may further comprise the step of obtaining an antibody specific to the glycopolypeptide selectin ligand, wherein the antibody is specific to metastatic cells of the carcinoma.

The carcinoma cells may be from colon, breast, prostate, squamous, neural blastoma, pancreatic, or lung cancer. In another embodiment, the identifying step comprises immunoaffinity chromatography, sequencing of isolated polypeptide fragments, and proteomics analysis.

The method may further comprise the step of preparing a derivative of the identified glycopolypeptide selectin ligand and retesting in a cell-free flow-based adhesion study. The derivative may be a glycoprotein, a peptide, or a peptidomimetic. In a particular embodiment, the identified glycopolypeptide selectin ligand is selected from PCLP, CEA, and CD44v. In another embodiment, the antibody is a monoclonal antibody.

Figure 1:
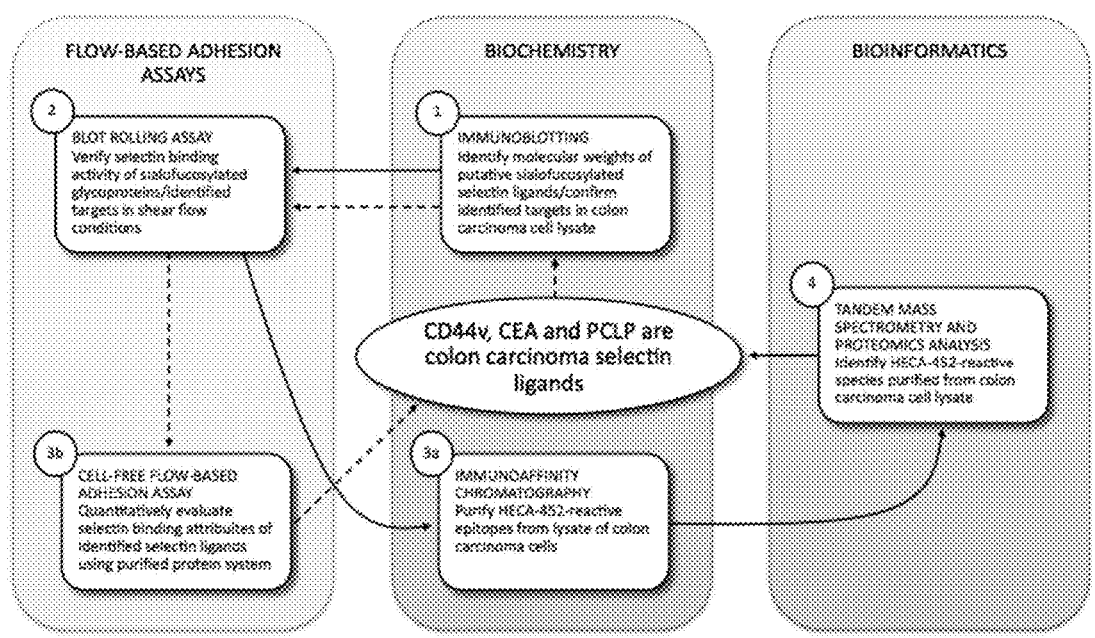
FIG. 1 is a schematic diagram outlining a methodology used to isolate, identify and verify carcinoma-expressed selectin ligands. A combination of biochemistry, flow-based adhesion assays and tandem mass spectrometry in conjunction with bioinformatics techniques was used to identify and subsequently verify PCLP, CD66e, and CD44v to be carcinoma-expressed selectin ligands. Solid lines denote chronological order of methods used to purify and identify targets. Dotted lines denote chronological order of methods used to verify targets as selectin ligands.

*p<0.05 with respect to microspheres coated with CD66e immunopurified from wildtype LS174T cells. ND: not done. Average rolling velocities of microspheres ($10^6$/ml) coated with CD66e immunopurified from wildtype or CD44-knockdown LS174T cells on 10 µg/ml E-selectin (D) or L-selectin (E) at prescribed wall shear stresses. Data represent the mean±S.E. *p<0.05 with respect to microspheres coated with CEA immunopurified from wildtype LS174T cells.

FIGS. 9A-9D provides results from CD66e-coated microspheres and flow cytometry experiments. A: Site densities of wildtype LS174T CD66e-coated polystyrene microspheres, pretreated with enzymes or metabolic inhibitors, determined by flow cytometry. Wildtype LS174T CD66e-absorbed microspheres were treated with *Vibrio cholerae* sialidase (0.1 U/ml). Alternatively, CD66e immunoprecipitated from N-glycosidase F-treated wildtype LS174T whole cell lysate was used to coat microspheres. In other experiments, microspheres were coated with CD66e immunoprecipitated from wildtype LS174T whole cell lysate pretreated with DMJ or benzyl-GalNAc. Site densities of adsorbed CD66e were quantified using a PE-conjugated anti-CD66 mAb (Bl.I) after treatments. B: Site densities of HECA-452-reactive epitopes on treated wildtype LS174T CD66e-coated microspheres determined by flow cytometry. C: Extent of adhesion of wildtype LS174T CD66e-coated polystyrene microspheres, pretreated with highly specific enzymes and perfused over 10 µg/ml E-(white bars) or L-selectin (black bars) at a wall shear stress level of 1 dyn/cm² for 2 min. Data represent the mean±S.E. *p<0.05 with respect to untreated control microspheres. D: Extent of adhesion of CD66e-coated microspheres generated using CD66e immunoprecipitated from wildtype LS174T cells cultured in the presence and absence (control) of metabolic inhibitors, and perfused over 10 µg/ml E-(white bars) or L-selectin (black bars) at a wall shear stress level of 1 dyn/cm² for 2 min. Data represent the mean±S.E. *p<0.05 with respect to control microspheres.

FIGS. 10A-10D provides results from additional CD66e, flow cytometry, and flow-based adhesion assays. A: Representative flow cytometric histograms of CD66, CD44 and CD29 expression by wildtype, CD44-knockdown, CD66e-knockdown, and CD66e/CD44-double knockdown LS174T cells. Cells were stained by indirect single-color immunofluorescence using the anti-CD66de mAb Col-I (solid line) or an isotype control antibody (dashed line). Alternatively, cells were stained with the PE-conjugated anti-CD44 mAb 515 (solid line) or PE-conjugated isotype control antibody (dashed line). In other experiments, cells were stained with the PE-conjugated anti-CD29 mAb MAR4 (solid line) or PE-conjugated isotype control antibody (dashed line). B: Extent of adhesion of wildtype, CD44-knockdown, CD66e-knockdown, and two distinct CD66e/CD44-double knockdown LS174T cell lines ($10^6$/ml) to E-selectin (0.75 µg/ml) under physiological flow conditions. The average number of wildtype LS174T cells per mm² that tethered and rolled on E-selectin at 1.0 and 2.0 dyn/cm² was 380±60 and 290±30, respectively. Data represent the mean±S.E. of n=3 experiments. Black bars represent data acquired at the wall shear stress level of 1.0 dyn/cm², whereas white bars represent data at 2.0 dyn/cm². *p<0.05 with respect to wildtype, CD44-knockdown and CD66e-knockdown LS174T cells. C: Extent of adhesion of wildtype, CD44-knockdown, CD66e-knockdown, and CD66e/CD44-double knockdown LS174T cells ($10^6$/ml) to L-selectin (1.5 µg/ml) under physiological flow conditions. The average number of wildtype LS174T cells per mm² that tethered and rolled on L-selectin at 1.0 and 2.0 dyn/cm² was 700±100 and 600±100, respectively. Data are normalized with respect to wildtype LS174T cells, and represent the mean±S.E. of n=3-4 experiments. Black bars represent data acquired at the wall shear stress level of 1.0 dyn/cm², whereas white bars represent data at 2.0 dyn/cm². *p<0.05 with respect to wildtype, CD44-knockdown and CD66e-knockdown LS174T cells. D: Extent of adhesion of wildtype, CD44-knockdown, CD66e-knockdown, and CD66e/CD44-double knockdown LS174T cells (106/ml) to P-selectin (1.5 µg/ml) under physiological flow conditions. The average number of wildtype LS174T cells per mm² that tethered and rolled on P-selectin at 1.0 and 2.0 dyn/cm² was 1200±200 and 610±90, respectively. Data are normalized with respect to wildtype LS174T cells, and represent the mean±S.E. of n=3 experiments. Black bars represent data acquired at the wall shear stress level of 1.0 dyn/cm², whereas white bars represent data at 2.0 dyn/cm². *p<0.05 with respect to wildtype and CEA-knockdown LSI 74T cells.

Figure 11:
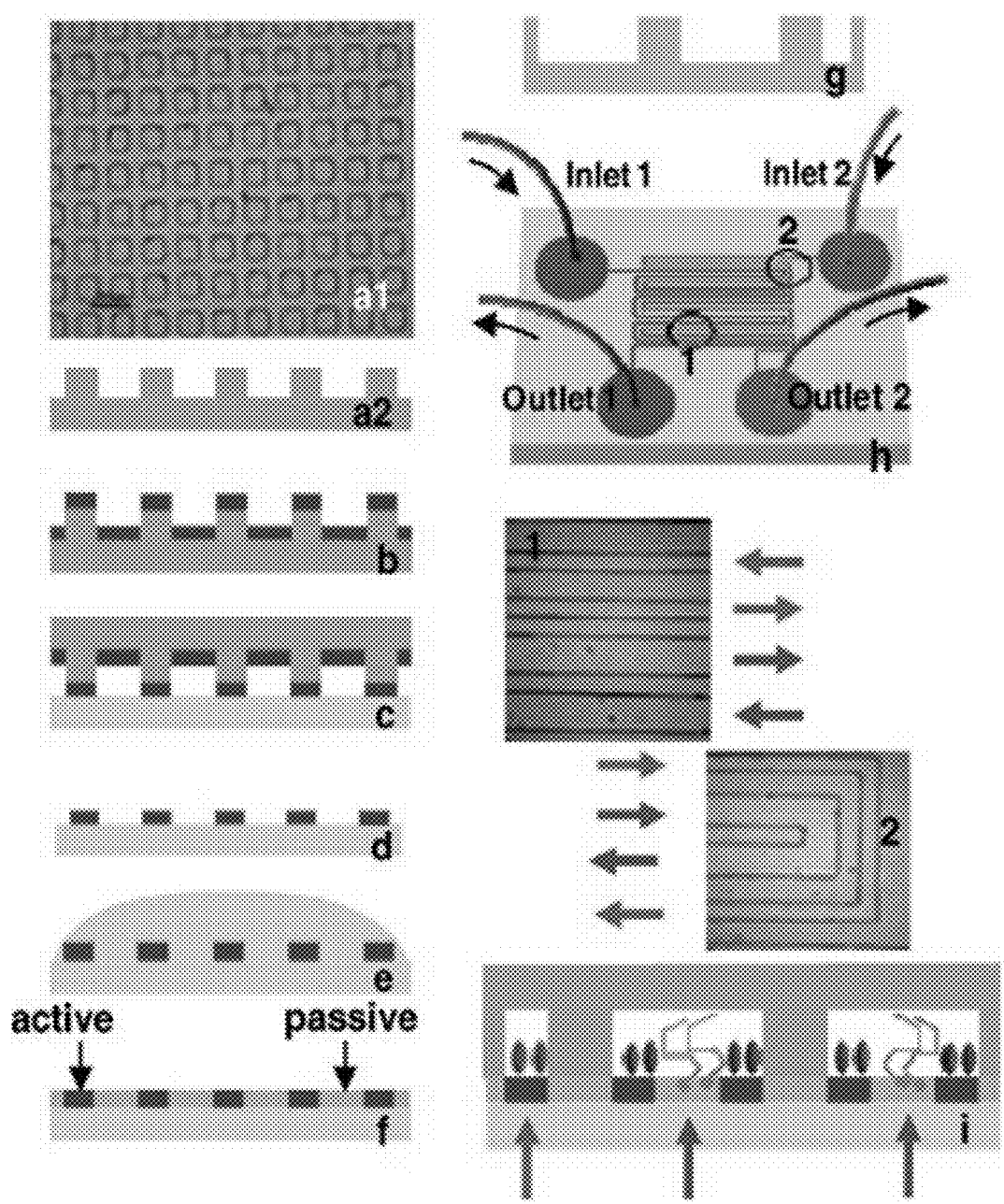

FIG. 11 is a schematic illustration showing the creation of multifunctional surfaces by serial use of micro contact printing (µCP) (left panel) and microfluidics (right panel). A PDMS stamp (a1, a2) inked with an active species that promotes adsorption (b) is contacted with the substrate (c), rinsed (d), and backfilled with a passive species that prevents adsorption (e, f). The substrate is affixed as a lid to a microfluidics (MF) network with n channels (g) through which adsorbing species are introduced. (h) shows MF network of two channels. Images of the indicated areas of the actual MF network with flow directions within the network are shown in (1) and (2). By this method, surfaces presenting n species on distinct patches surrounded by continuous passivated regions are created. The pictures are not drawn to scale.

Figure 12:
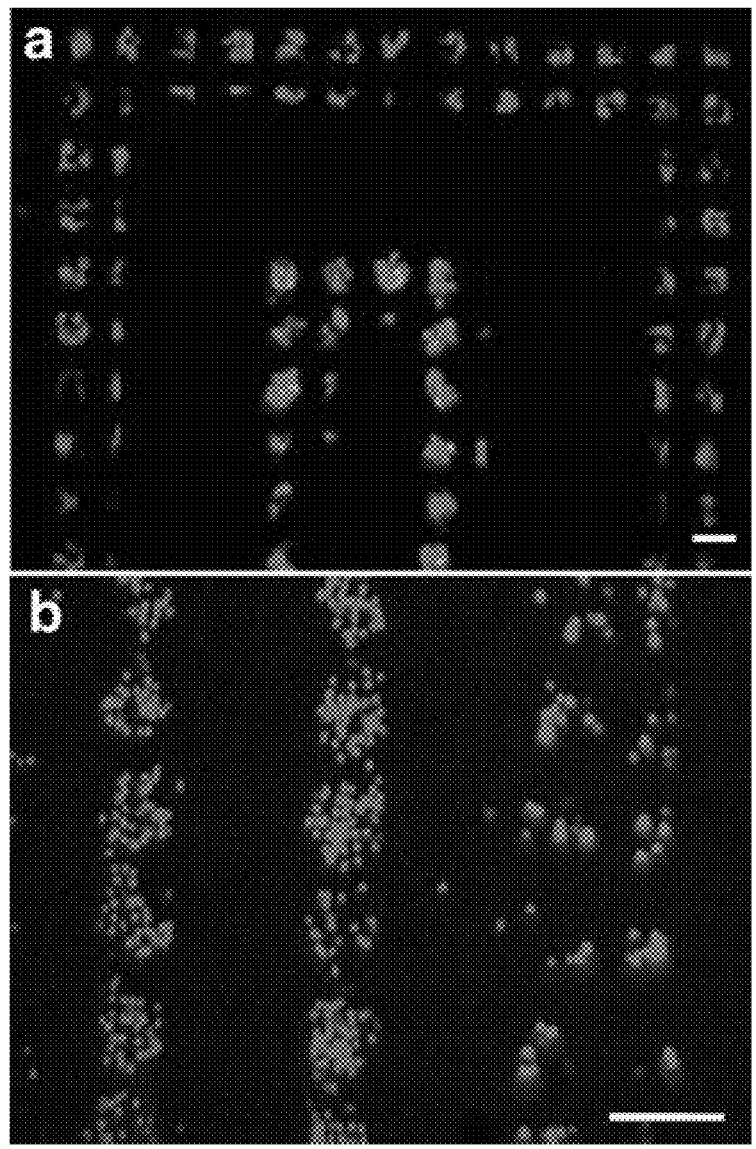

FIG. 12 shows results of an experiment described herein and in particular, FIG. 3. Multifunctional surfaces with discrete functionalized regions were created to capture normal versus malignant cells from mixed cell suspensions. Sorting of a mixture of CMFDA-labeled LS174T colon carcinoma cells (green; also referred to by indicator number 20) and SNARF-stained polymorphonuclear leukocytes (PMNs) (red; also referred to by indicator number 10) on anti-PSGL1 and anti-CEA mAb micropatterned glass slides surrounded by PEG-functionalized regions. (a) The cell mixture was incubated for 30 min on the slide. (b) The cell mixture was perfused over the micropatterned glass slide through a parallel plate flow chamber assay at 0.35 dyn/cm². For the multicolored images (not shown), two separate gray scale images of the fluorophores are taken, color labeled, and merged with Image J. The scale bars represent 100 µm. LS174T colon carcinoma cells 20 were effectively sorted from PMNs 10 into prescribed patches under both static and physiological flow conditions.

DETAILED DESCRIPTION OF THE INVENTION

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Selectin Ligands

The targeting compositions and related methods of the present invention are useful in diagnosing, detecting, imaging, treating, and/or preventing cancer. In particular, the targeting compositions are designed to bind to ligands expressed on cancer cells, which ligands typically bind selectins expressed on epithelial cells.

Furthermore, the inventive compositions and methods involve targeting antibodies to antigens that are specific to metastatic tumor cells, for example sialomucin markers for metastatic carcinoma such as sialofucosylated glycoprotein antigens that include a selectin binding determinant. A cell-free flow-based adhesion assay as described herein has been used to identify three such antigens (PCLP, CEA, and C44v) and may be used to identify peptides, peptidomimetics, or other suitable variants of these proteins, or other proteins or variants.

Figure 2:
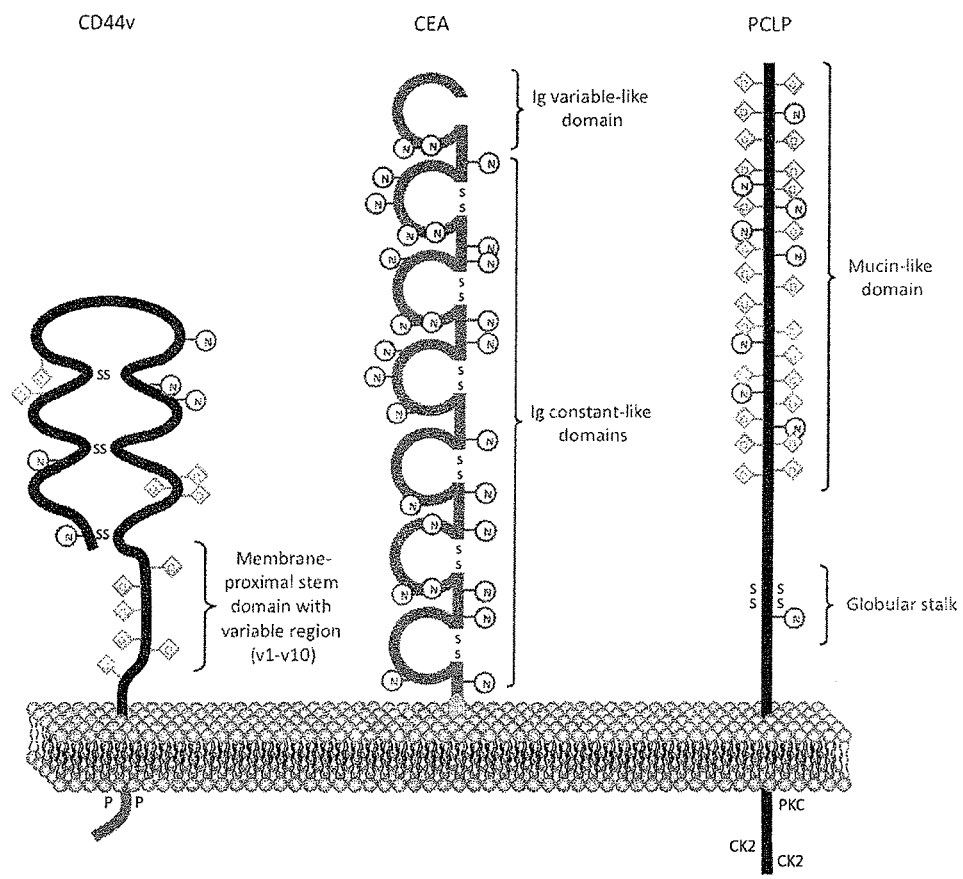
FIG. 2 is a schematic diagram of colon carcinoma cell-expressed selectin ligands PCLP, CD66e, and CD44v. Diamond-enclosed Os represent putative sites for 0-linked glycosylation. Circled Ns represent putative sites for N-linked glycosylation, SS represents disulfide bonds, P represents serine phosphatases, PKC represent Protein Kinase C site, CK2 represents Casein Kinase 2 site. CD663 is GPI-linked to the cell membrane whereas CD44v and PCLP are type I transmembrane glycoproteins. Membrane proximal stem domain of CD44v and mucin-like domain of PCLP do not depict all putative sites for posttranslational modifications in this diagram.

In one embodiment, the targeting composition comprises at least one antibody to one or more E-selectin and L-selectin ligand antigens. In a specific embodiment, the selectin ligand comprises podocalyxin-like protein (PCLP). PCLP is a type I transmembrane sialoprotein and a member of the CD34 subfamily of sialomucins, which includes CD34 and endoglycan with whom PCLP shares a considerable degree of structural and functional homology. See Fumessand et al., 34 IMMUNOL. RES. 13-32 (2006); Takeda et al., 11 MOL. BIOL. CELL 3219-3232 (2000). Structural similarities include an N-terminus-proximal mucin-like domain with numerous sites for putative N- and O-linked glycosylation, four cysteines available for disulfide formation in the globular stalk domain, and a one-pass transmembrane domain. See FIG. 2; Kershaw et al., 272 J. BIOL. CHEM. 15708-15714 (1997). At the cytoplasmic tail, PCLP possesses consensus phosphorylation sites as well as a C-terminal PDZ docking motif. Fumessand et al., 34 IMMUNOL. RES. 13-32 (2006). The human PCLP gene (PODXL) is located at chromosome 7q32-q33. Kershaw et al., 272 J. BIOL. CHEM. 15708-15714 (1997).

PCLP was first described as a kidney podocyte surface-expressed molecule, which maintains the integrity of the filtration slits in the foot processes in the kidney glomerulus via its anti-adhesive properties due to a high net negative charge. Fumessand et al., 34 IMMUNOL. RES. 13-32 (2006). Mice lacking podocalyxin die soon after birth with defective kidney development and anuria. Doyonnas et al., 194 J. EXP. MED. 13-27 (2001). PCLP is also expressed in other cell types including early hematopoietic precursors, developing but not mature hematopoietic stem cells, and in high endothelial venules (HEVs). Furnessand et al., 34 IMMUNOL. RES. 13-32 (2006). As opposed to its anti-adhesive function in kidney podocytes, HEV-expressed PCLP mediates L-selectin-dependent lymphocyte recruitment to secondary lymphoid tissues. Sassetti et al., 187 J. EXP. MED. 1965-1975 (1998).

The nucleotide and amino acid sequences encoding PCLP are known in the art and are easily retrievable by known methods. The database accession number for PCLP variant1 is NM_001018111.2 (SEQ ID NO:1), and PCLP variant2 is NM_005397.3 (SEQ ID NO: 2), the entire sequences of which are incorporated herein by reference.

In another embodiment, the selectin ligand comprises carcinoembryonic antigen (CEA). The CEA gene family is tandemly arranged on chromosome 19q13.2 and is divided into major subfamilies, including CEA cell adhesion molecule (CEACAM) and pregnancy-specific glycoprotein, based on corresponding domain sequence homologies. Beauchemin et al., 252 EXP. CELL RES. 243-249 (1999); and Obrink, 9 CURR. OPIN. CELL. BIOL. 616-626 (1997). As immunoglobulin (Ig) family members, every CEACAM molecule contains an N-terminal Ig variable-like domain, which lacks an intra-chain disulfide link followed by a variable number (zero-six) of Ig C2-type constant-like domains. Harmmarstrom, 9 SEMIN. CANCER BIOL. 67-81 (1999). The largest member of the CEACAM family, CEA (used interchangeably with CEACAM5, CD66, and CD66e), is a glycosyl phosphatidyl inositol (GPI)-cell surface anchored glycoprotein that possesses six Ig C2-type domains. See FIG. 2. Sequence analysis has revealed multiple sites for putative N-glycosylation by multi-antennary complex type carbohydrate chains, which may constitute up to 50% of its total mass. Hammarstrom, 9 SEMIN. CANCER BIOL. 67-81 (1999); Paxton et al., 84 PROC. NATL. ACAD. SCI. USA 920-924 (1987).

The nucleotide and amino acid sequences encoding CEA are known in the art and are easily retrievable by known methods. The database accession number for CEA is NM_004363.2 (SEQ ID N0:3), the entire sequence of which is incorporated herein by reference.

In another embodiment, the selectin ligand comprises carcinoembryonic antigen (CEA). The CEA gene family is tandemly arranged on chromosome 19q13.2 and is divided into major subfamilies, including CEA cell adhesion molecule (CEACAM) and pregnancy-specific glycoprotein, based on corresponding domain sequence homologies. Beauchemin et al., 252 EXP. CELL REs. 243-249 (1999); and Obrink, 9 CURR. OPIN. CELL. BIOL. 616-626 (1997). As immunoglobulin (Ig) family members, every CEACAM molecule contains an N-terminal Ig variable-like domain, which lacks an intra-chain disulfide link followed by a variable number (zero-six) of Ig C2-type constant-like domains. Hammarstrom, 9 SEMIN. CANCER BIOL. 67-81 (1999). The largest member of the CEACAM family, CEA (used interchangeably with CEACAM5, CD66, and CD66e), is a glycosyl phosphatidyl inositol (GPI)-cell surface anchored glycoprotein that possesses six Ig C2-type domains. See FIG. 2. Sequence analysis has revealed multiple sites for putative N-glycosylation by multi-antennary complex type carbohydrate chains, which may constitute up to 50% of its total mass. Hammarstrom, 9 SEMIN. CANCER BIOL. 67-81 (1999); Paxton et al., 84 PROC. NATL. ACAD. SCI. USA 920-924 (1987).

The nucleotide and amino acid sequences encoding CEA are known in the art and are easily retrievable by known methods. The database accession number for CEA is NM_004363.2 (SEQ ID N0:3), the entire sequence of which is incorporated herein by reference.

In yet another embodiment, the selectin ligand comprises CD44v. CD44 proteins comprise a group of type I transmembrane molecules encoded by a single gene, which consists of at least 20 exons. Exons 1-5, 16-18 and 20 are spliced together to form the smallest CD44 transcript known as standard isoform (CD44s). At least ten exons (6-15; typically identified as v1-v10) encoding a membrane proximal portion of the extracellular domain of CD44 can be alternatively spliced and inserted at a single site between exons 5 and 16 to generate CD44v. See FIG. 2; and Ponta et al., 4 NAT. REV. MOL. CELL. BIOL. 33-45 (2003). See also Hanley et al., 20 FASEB J. 337-339 (2006). The CD44 protein family can function as: (i) a ligand binding receptor for various components of the extracellular matrix such as hyaluronan (HA), collagen, laminin and fibronectin; (ii) a platform for growth factors and other molecules such as metalloproteinases; (iii) a co-receptor which mediates the signaling of receptor tyrosine kinases; and (iv) an organizer of the cortical actin cytoskeleton. Id.

The nucleotide and amino acid sequences encoding CD44 are known in the art and are easily retrievable by known methods. The database accession number for CD44v is NM_000610 (SEQ ID NO: 4), the entire sequence of which is incorporated herein by reference.

Variants of the selectin ligands including PCLP, CEA, and CD44v may be used to generate other antibodies with increased or alternative functionality compared to commercially available antibodies. In particular, the nucleotide and amino acid sequences of the ligands may be analyzed using known methods to identify particular and potential binding sites for antibodies. In addition, comparative analysis of the ligands expressed on normal versus cancer cells will result in the identification of particular conformational differences (including glycosylation patterns) that may be used to generate antibodies that will recognize ligands expressed only on cancer cells, thereby reducing or eliminating any cross-reactivity.

When referring to a ligand or a ligand expressed on the surface of a cell including a metastatic tumor cell, the phrase "E-selectin and L-selectin binding activity", means that the ligand has a higher affinity for E-selectin and L-selectin than for other molecular structures typically found on cell surfaces. In a more narrow sense, E-selectin and L-selectin binding activity or binding selectivity refers to those ligands which have a higher affinity for E-selectin and L-selectin than for other cell adhesion molecules which are related to E-selectin and L-selectin, such as P-selectin.

"E-selectin and L-selectin ligand antigens" refers to a ligand that specifically binds to E-selectin and L-selectin and includes, for example, CEA, PCLP, and CD44v. The term also includes other sialofucosylated glycoproteins that specifically bind E-selectin and L-selectin. The term further includes all derivatives, analogs, peptidomimetics, and fragments of the foregoing that exhibit E-selectin and L-selectin binding activity.

Table 1 below summarizes the biochemical differences in the recently identified selectin ligands expressed by normal versus malignant cells

TABLE 1

Biochemical and known selectin binding characteristics of normal cell-versus malignant cell-expressed selectin ligands.

|  | PSGL-1 | PCLP |  | CD44 |  |  | CD24 |
|---|---|---|---|---|---|---|---|
| Cell Type | Leukocytes, platelets | Colon, Neuroblastoma, Small Cell Lung Carcinoma | HEVs | Colon (CD44v) | HPC (CD44s) | Breast, Small Cell Lung Carcinoma | Neutrophils |
| Cell Line | Primary | LS174T, SK-N-SH, NCI-H128 | Primary | LS174T, T84, Colo205 | KG1a | KS, SW2 | Primary |
| MW (kDa) | 240 | 150-180 | 160 | 150 | 98 | 45 | 45 |
| High affinity selectin binding | E, L, P (18) | E, L | L (47) | E, L, P (17, 44) | E(11), L(13) | P (1, 2) | P (2) |
| Selectin binding glycan | O-linked (36, 37) | O-linked | O-linked (47) | O-linked (17, 44) | N-linked (11, 13) | O-linked (2) | O-linked (2) |
| GPI-linked | No | No | No | No | No | Yes | Yes |
| Sialidase-sensitive | E(55) (L, P:ND) | E*, L | L (47) | E†, L, P (17, 44) | E (12) (L:ND) | Partially (2) | No(2) |
| MECA-79-reactive | ND | No | Yes | ND | No‡ (11) | ND | ND |

The second, fourth, sixth and eight columns represent selectin ligands expressed in normal (host) cells, the third, fifth, and seventh columns represent selectin ligands expressed by malignant cells. LS174T, T84 and Colo 205: colon carcinoma cell lines; KS: breast carcinoma cell line; NCI-H128 and SW2: small cell lung cancer cell line; SK-N-SH: neuroblastoma cell line; HL-60: myeloid cell line; KG1a: hematopoetic progenitor cell line (HPC). *Sialidase-treated LS174T PCLP retained <20% tethering to E-selectin. †Sialidase-treated LS174T CD44 retained >60% tethering to E-selectin compared with the control. Selectin-dependent adhesion was shown to be sulfation-independent by chlorate treatment. ND: no data.

Antibodies to Selectin Ligands

The present invention contemplates the use of antibodies specific for selectin ligands including PCLP, CEA, and CD44v. The phrases "binding specificity," "binding specifically to, "specific binding" or otherwise any reference to an antibody to PCLP, CEA, and/or CD44v, refers to a binding reaction that is determinative of the presence of the corresponding antigen to the antibody in a heterogeneous population of antigens and other biologics. Thus, the specified antibodies bind selectively to an antigen present on a target cell and do not substantially bind in a statistically significant amount to other non-target cells. The parameters required to achieve such specificity can be determined routinely, using conventional methods in the art including, but not limited to, competitive binding studies. For example, an antibody of the invention may bind at least about 25% to 100 fold, or more, as efficiently to an antigen expressed on a target cell than it binds to other antigens expressed on non-target cells in a sample.

"Immunoglobulins" (Igs) and "antibodies" are glycoproteins having the same structural characteristics. These terms are used interchangeably herein.

Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The terms "antibody" and "immunoglobulin" cover fully assembled antibodies and antibody fragments that can bind antigen (e.g., Fab', F(ab)$_2$, Fv, single chain antibodies, diabodies), including recombinant antibodies and antibody fragments. In certain embodiment, the immunoglobulins or antibodies are chimeric, human, or humanized.

The variable domains of the heavy and light chain recognize or bind to a particular epitope of a cognate antigen. The term "epitope" is used to refer to the specific binding sites or antigenic determinant on an antigen that the variable end of the immunoglobulin binds. Epitopes can be linear, i.e., be composed of a sequence of amino acid residues found in the primary selectin ligand sequence. Epitopes also can be conformational, such that an immunoglobulin recognizes a 3-D structure found on a folded selectin ligand as expressed on the surface of a cancer cell, such that the amino acids recognized are not necessarily contiguous in the primary sequence. Epitopes can also be a combination of linear and conformational elements. Further, carbohydrate portions of a molecule, as expressed by the target bearing tumor cells can also be epitopes.

Antibodies are said to be "specifically binding" if: 1) they exhibit a threshold level of binding activity, and/or 2) they do not significantly cross-react with known related polypeptide molecules. The binding affinity of an antibody can be readily determined by one of ordinary skill in the art, for example, by Scatchard analysis (Scatchard, ANN. NY ACAD. Sci. 51: 660-672, 1949). In some embodiments, the immunoglobulins of the present invention bind to a selectin ligand, including PCLP, CEA, and CD44v at least about 5, at least about 10, at least about 100, at least about $10^3$, at least about $10^4$, at least $10^5$, and at least $10^6$ fold higher than to other proteins.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a P-sheet configuration, connected by three hypervariable regions, which form loops connecting, and in some cases forming part of, the P-sheet structure. The hypervariable regions in each chain are held together in close proximity by the FRs and, with the hypervariable regions from the other chain, contribute to the formation of the antigen-binding site of immunoglobulins. Kabat et al., SEQUENCES OF PROTEINS OF IMMUNOLOGICAL INTEREST (1991). The constant domains are not involved directly in binding an antibody to an antigen, but exhibit various effector functions, such as participation of the antibody in antibody dependent cellular cytotoxicity (ADCC).

The term "hypervariable region" refers to the amino acid residues of an immunoglobulin that are responsible for antigen-binding. The hypervariable region comprises amino acid residues from a "complementarity determining region" or "CDR" and/or those residues from a "hypervariable loop." "Framework" or "FR" residues are those variable domain residues other than the hypervariable region residues as herein defined. An antibody "which binds" an antigen of interest, e.g., PCLP, CEA, or CD44v, is one capable of binding that antigen with sufficient affinity and/or avidity such that the antibody is useful as a diagnostic or therapeutic agent for targeting a cell expressing the antigen.

The present invention contemplates the use of selectin ligand antibodies or functional equivalents thereof, in the treatment and prevention of cancer. In one embodiment, the selectin ligand antibodies or functional equivalents thereof specifically bind to the extracellular domain of PCLP (amino acids 23-431 of the 528 amino acid protein), CEA (amino acids 35-702 of the 702 amino acid GPI-linked protein), and/or CD44v (amino acids 21-649 of the 742 amino acid protein). In a specific embodiment, an antibody or functional equivalent thereof specifically binds an epitope of the extracellular domain of PCLP, CEA, or CD44v as expressed in a cancer cell. In a more specific embodiment, an antibody or functional equivalent thereof specifically binds a carbohydrate epitope of the extracellular domain of PCLP, CEA, or CD44v as expressed in a cancer cell. General methods for the production of antibodies that specifically bind to particular epitopes of the extracellular domain of transmembrane proteins are known in the art. See, e.g., U.S. Pat. Nos. 6,344,339; 6,218,516; and 6,150,508.

Commercially Available Antibodies

Commercially available antibodies specific for PCLP, CEA, and CD44v may be used in a targeting composition of the present invention. For example, anti-PCLP antibody is available from Santa Cruz Biotechnology, Inc. (Santa Cruz, Calif.) (Clone 3D3, Catalog No. sc-23904). Anti-CEA antibodies are available from BD Biosciences (San Jose, Calif.) (Clone Col-I, Catalog No. 551477) and Abeam, Inc. (Cambridge, Mass. (Catalog No. abl 7254). Anti-CD44v antibodies are available from AbD Serotec (Oxford, United Kingdom) (CD44v3, Clone VFF-327, Catalog No. MCAI 734), (CD44v4, Clone 1 ODl, Catalog No. MCA1970), (CD44v5, Clone VFF-8, Catalog No MCA1729), (CD44v6, Clone VFF-7, Catalog #MCA1730), (CD44v7, Clone VFF-9, Catalog No MCA1731), (CD44v7/8, Clone VFF-17 Catalog No. MCA1732), and (CD44c10, Clone VFF-14, Catalog No. MCA1 733).

Polyclonal Antibodies

Polyclonal antibodies are preferably raised in animals by multiple subcutaneous (sc), intraperitoneal (ip) or intramuscular (im) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl2, or RIN=C—NR, where R and RI are different alkyl groups. Animals are immunized against the antigen, immunogenic conjugates, or derivatives by combining, e.g., 100 pg of the protein or conjugate (for rabbits or mice, respectively) with 3 volumes of Freund's complete adjuvant and injecting the solution intradermally at multiple sites. One month later the animals are boosted with ⅕ to {fraction (1/10)} the original amount of peptide or conjugate in Freund's complete adjuvant by subcutaneous injection at multiple sites. Seven to 14 days later, the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. In addition, aggregating agents such as alum are suitably used to enhance the immune response.

Monoclonal Antibodies

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants, each monoclonal antibody is directed against a single determinant on the antigen. In addition to their specificity, monoclonal antibodies are advantageous in that they may be synthesized while uncontaminated by other immunoglobulins. For example, the monoclonal antibodies to be used in accordance with the invention may be produced by the hybridoma method first described by Kohler et al., 256 NATURE 495 (1975). Alternatively, monoclonal antibodies may be produced by recombinant DNA methods. See, e.g., U.S. Pat. No. 4,816,567. In another embodiment, monoclonal antibodies may be isolated from phage antibody libraries using the techniques described, for example, in Clackson et al., 352 NATURE 624-28 (1991) and in Marks et al., 222 J. MOL. BIOL. 581-97 (1991).

Human Antibodies

As an alternative to humanization, human antibodies may be generated. For example, transgenic animals (e.g., mice) may be produced that are capable, upon immunization, of producing a full repertoire of human antibodies in the absence of endogenous immunoglobulin production. It has been described that the homozygous deletion of the antibody heavy-chain joining region (JH) gene in chimeric and germ-line mutant mice results in complete inhibition of endogenous antibody production. Transfer of the human germ-line immunoglobulin gene in such germ-line mutant mice will result in the production of human antibodies upon antigen challenge. See, e.g., Jakobovits et al., 90 PROC. NATL. ACAD. SCI. USA 2551 (1993); Jakobovits et al., 362 NATURE 255-58 (1993); Bruggermann et al., 7 YEAR IN IMMUNOL. 33 (1993); U.S. Pat. Nos. 5,591,669; 5,589, 369; 5,545,807.

Alternatively, phage display technology may be used to produce human antibodies and antibody fragments in vitro, from immunoglobulin variable (V) domain gene repertoires from unimmunized donors. See, e.g., Johnson and Chiswell, 3 CURRENT OPIN. IN STRUCT. BIOL. 564-71 (1993); McCafferty et al., 348 NATURE 552-53 (1990). According to this technique, antibody V domain genes are cloned in-frame into either a major or minor coat protein gene of a filamentous bacteriophage, such as M13, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display may be performed in a variety of formats. Human antibodies may also be generated by in vitro activated B cells. See U.S. Pat. Nos. 5,567,610 and 5,229, 275.

Humanized Antibodies

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody.

In general, the humanized antibody may comprise substantially all of at least one, and typically two, variable domains, in which all or substantially all of the hypervariable loops correspond to those of a non-human immunoglobulin and all or substantially all of the FRs are those of a human immunoglobulin sequence. In one embodiment, humanized antibodies comprise a humanized FR that exhibits at least 65% sequence identity with an acceptor (non-human) FR, e.g., murine FR. The humanized antibody also may comprise at least a portion of an immunoglobulin constant region (Fe), particularly a human immunoglobulin. For further details, see Jones et al., 321 NATURE 522-25 (1986); Riechmann et al., 332 NATURE 323-29 (1988); Presta, 2 CURR. OPIN. STRUCT. BIOL. 593-96 (1992); WO 01/27160.

Methods for humanizing non-human antibodies have been described in the art. A humanized antibody may have one or more amino acid residues introduced into it from a source which is non-human. These non-human amino acid residues are often referred to as "import" residues, which are typically taken from an "import" variable domain. Humanization may be essentially performed following the method of Winter and co-workers (Jones et al., 321 NATURE 522-25 (1986); Riechmann et al., 332 NATURE 323-27 (1988); Verhoeyen et al., 239 SCIENCE 1534-36 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al., 151 J. IMMUNOL. 2296 (1993); Chothia et al., 196 J. MOL. BIOL. 901 (1987)). Another method uses a particular framework region derived from the consensus sequence of all human antibodies of a particular subgroup of light or heavy chains. The same framework may be used for several different humanized antibodies (Carter et al., 89 PROC. NATL. ACAD. SCI. USA 4285 (1992); Presta et al., 151 J. IMMUNOL. 2623 (1993)).

Importantly, antibodies may be humanized to retain and/or enhance affinity for the antigen and other favorable biological properties. In one embodiment, humanized antibodies maybe designed by analyzing the parental sequences and various conceptual humanized products using three dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this regard, FR residues may be selected and combined from the recipient and import sequences so that the desired antibody characteristic, such as increased affinity for the target antigen(s), is achieved.

Other methods generally involve conferring donor CDR binding affinity onto an antibody acceptor variable region framework. One method involves simultaneously grafting and optimizing the binding affinity of a variable region binding fragment. Another method relates to optimizing the binding affinity of an antibody variable region. See generally WO 01/27160.

The proteins discussed herein, particularly immunoglobulins and more particularly, humanized antibodies, may be rendered non-immunogenic, or less immunogenic, to a given species by identifying in the amino acid sequences one or more potential epitopes for T-cells of the given species and modifying the amino acid sequence to eliminate at least one of the T-cell epitopes. This procedure eliminates or reduces the immunogenicity of the protein when exposed to the immune system of the given species. Indeed, monoclonal antibodies and other immunoglobulin-like molecules can particularly benefit from being de-immunized in this way, for example, mouse-derived immunoglobulins can be de-immunized for human therapeutic use in treating cancers. See WO 98/52976.

Furthermore, certain epitopes may be retained in a protein sequence if the peptides constituting such epitopes are present in endogenous human protein, because they would be recognized as "self". It has now been found, however, that even self-epitopes may give rise to immune reactions. Thus, one aspect of the invention provides for the elimination of self-epitopes, for example, by recombinant DNA technology, to render them more useful for administration to humans, for example for therapeutic or diagnostic purposes relating to cancer. See WO 00/34317.

Therapeutic selectin ligand-binding immunoglobulins or antibodies can also be "chimeric" in the sense that a variable region can come from a one species, such as a rodent, and the constant region can be from a second species, such as a human. See U.S. Pat. No. 6,331,415.

Human, humanized, chimeric, or non-human antibodies can also be subject to affinity maturation. A library of mutant antibody chains based on a previously identified PCLP, CEA, and/or CD44v antibody heavy and light chains is generated, and then screened for changes in activity. Screens can be designed to identify mutants with enhanced activity, including higher affinity, lower dissociation constant, less cross reactivity with other proteins, or stronger effector functions. Examples of a process of generating such a library and identifying antibodies with high affinity are disclosed in WO 01/27160.

Antibody Fragments

"Antibody fragments" comprise a portion of an intact antibody, preferably the antigen-binding or variable region thereof. Examples of antibody fragments include Fab, Fab', F(ab')$_2$, Fv fragments, diabodies, linear antibodies, single-chain antibody molecules, and multispecific antibodies formed from antibody fragments.

Papain digestion of antibodies produces two identical antigen-binding fragments, called "Fab" fragments, each with a single antigen-binding site, and a residual "Fc" fragment. The Fab fragments also contain the constant domain of the light chain and the first constant domain (CHI) of the heavy chain.

Pepsin treatment yields an F(ab')$_2$ fragment that has two antigen-binding sites and is still capable of crosslinking antigen. Fab' fragments differ from Fab fragments by the addition of a few residues at the carboxy terminus of the heavy chain CHI domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are well known in the art.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "scFv" antibody fragments comprise the VH and VL domains of antibody, wherein these domains are present in a single polypeptide chain. The Fv polypeptide may further comprise a polypeptide linker between the VH and VL domains that enables the scFv to form the desired structure for antigen binding. See Pluckthun, 113 THE PHARMACOLOGY OF MONOCLONAL ANTIBODIES 269-315 (Rosenburg and Moore eds. 1994). See also WO 93116185; U.S. Pat. Nos. 5,587,458 and 5,571,894.

Various techniques have been developed for the production of antibody fragments. Traditionally, these fragments were derived via proteolytic digestion of intact antibodies. See, e.g., Morimoto et al., 24 J. BIOCHEM. BIOPHYS. METH. 107-17 (1992); Brennan et al., 229 SCIENCE 81 (1985). However, these fragments may now be produced directly by recombinant host cells. For example, the antibody fragments may be isolated from the antibody phage libraries discussed above. Alternatively, Fab'-SH fragments may be directly recovered from $E.$ $coli$ and chemically coupled to form $F(ab')_2$ fragments. Carter et al., 10 BIO/TECHNOLOGY 163-67 (1992)). In another approach, $F(ab')_2$ fragments may be isolated directly from recombinant host cell culture. Other techniques for the production of antibody fragments will be apparent to the skilled practitioner.

Bispecific Antibodies

The term "bispecific antibody" refers to small antibody fragments with two antigen-binding sites. Each fragment comprises a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen binding sites. EP 0 404 097; WO 93/11161; Hollinger et al., 90 PROC. NATL. ACAD. SCI. USA 6444-48 (1993).

Methods for making bispecific antibodies are well known in the art. Traditional production of full length bispecific antibodies is based on the coexpression of two immunoglobulin heavy chain-light chain pairs, where the two chains have different specificities. Millstein et al., 305 NATURE 537-39 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually accomplished by affinity chromatography steps, is rather cumbersome, and the product yields are low. See also WO 93/08829; Traunecker et al., 10 EMBO J. 3655-59 (1991).

In another approach, antibody variable domains with the desired binding specificities (antibody-antigen combining sites) may be fused to immunoglobulin constant domain sequences. Specifically, the variable domains are fused with an immunoglobulin heavy chain constant domain, comprising at least part of the hinge, CH2, and CH3 regions. In one embodiment, the fusion protein comprises the first heavy-chain constant region (CHI) because it contains the site necessary for light chain binding. Polynucleotides encoding the immunoglobulin heavy chain fusions and, if desired, the immunoglobulin light chain, may be inserted into separate expression vectors and co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

Recent progress has facilitated the direct recovery of Fab'-SH fragments from $E.$ $coli$, which may be chemically coupled to form bispecific antibodies. Shalaby et al., 175 J. EXP. MED. 217-225 (1992) describe the production of a fully humanized bispecific antibody F(ab')2 molecule. Each Fab' fragment was separately secreted from $E.$ $coli$ and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Bispecific antibodies have been produced using leucine zippers. Kostelny et al., 148(5) J. IMMUNOL. 1547-53 (1992). The leucine zipper peptides from the Fos and Jun proteins are linked to the Fab' portions of two different antibodies by gene fusion. The antibody homodimers are then reduced at the hinge region to form monomers and then re-oxidized to form the antibody heterodimers. This method may also be utilized for the production of antibody homodimers.

Another strategy for making bispecific antibody fragments by the use of single-chain Fv (sFv) dimers has also been reported. See Gruber et al., 152 J. IMMUNOL. 5368 (1994). Furthermore, the invention contemplates antibodies with more than two valencies, such as trispecific antibodies. See Tutt et al., 147 J. IMMUNOL. 60 (1991).

Modifications of Antibodies to Selectin Ligands

Peptide Mimetics

Another embodiment for the preparation of antibodies according to the invention is the use of peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993). The underlying rationale behind the use of peptide mimetics in rational design is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used to engineer second generation molecules having many of the natural properties of the targeting antibodies disclosed herein, but with altered and even improved characteristics. More specifically, under this rational design approach, peptide mapping may be used to determine "active" antigen recognition residues, and along with molecular modeling and molecular dynamics trajectory analysis, peptide mimic of the antibodies containing antigen contact residues from multiple CDRs may be prepared.

Epitopes of Selectin Ligands

In some embodiments, the anti-PCLP antibody, anti-CEA antibody, and the anti-CD44v antibody specifically binds an epitope of the respective selectin ligand that maps to a peptide region from the extracellular domain. It is to be understood that the peptide regions may not necessarily precisely map one epitope, but may also contain selectin ligand sequence that is not immunogenic. Methods of predicting other potential epitopes to which an immunoglobulin of the invention can bind are well-known to those of skill in the art and include, without limitation, Kyte-Doolittle Analysis (Kyte, J. and Dolittle, R. F., J. Mol. Biol. (1982)

157:105-132), Hopp and Woods Analysis (Hopp, T. P. and Woods, K. R., Proc. Natl. Acad. Sci. USA (1981) 78:3824-3828; Hopp, T. J. and Woods, K. R., Mol. Immunol. (1983) 20:483-489; Hopp, T. J., J. Immunol. Methods (1986) 88:1-18), Jameson-Wolf Analysis (Jameson, B. A. and Wolf, H., Comput. Appl. Biosci. (1988) 4: 181-186), and Emini Analysis (Emini, E. A., Schlief, W. A., Colonno, R. J. and Wimmer, E., Virology (1985) 140:13-20).

Other Modifications

Amino acid sequence variants of the antibodies of the present invention may be prepared by introducing appropriate nucleotide changes into the polynucleotide that encodes the antibody or by peptide synthesis. Such modifications include, for example, deletions from, and/or insertions into and/or substitutions of, residues within the amino acid sequences of the antibody. Any combination of deletions, insertions, and substitutions may be made to arrive at the final construct.

Amino acid sequence insertions include amino-terminal and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody of a polypeptide that increases the serum half-life of the antibody.

Another type of antibody variant is an amino acid substitution variant. These variants have at least one amino acid residue in the antibody molecule replaced by a different residue. For example, the sites of greatest interest for substitutional mutagenesis of antibodies include the hypervariable regions, but framework region (FR) alterations are also contemplated.

A useful method for the identification of certain residues or regions of the anti-selectin ligand antibodies (including antibodies specific for PCLP, CEA, and CD44v) that are preferred locations for substitution, i.e., mutagenesis, is alanine scanning mutagenesis. See Cunningham & Wells, 244 SCIENCE 1081-85 (1989). Briefly, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. The amino acid locations demonstrating functional sensitivity to the substitutions are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis may be conducted at the target codon or region and the expressed antibody variants screened for the desired activity.

Substantial modifications in the biological properties of the antibody can be accomplished by selecting substitutions that differ significantly in their effect on, maintaining (i) the structure of the polypeptide backbone in the area of the substitution, for example, as a sheet or helical conformation, (ii) the charge or hydrophobicity of the molecule at the target site, or the bulk of the side chain. Naturally occurring residues are divided into groups based on common side-chain properties:

hydrophobic: norleucine, met, ala, val, leu, ile;
(2) neutral hydrophilic: cys, ser, thr;
acidic: asp, glu;
basic: asn, gln, his, lys, arg;
residues that influence chain orientation: gly, pro; and
aromatic: trp, tyr, phe.

Non-conservative substitutions will entail exchanging a member of one of these classes for another class. Conservative substitutions involve exchanging of amino acids within the same class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability, particularly where the antibody is an immunoglobulin fragment such as an Fv fragment.

Another type of substitutional variant involves substituting one or more hypervariable region residues of a parent antibody. Generally, the resulting variant(s), i.e., functional equivalents as defined above, selected for further development will have improved biological properties relative to the parent antibody from which they are generated. A convenient way for generating such substitutional variants is by affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed.

In order to identify candidate hypervariable region sites for modification, alanine-scanning mutagenesis may be performed to identify hypervariable region residues contributing significantly to antigen binding. Alternatively, or additionally, it may be beneficial to analyze a crystal structure of the antibody-antigen complex to identify contact points between the antibody and antigen. Such contact residues and neighboring residues are candidates for substitution according to the techniques elaborated herein. Once generated, the panel of variants is subjected to screening as described herein and antibodies with superior properties in one or more relevant assays may be selected for further development.

It may be desirable to modify the antibodies of the present invention, i.e., create functional equivalents, with respect to effector function, e.g., so as to enhance antigen-dependent cell-mediated cytotoxicity (ADCC) and/or complement dependent cytotoxicity (CDC) of the antibody. This may be achieved by introducing one or more amino acid substitutions in an Fc region of an antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). Caron et al., 176 J. EXP MED. 1191-95 (1992); Shopes, 148 J. IMMUNOL. 2918-22 (1992). Homodimeric antibodies with enhanced anti-tumor activity may also be prepared using heterobifunctional cross-linkers as described in Wolff et al., 53 CANCER RESEARCH 2560-65 (1993). Alternatively, an antibody can be engineered which has dual Fc regions and may thereby have enhanced complement lysis and ADCC capabilities. Stevenson et al., 3 ANTI-CANCER DRUG DESIGN 219-30 (1989).

To increase the serum half-life of an antibody, one may incorporate a salvage receptor binding epitope into the antibody (especially an immunoglobulin fragment) as described in, for example, U.S. Pat. No. 5,739,277. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Polynucleotide molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site directed) mutagenesis, PCR mutagenesis, and cassette mutagenesis of an earlier prepared variant or a non-variant version of the anti-selectin ligand antibodies of the present invention.

Solid Substrates

The targeting compositions of the present invention may comprise a solid substrate. The substrates described herein may be present in a dry formulation (such as lyophilized composition) or the substrate may comprise a particle suspended in a biocompatible medium. Suitable biocompatible media include, but are not limited to, water, deionized water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

In other embodiments, the substrate particle may comprise a nanoparticle, a quantum dot, a liposome, a micelle, a polymersome, or other delivery compositions known in the art.

According to the present invention, in one embodiment, a substrate particle may be conjugated to at least one antibody. In a specific embodiment, a substrate particle may be conjugated to at least one anti-PCLP antibody. In another embodiment, a substrate particle may be conjugated to at least one anti-CEA antibody. In yet another embodiment, a substrate particle may be conjugated to at least one anti-CD44v antibody. In a further embodiment, a substrate particle may be conjugated to at least one anti-PCLP antibody and at least one anti-CEA antibody. In an alternative embodiment, a substrate particle may be conjugated to at least one anti-PCLP antibody and at least one anti-CD44v antibody. The substrate particle may also be conjugated to at least one anti-CEA antibody and at least one anti-CD44v antibody. In a further embodiment, the substrate particle may be conjugated to at least one anti-PCLP antibody, at least one anti-CEA antibody, and at least one anti-CD44v antibody.

Nanoparticles

The nanoparticle substrates of the present invention may be prepared using conventional methods known to those of ordinary skill in the art. For example, in certain embodiments, the nanoparticle substrate may comprise a polymeric matrix or "nanospheres" where the antibody composition is attached, directly or indirectly, to the surface of the nanoparticle substrate. In other embodiments, the nanoparticle substrate may comprise a reservoir system comprising an oily core surrounded by a thin polymeric wall ("nanocapsules"), where the core comprises the antibody composition which may protrude through the wall or be released and function as intended. Polymers suitable for the preparation of nanoparticles include, but are not limited to, poly(alkyl-cyano-acrylates), and polyesters such as poly(lactic acid) (PLA), poly(glycolic acid), poly(-capro-lactone) and their copolymers.

Nanoparticles may be fabricated using biodegradable polyesters, e.g., polymers of poly(lactic acid) (PLA) and copolymers that are manufactured with varying quantities of glycolic acid (PLGA). PLA is more hydrophobic in comparison to PLGA; therefore, PLA offers a relatively extended release profile. Similarly, the ratio of glycolic acid to lactic acid in the copolymerization process affects the degradative properties of the resultant copolymer. In one embodiment, low molecular weight (14 kDa) PLGA may be copolymerized with a high (50%) glycolide content (PLGA 50:50). These particles will degrade comparatively rapidly due to the low molecular weight and high glycolide content of the PLGA used. To obtain nanoparticles with an intermediate or long degradation profile, the formulation may comprise a higher molecular weight copolymer (e.g., 60-100 kDa), with or without a lower glycolide content (PLGA 65:35 or 75:25). In short, a comprehensive range of PLA and PLGA polymer molecular weight, lactic/glycolic acid ratios, and PLA-PLGA blends may be used to optimize loading and release profiles.

Furthermore, nanoparticles (NPs) may comprise a metal, a semiconductor, and an insulator particle compositions, and a dendrimer (organic or inorganic). Thus, nanoparticles are contemplated for use in the methods which comprise a variety of inorganic materials including, but not limited to, metals, semi-conductor materials or ceramics as described in U.S. Patent Publication No 20030147966. Ceramic nanoparticle materials include, but are not limited to, brushite, tricalcium phosphate, alumina, silica, and zirconia. Organic materials from which nanoparticles are produced include carbon. Nanoparticle polymers include polystyrene, silicone rubber, polycarbonate, polyurethanes, polypropylenes, polymethylmethacrylate, polyvinyl chloride, polyesters, polyethers, and polyethylene. Biodegradable, biopolymer (e.g. polypeptides such as BSA, polysaccharides, etc.), other biological materials (e.g. carbohydrates), and/or polymeric compounds are also contemplated for use in producing nanoparticles.

In one embodiment, the nanoparticle is metallic, and in various aspects, the nanoparticle is a colloidal metal. Thus, in various embodiments, nanoparticles useful in the practice of the methods include metal (including for example and without limitation, gold, silver, platinum, aluminum, palladium, copper, cobalt, indium, nickel, or any other metal amenable to nanoparticle formation), semiconductor (including for example and without limitation, CdSe, CdS, and CdS or CdSe coated with ZnS) and magnetic (for example, ferromagnetite) colloidal materials. Other nanoparticles useful in the practice of the invention include, also without limitation, ZnS, ZnO, Ti, $TiO_2$, Sn, $SnO_2$, Si, $SiO_2$, Fe, $Fe^{+4}$, Ag, Cu, Ni, Al, steel, cobalt-chrome alloys, Cd, titanium alloys, AgI, AgBr, HgI.sub.2, PbS, PbSe, ZnTe, CdTe, $In_2S_3$, $In_2Se_3$, $Cd_3P_2$, $Cd_3As_2$, InAs, and GaAs. Methods of making ZnS, ZnO, $TiO_2$, AgI, AgBr, Hgh, PbS, PbSe, ZnTe, CdTe, $In_2S_3$, $In_2Se_3$, $Cd_3P_2$, $Cd_3As_2$, InAs, and GaAs nanoparticles are also known in the art. See, e.g., Weller, 32 CHEM. INT. ED. ENGL. 41 (1993); Henglein, 143 TOP. CURR. CHEM 113 (1988); Henglein, 89 CHEM. REV. 1861 (1989); 53 BRUS, APPL. PHYS. A. 465 (1991); Bahncmann, in Photochemical Conversion and Storage of Solar Energy (eds. Pelizetti and Schiavello 1991), page 251; Wang and Herron, 95 J. PHYS. CHEM. 525 (1991); Olshavsky, et al., 112 J. AM. CHEM. Soc. 9438 (1990); Ushida et al., 95 J. PHYS. CHEM. 5382 (1992).

Methods of making metal, semiconductor and magnetic nanoparticles are well-known in the art. See, for example, Schmid, G. (ed.) Clusters and Colloids (VCH, Weinheim, 1994); Hayat, M. A. (ed.) Colloidal Gold: Principles, Methods, and Applications (Academic Press, San Diego, 1991); Massart, R., IEEE Transactions On Magnetics, 17, 1247 (1981); Ahmadi, T. S. et al., Science, 272, 1924 (1996); Henglein, A. et al., J. Phys. Chem., 99, 14129 (1995); Curtis, A. C., et al., Angew. Chem. Int. Ed. Engl., 27, 1530 (1988). Preparation of polyalkylcyanoacrylate nanoparticles prepared is described in Fatal, et al., J. Controlled Release (1998) 53: 137-143 and U.S. Pat. No. 4,489,055. Methods for making nanoparticles comprising poly(D-glucaramidoamine)s are described in Liu, et al., J. Am. Chem. Soc. (2004) 126:7422-7423. Preparation of nanoparticles comprising polymerized methylmethacrylate (MMA) is described in Tondelli, et al., Nucl. Acids Res. (1998) 26:5425-5431, and preparation of dendrimer nanoparticles is described in, for example Kukowska-Latallo, et al., Proc. Natl. Acad. Sci. USA (1996) 93:4897-4902 (Starburst polyamidoamine dendrimers).

Suitable nanoparticles are also commercially available from, for example, Ted Pella, Inc. (gold), Amersham Corporation (gold) and Nanoprobes, Inc. (gold). Also as described in US Patent Publication No. 20030147966, nanoparticles comprising materials described herein are available commercially or they can be produced from progressive nucleation in solution (e.g., by colloid reaction), or by various physical and chemical vapor deposition processes, such as sputter deposition. See, e.g., HaVashi, (1987) Vac. Sci. Technol. July/August 1987, A5(4):1375-84; Hayashi, (1987) Physics Today, December 1987, pp. 44-60; MRS Bulletin, January 1990, pp. 16-47.

As further described in US Patent Publication No. 20030147966, nanoparticles contemplated are produced using $HAuCl_4$ and a citrate-reducing agent, using methods known in the art. See, e.g., Marinakos et al., (1999) Adv. Mater. 11: 34-37; Marinakos et al., (1998) Chem. Mater. 10: 1214-19; Enustun & Turkevich, (1963) J. Am. Chem. Soc. 85: 3317. Tin oxide nanoparticles having a dispersed aggregate particle size of about 140 nm are available commercially from Vacuum Metallurgical Co., Ltd. of Chiba, Japan. Other commercially available nanoparticles of various compositions and size ranges are available, for example, from Vector Laboratories, Inc. of Burlingame, Calif.

Nanoparticles may be prepared using an emulsification and solvent evaporation process, or so-called double emulsion process, for example. Other procedures comprise adding additional polymers through covalent modification of existing nanoparticles. To form a primary emulsion, an internal aqueous phase that contains a stabilizing emulsifier and an antibody composition is added to an ice-cold organic phase. The stabilizing emulsifier may be 10% w/v polyvinyl alcohol (PVA), and the organic phase may comprise a polymer dissolved in dichloromethane (DCM). The polymer content is modified according to the particle size required.

The surface of hydrophobic nanoparticles may be modified to minimize phagocytosis, allowing sustained systemic circulation of nanoparticles. Following intravenous administration, hydrophobic nanoparticles are rapidly cleared from systemic circulation by the mononuclear phagocytic system (MPS), resulting in rapid deposition of nanoparticles in the liver or spleen. When the liver, spleen or MPS itself are not targets of choice, various modifications of the nanoparticle surface are possible to minimize phagocytosis, including modification with poly(ethylene glycol) (PEG). PEG is a hydrophilic, nonionic polymer that exhibits excellent biocompatibility. PEG molecules, like other polymers, can be added to the nanoparticles by a number of different methods, including covalent bonding, blending during nanoparticle preparation, or surface adsorption. The presence of PEG on the nanoparticle surface serves other functions besides increasing residence time in systemic circulation. PEG has been shown to reduce protein and enzyme adsorption to the nanoparticle, retarding degradation of PLGA-based nanoparticles. The density and molecular weight of PEG on the surface can be adjusted to minimize protein adsorption. Poloxamer and poloxamines also have been shown to reduce nanoparticle capture by macrophages and increase nanoparticle residence time in systemic circulation. PLGA particles also may be coated with poloxamer 407 and poloxamine 908 to extend the half-life of the nanoparticles. Poly(ethylene glycol) can be introduced at the surface either (a) by adsorption of surfactants (e.g., poloxamer 188) or (b) as block or branched co-polymers, usually based on polyesters, such as poly(lactic acid) (PLA).

Quantum Dots

In certain embodiments of the present invention, a particle may comprise a quantum dot. Quantum dots are a semiconductor nanocrystal with size-dependent optical and electronic properties. Many semiconductors that are constructed of elements from groups II-VI, III-V and IV of the periodic table have been prepared as quantum sized particles, exhibit quantum confinement effects in their physical properties, and can be used in the composition of the present invention. Exemplary materials suitable for use as quantum dots include ZnS, ZnSe, ZnTe, CdS, CdSe, CdTe, GaN, GaP, GaAs, GaSb, InP, InAs, InSb, AlS, AlP, AlAs, AlSb, PbS, PbSe, Ge, and Si and ternary and quaternary mixtures thereof. The quantum dots may further include an overcoating layer of a semiconductor having a greater band gap.

The quantum dots are characterized by their uniform nanometer size. By "nanometer" size, it is meant less than about 150 angstroms, including in the range of 12-150 angstroms. The quantum dots also may be substantially monodisperse within the broad range given above. By monodisperse, as that term is used herein, it is meant a colloidal system in which the suspended particles may have substantially identical size and shape. For the purposes of the present invention, monodisperse particles mean that at least about 50% of the particles fall within a specified particle size range. Monodisperse particles may deviate less than about 10% in rms diameter, and in some embodiments, less than about 5% in rms diameter.

Liposomes

In one aspect, the particles of the present invention may comprise a liposome. The liposomes in the composition can be comprised primarily of one or more vesicle-forming lipids. Such a vesicle-forming lipid is one which can form spontaneously into bilayer vesicles in water, as exemplified by the phospholipids, with its hydrophobic moiety in contact with the interior, hydrophobic region of the bilayer membrane, and its head group moiety oriented toward the exterior, polar surface of the membrane.

Liposomes can be categorized into multilamellar vesicles, multivesicular liposomes, unilamellar vesicles and giant liposomes. Multilamellar liposomes (also known as multilamellar vesicles or "MLV") contain multiple concentric bilayers within each liposome particle, resembling the "layers of an onion". Multivesicular liposomes consist of lipid membranes enclosing multiple non-concentric aqueous chambers. Unilamellar liposomes enclose a single internal aqueous compartment. Single bilayer (or substantially single bilayer) liposomes include small unilamellar vesicles (SUV) and large unilamellar vesicles (LUV). LUVs and SUVs range in size from about 50 to 500 nm and 20 to 50 nm respectively. Giant liposomes typically range in size from 5000 nm to 50,000 nm and are used mainly for studying mechanochemical and interactive features of lipid bilayer vesicles in vitro. Needham et al., 18 COLLOIDS AND SURFACES B: BIOINTERFACES 183-195 (2000).

Any suitable vesicle-forming lipid may be utilized in the practice of this invention as judged by one of skill in the art. This includes phospholipids such as phosphatidylcholine (PC), phosphatidylglycerol (PG), phosphatidylinositol (PI), phosphatidic acid (PA), phosphatidylethanolamine (PE) and phosphatidylserine (PS); sterols such as cholesterol; glycolipids; sphingolipids such as sphingosine, ceramides, sphingomyelin, and glycosphingolipids (such as cerebrosides and gangliosides). Suitable phospholipids may include one or two acyl chains having any number of carbon atoms, between about 6 to about 24 carbon atoms, selected independently of one another and with varying degrees of unsaturation. Thus, combinations of phospholipid of different species and different chain lengths in varying ratios may be selected. Mixtures of lipids in suitable ratios, as judged by one of skill in the art, may also be used.

Liposomes for use in the present invention may be generated using a variety of conventional techniques. These techniques include: the ether injection method (Deamer et al., 308 ACAD. SCI. 250 (1978); the surfactant method (Brunner et al., 455 BIOCHIM. BIOPHYS. ACTA 322 (1978); the Cat fusion method (Paphadjopoulos et al., 394 BIOCHIM. BIOPHYS. ACTA 483 (1978); the freeze-thaw method (Pick et al., 212 ARACH. BIOCHIM. BIOPHYS. 186 (1981); the reverse-phase evaporation method (Szoka et al., 601 BIOCHIM. BIOPHYS. ACTA 559 (1981); the ultrasonic treatment method (Huang et al., 8 BIOCHEMISTRY 344 (1969); the ethanol injection method (Kremer et al., 16 BIOCHEMISTRY 3932 (1977); the extrusion method (Hope et al., 812 BIOCHIM. BIOPHYSICA ACTA 55 (1985); the French press method (Barenholz et al., 99 FEBS LETT. 210 (1979); or any other technique described herein or known in the art.

Liposomes may range from any value between about 1 nm to about 100 um in diameter. For example, liposomes in a liposomal composition according to the invention may range from any value between about 10 to about 200 nm in diameter. In some embodiments, liposomes in a iposomal composition according to the invention may be less than about 200 nm in diameter, or less than about 160 nm in diameter, or less than about 140 nm in diameter. In some embodiments, liposomes in a liposomal composition according to the invention may be substantially uniform in size, for example, 10% to 100%, or more generally at least 10%, 20%, 30%, 40%, 50, 55% or 60%, or at least 65%, 75%, 80%, 85%, 90%, or 95%, or as much as 96%, 97%, 98%, 99%, or 100% of the liposomes in the liposomal composition may be between the size values indicated herein. Liposomes may be sized by extrusion through a filter (e.g., a polycarbonate filter) having pores or passages of the desired diameter.

The liposomes can also include a lipopolymer, i.e., a lipid covalently attached to a hydrophilic polymer. Lipopolymers, in particular mPEG-DSPE conjugates, have been used extensively in various liposomal delivery systems. See Woodle, M. C. in POLY(ETHYLENE GLYCOL) CHEMISTRY AND BIOLOGICAL APPLICATIONS; and J. M. Harris and S. Zalipsky, Eds., ACS Symp. Series 680, pp. 60-81, American Chemical Soc., Washington, D.C. (1997). As has been described, for example in U.S. Pat. No. 5,013,556, including such a polymer-derivatized lipid in the liposome composition forms a surface coating of hydrophilic polymer chains around the liposome. The surface coating of hydrophilic polymer chains is effective to increase the in vivo blood circulation lifetime of the liposomes when compared to liposomes lacking such a coating. Polymer-derivatized lipids comprised of methoxy(polyethylene glycol) (mPEG) and a phosphatidylethanolamine (e.g., dimyristoyl phosphatidylethanolamine, dipalmitoyl phosphatidylethanolamine, distearoyl phosphatidylethanolamine (DSPE), or dioleoyl phosphatidylethanolamine) can be obtained from Avanti Polar Lipids, Inc. (Alabaster, Ala.) at various mPEG molecular weights (350, 550, 750, 1000, 2000, 3000, 5000 Daltons). Lipopolymers of mPEG-ceramide can also be purchased from Avanti Polar Lipids, Inc. Preparation of lipid-polymer conjugates is also described in the literature, see U.S. Pat. Nos. 5,631,018, 6,586,001, and 5,013,556; Zalipsky, S., et al., 8 BIOCONJUGATE CHEM. 111 (1997); Zalipsky, S., et al., 387 METH. ENZYMOL. 50 (2004). These lipopolymers can be prepared as well-defined, homogeneous materials of high purity, with minimal molecular weight dispersity (Zalipsky, S., et al., 8 BIOCONJUGATE CHEM. 111 (1997); Wong, J., et al., 275 SCIENCE 820 (1997)). The lipopolymer can also be a "neutral" lipopolymer, such as a polymer-distearoyl conjugate, as described in U.S. Pat. No. 6,586,001. 134; Zalipsky et al., 353 FEBS LETT. 71 (1994); Zalipsky et. al., 4 BIOCONJUGATE CHEM. 296 (1993); Zalipsky et al., 39 J. CONTROL. REL. 153 (1996); Zalipsky et al., 8(2) BIOCONJUGATE CHEM. 111 (1997); Zalipsky et al., 387 METH. ENZYMOL. 50 (2004). Functionalized polymer-lipid conjugates can also be obtained commercially, such as end-functionalized PEG-lipid conjugates (Avanti Polar Lipids, Inc.). The linkage between the molecule and the liposome polymer can be a stable covalent linkage or a releasable linkage that is cleaved in response to a stimulus, such as a change in pH or presence of a reducing agent.

The liposome composition can also include a cyclodextrin. Cyclodextrins are cyclic oligosaccharides of .alpha.-D-gluco-pyranose and can be formed by the catalytic cyclization of starch. Due to a lack of free rotation about the bonds connecting the glycopyranose units cyclodextrins are toroidal or cone shaped, rather than cylindrical. The cyclodextrins have a relatively hydrophobic central cavity and a hydrophilic outer surface. The hydrophobic cage-like structure of cyclodextrins has the ability to entrap a variety of guest compounds to form host-guest complexes in the solid state and in solution. These complexes are often termed inclusion complexes and the guest compounds are released from the inclusion site. Common cyclodextrins are alpha-, beta-, and gamma-cyclodextrin, which consist of six, seven, or eight glucopyranose units, respectively. Cyclodextrins containing nine, ten, eleven, twelve, and thirteen glucopyranose units are designated delta-, epsilon-, xi-, eta-, and theta-cyclodextrin, respectively.

Micelles

In yet another aspect of the present invention, the substrate particle may comprise a micelle. As used herein, the term "micelle" means a vesicle including a single lipid monolayer encapsulating an aqueous phase. Micelles may be spherical or tubular or wormlike and form spontaneously about the critical micelle concentration (CMC). In general, micelles are in equilibrium with the monomers under a given set of physical conditions such as temperature, ionic environment, concentration, etc.

Formation of a micelle requires the presence of "micelle-forming compounds," which include amphipathic lipids (e.g., a vesicle-forming lipid as described herein or known in the art), lipoproteins, detergents, non-lipid polymers, or any other compound capable of either forming or being incorporated into a monolayer vesicle structure. Thus, a micelle-forming compound includes compounds that are capable of forming a monolayer by themselves or when in combination with another compound, and may be polymer micelles, block co-polymer micelles, polymer-lipid mixed micelles, or lipid micelles. A micelle-forming compound, in an aqueous environment, generally has a hydrophobic moiety in contact with the interior of the vesicle, and a polar head moiety oriented outwards into the aqueous environment. Hydrophilicity generally arises from the presence of functional groups such as hydroxyl, phosphate, carboxyl, sulfate, amino or sulfhydryl groups. Hydrophobicity generally results from the presence of a long chain of aliphatic hydrocarbon groups.

A micelle may be prepared from lipoproteins or artificial lipoproteins including low density lipoproteins, chylomicrons and high density lipoproteins. Artificial lipoproteins may also comprise lipidized protein with targeting capabilities. Uptake of lipoproteins into cell populations may be facilitated by receptors present on the target cells. For instance, uptake of low density lipoproteins into cancerous cells may be facilitated by LDL receptors present on such cells and uptake of chylomicrons and lactosylated high density lipoproteins into hepatocytes may be facilitated by the remnant receptor and the lactosylated receptor respectively.

Micelles for use in the present invention may be generated using a variety of conventional techniques. These techniques include: simple dispersion by mixing in aqueous or hydroalcoholic media or media containing surfactants or ionic substances; sonication, solvent dispersion or any other technique described herein or known in the art. Different techniques may be appropriate depending on the type of micelle desired and the physicochemical properties of the micelle-forming components, such as solubility, hydrophobicity and behavior in ionic or surfactant-containing solutions.

Micelles for use in the present invention may range from any value between about 1 nm to about 1000 µm in diameter. In some embodiments, micelles may be less than about 50 nm in diameter, or less than about 30 nm in diameter, or less than about 20 nm in diameter.

In some embodiments, micelles for use in the present invention may include a hydrophilic polymer-lipid conjugate, as described herein or known in the art. As indicated herein, the term "hydrophilic polymer-lipid conjugate" refers to a lipid, e.g., a vesicle-forming lipid, covalently joined at its polar head moiety to a hydrophilic polymer, and is typically made from a lipid that has a reactive functional group at the polar head moiety in order to attach the polymer. The covalent linkage may be releasable such that the polymer may dissociate from the lipid at for example physiological pH after a variable length of time, such as over several to many hours. Adlakha-Hutcheon et al., 17(8) NAT. BIOTECHNOL. 775-779 (1999). Such conjugates may include any compounds known and routinely utilized in the art of sterically stabilized liposome technology and technologies which are useful for increasing circulatory half-life for proteins, including for example polyethylene glycol (PEG), polyvinyl alcohol, polylactic acid, polyglycolic acid, polyvinylpyrrolidone, polyacrylamide, polyglycerol, or synthetic lipids with polymeric head groups. For example, a distearoyl-phosphatidylethanolamine covalently bonded to a PEG alone, or in further combination with phosphatidylcholine (PC), may be used to produce a micelle according to the invention. The molecular weight of the PEG may be any value between about 500 Daltons to about 10,000 Daltons, inclusive, for example, 1000, 2000, 4000, 6000, 8000, etc.

The CMC of the hydrophilic polymer-lipid conjugate will be dependent on the molecular weight of the PEG as well as the lipid anchor and the added components used when preparing mixed micelles (e.g. PEG modified distearoyl-phosphatidylethanolamine and PC).

Polymersomes

In another aspect, the substrate particle of the present invention may comprise a polymersome. A "polymersome" generally refers to a vesicle which is assembled from polymers or copolymers in aqueous solutions. Polymersomes are composed substantially of synthetic polymers and/or copolymers. Unlike liposomes, a polymersome does not include lipids or phospholipids as its majority component. Consequently, polymersomes can be acoustically, thermally, mechanically, and chemically distinct and, in particular, more durable and resilient than the most stable of lipid vesicles. Polymersomes assemble during processes of lamellar swelling (e.g., by film or bulk rehydration), through an additional phoresis step, or by other known methods. Like liposomes, polymersomes form by "self-assembly," a spontaneous, entropy-driven process of preparing a closed semipermeable membrane. The choice of synthetic polymers, as well as the choice of molecular weight of the polymer, are important. The term "substantially" means that greater than 50 mole percent (%) of the vesicle components are composed of synthetic polymers. If desired, greater than approximately 60%, 70%, 80%, 90%, 95%, or even 100 mole % of the polymersome components are composed of synthetic polymers. Polymersomes may be, for example, supramolecular complexes, stabilized, or otherwise cross-linked.

The polymersomes of the present invention are composed of a class of molecules represented by, but not limited to, block copolymers. For example, one such species is the hydrophilic polyethyleneoxide (EO) linked to hydrophobic polyethylethylene (EE). The synthetic diversity of block copolymers provides the opportunity to make a wide variety of vesicles, of which some embodiments form bilayer membranes with material properties that greatly expand what is currently available from the spectrum of naturally occurring phospholipids.

Because of the self-assembled bilayer membrane's pre-selectivity, materials, (e.g., therapeutic macromolecules) may be "encapsulated" in the aqueous interior or intercalated into the hydrophobic membrane core of the polymersome vesicle. Numerous drug delivery technologies can be developed from such vesicles, owing to the numerous unique features of the bilayer membrane and the broad availability of amphiphiles (e.g., block copolymers).

Alternative Substrates: Antibody Arrays

In another aspect, the substrate of the present invention may comprise a fixed matrix. In a particular embodiment, the fixed matrix may comprise an array or a chip. As used herein, an "array" is a linear or two-dimensional (or three-dimensional) array of preferably discrete regions, each having a defined area, formed on the surface of a solid support. As used herein, an antibody array is an array of antibodies placed on a chip or other surfaces. Because the position of each particular group of antibodies on the array is known, the identities of the target cells and non-target cells can be determined based on their binding to a particular position on the array.

Generally, the array comprises a suitable solid support. By "solid support" or "solid phase support" is meant any material that can be modified to contain discrete individual sites appropriate for the attachment or association of the antibodies and is amenable to at least one detection method.

The solid phase support of the present invention can be of any solid materials and structures suitable for supporting antibody-antigen binding. In one embodiment, the solid phase support comprises at least one substantially rigid surface on which the antibodies can be immobilized and a biological containing target and non-target cells can be probed thereon. The solid supports with which the antibody array elements are stably associated may be fabricated from a variety of materials including, but not limited to, plastics, ceramics, metals, acrylamide, cellulose, nitrocellulose, glass, polystyrene, polyethylene vinyl acetate, polypropylene, polymethacrylate, polyethylene, polyethylene oxide, polysilicates, polycarbonates, Teflon®, fluorocarbons, nylon, silicon rubber, polyanhydrides, polyglycolic acid, polylactic acid, polyorthoesters, polypropylfumerate, collagen, glycosaminoglycans, and polyamino acids. Solid supports may be two-dimensional or three-dimensional in form, such as gels, membranes, thin films, glasses, slides, plates, cylinders, beads, magnetic beads, optical fibers, woven fibers, etc. In particular embodiments, the array is a three-dimensional array. A three-dimensional array may comprise a collection of tagged beads. Each tagged bead has different antibodies attached to it. Tags are detectable by signaling means such as color (Luminex, Illumina) and electromagnetic field (Pharmaseq) and signals on tagged beads can even be remotely detected (e.g., using optical fibers). The size of the solid support can be any of the standard array sizes, useful for protein array technology, and the size may be tailored to fit the particular machine being used to conduct a diagnosis and/or detection method of the present invention.

In a specific embodiment, the solid support and the antibody may be derivatized with chemical functional groups for subsequent attachment of the two. Thus, for example, the array can be derivatized with a chemical functional group including, but not limited to, amino groups, carboxy groups, oxo groups and thiol groups. Using these functional groups, the antibodies can be attached to the solid support using linkers known in the art including, for example, homo- or hetero-bifunctional linkers. In addition, in some cases, additional linkers, such as alkyl groups (including substituted and heteroalkyl groups) may be used.

Arrays comprising discrete regions or spots can by prepared using conventional methods including, but not limited to, microfluidics printing (Rowe et al., 71 ANAL. CHEM. 433-439 (1999) and Bernard et al., 73 Anal. Chem. 8-12 (2001)), microstamping (U.S. Pat. Nos. 5,512,131 and 5,731,152, Martin et al., 14 LANGMUIR 3971-3975 (1998), and MacBeath et al., 289 SCIENCE 1760-1763 (2000)), microcontact printing (PCT Publication WO 96/29629), and electrospray deposition (Morozov et al., 71 Anal. Chem. 1415-1420 (1999) and Moerman et al., 73 ANAL. CHEM. 2183-2189 (2001)). Inkjet printer heads provide another option for patterning molecules, or components thereof, to nanometer or micrometer scale sites on the surface of the substrate or coating formed thereon. See Lemmo et al., 60 ANAL. CHEM. 543-551 (1997); Roda et al., 28 BIOTECHNIQUES 492-496 (2000), and Silzel et al., 44 CLIN. CHEM. 2036-2043 (1998)); and U.S. Pat. Nos. 5,843,767 and 5,837,860. In some cases, commercially available arrayers based on capillary dispensing (OmniGrid™ (Genemachines, Inc. (San Carlos, Calif.)) and High-Throughput Microarrayer from (Intelligent Bio-Instruments (Cambridge, Mass.)) may also be used.

The boundaries between the patches of proteins immobilized on substrate arrays may be integrated as topographic patterns (physical barriers) or surface functionalities with orthogonal wetting behavior (chemical barriers). For instance, walls of substrate material or photoresist may be used to separate some of the patches from some of the others or all of the patches from each other. Alternatively, non-bioreactive organic thin films, such as monolayers, with different wettability may be used to separate patches from one another.

Generally, the dispensing device includes calibrating means for controlling the amount of sample deposition, and may also include a structure for moving and positioning the sample in relation to the support surface. The volume of fluid to be dispensed per antibody in an array varies with the intended use of the array, and available equipment. In particular embodiments, a volume formed by one dispensation is less than about 100 nL, less than about 10 nL, and about 1 nL. Solutions of blocking agents may be applied to the arrays to prevent non-specific binding by non-target cells and other molecules that have not bound to an antibody. Solutions of bovine serum albumin (BSA), polyethylene glycol (PEG), casein, or nonfat milk, for example, may be used as blocking agents to reduce background binding in subsequent assays.

The fixed matrix substrates of the present invention may comprise a plurality of spots or discrete regions of antibodies conjugated to such substrate. The size of the spot or discrete region can be varied and may include, for example, at least about a 10 μm×10 μm square. In certain embodiments, an antibody region may be arranged on an area ranging from about 5 μm×about 5 μm to about 500 μm to about 500 μm. In other embodiments, the area may be greater. More specifically, an antibody region may be arranged on an area of about 15×about 15 μm, about 20 μm×about 20 μm, about 25 μm×about 25 μm, about 35 μm×about 35 μm, about 50 μm×about 50 μm, or more.

The antibody spot may take any shape including, for example, a square, a rectangle, a circle, etc. Any suitable pattern of antibody spots may be used, and the distance between antibody spots may be varied and/or optimized by one of ordinary skill in the art.

Furthermore, the number of antibody molecules bound to a particular spot or region (the antibody density) may range from about 1 molecule per site to about 10,000 antibody molecule per site. In fact, the antibody density may range from about 1 molecule per μm2 to about 10,000 molecules per $\mu m^2$. More specifically, the antibody density may range from about 100 molecules per $\mu m^2$ to about 5000 molecules per $\mu m^2$, from about 200 molecules per $\mu m^2$ to about 1000 molecules per $\mu m^2$. In one specific embodiment, the antibody density may comprise about 200 molecules per $\mu m^2$.

Each spot or site on the substrate array may comprise one type of antibody, for example, a spot comprising only anti-PCLP antibody. Multiple spots of single antibodies may comprise different concentrations or densities of that particular antibody. Such an approach may be utilized as a type of titration to reduce cross-reactivity for selectin ligands that are expressed on normal and cancer target cells.

Alternatively, a region of the array may comprise more than one type of antibody. In a specific embodiment, a spot may comprise anti-PCLP antibody and anti-CEA antibody. In another embodiment, the spot may comprise anti-PCLP antibody and anti-CD44v antibody. In yet another embodiment, the spot may comprise anti-CEA antibody and anti-CD44v antibody. In another specific embodiment, a spot on the array may comprise anti-PCLP antibody, anti-CEA antibody, and anti-CD44v antibody. The multi-antibody spots may be present in different concentrations or densities of the antibodies as well. The methods for creating these types of array are known in the art. See, e.g., Ghosh et al., 24 LANGMUIR 8134-8142 (2008).

Substrate Conjugates

In another aspect, the present invention contemplates the conjugation of several molecules to the solid substrate of the targeting composition. Antibodies, chemotherapeutic agents, imaging agents, etc. may be conjugated to a substrate using conventional methods known to those of ordinary skill in the art.

Antibodies

The antibody compositions of the present invention may be bound to the substrate using known techniques including, but not limited to, by chemical coupling means or by genetic engineering. Covalent conjugates of an antibody and a substrate can be prepared by linking chemical moieties of a substrate to functional groups on amino acid sidechains or at the N-terminus or at the C-terminus of the antibody. The antibody may also be chemically modified with other chemical moieties, such as glycosyl groups, lipids, phosphate, acetyl groups and the like, to facilitate chemical coupling.

To illustrate, there are a large number of chemical cross-linking agents that are known to those skilled in the art. In particular embodiments, the cross-linking agents may comprise heterobifunctional cross-linkers, which can be used to link an antibody and a substrate in a stepwise manner. Heterobifunctional cross-linkers provide the ability to design more specific coupling methods for conjugating to proteins, thereby reducing the occurrences of unwanted side reactions such as homo-protein polymers. A wide variety of heterobifunctional cross-linkers are known in the art. These include, but are not limited to, succinimidyl 4-(N-maleimidomethyl)cyclohexane-1-carboxylate (SMCC), m-maleimidobenzoyl-N-hydroxysuccinimide ester (MBS); N-succinimidyl(4-iodoacetyl)aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio) propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo.

In addition to the heterobifunctional cross-linkers, there exist a number of other cross-linking agents including, but not limited to, homobifunctional and photoreactive cross-linkers. Disuccinimidyl suberate (DSS), bismaleimidohexane (BMH) and dimethylpimelimidate-2 HCl (DMP) are examples of useful homobifunctional cross-linking agents, and bis-[.beta.-(4-azidosalicylamido)ethyl]disulfide (BASED) and N-succinimidyl-6(4'-azido-2'-nitrophenylamino)hexanoate (SANPAH) are examples of useful photoreactive cross-linkers for use in the present invention. For a review of protein coupling techniques, see Means et al., 1 BIOCONJUGATE CHEMISTRY 2-12 (1990).

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pHs are unprotonated and react by nucleophilic attack on NHS or sulfo-NHS esters. This reaction results in the formation of an amide bond, and release of NHS or sulfo-NHS as a by-product.

Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5-7.5) conditions. Halogens (iodoacetyl functions) react with —SH groups at physiological pHs. Both of these reactive groups result in the formation of stable thioether bonds.

A heterobifunctional cross-linker may further comprise a spacer arm or bridge. The bridge is the structure that connects the two reactive ends. The most apparent attribute of the bridge is its effect on steric hindrance. In some instances, a longer bridge can more easily span the distance necessary to link two complex molecules. For instance, SMPB has a span of 14.5 angstroms.

In another aspect of the present invention, antibodies may be used in a "free" state, i.e., without conjugation to a substrate. Such antibodies may be conjugated with a chemotherapeutic agent or an imaging agent including a radioactive isotope. In one embodiment, at least one anti-PCLP antibody may be conjugated to $I^{131}$. In another embodiment, at least one anti-CEA antibody may be conjugated to $I^{131}$. In yet another embodiment, at least one anti-CD44v antibody may be conjugated to $I^{131}$.

Chemotherapeutic Agents

In particular embodiments, the targeting composition of the present invention further comprises at least one chemotherapeutic agent conjugated to a suspendable particle. A "chemotherapeutic agent" is a compound useful in the treatment of cancer. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitroureas such as cannustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromoinycins, dactinomycin, daunorubicin, detorubicin, 6-diazo-5-oxo-L-norleucine, doxorubicin, epirubicin, esorubicin, idambicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone;

mitoxantrone; mopidamol; nitracrine; pentostatin; phenamet; pirarubicin; podophyllinic acid; 2-ethylhydrazide; procarbazine; PSK®; razoxane; sizofrran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; esperamlcms; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4 hydroxytamoxifen, trioxifene, keoxifene, onapristone, and toremifene (Fareston); and anti-androgens such as flutamide, nilutamide, bicalutamide, leuprolide, and goserelin; and pharmaceutically acceptable salts, acids or derivatives of any of the above.

Other Conjugates

The present invention further contemplates the conjugation of therapeutic agents that have nucleolytic activity such as a ribonuclease and a deoxyribonuclease. In addition, a variety of radioactive isotopes are available for the production of targeting compositions. Examples include At222, Ret86, Sm153 Bi212, P32 and radioactive isotopes of Lu. Suitable radioactive isotopes may further include, but are not limited to, $^{211}$astatine, $^{14}$carbon, $^{51}$chromium, $^{36}$chlorine, $^{57}$iron, $^{58}$cobalt, $^{67}$copper, $^{152}$Eu, $^{67}$gallium, $^{3}$hydrogen, $^{123}$iodine $^{131}$iodine, $^{111}$indium, $^{59}$iron, $^{32}$phosphorus, $^{186}$rhenium selenium, $^{35}$sulphur, $^{99}$technicium and/or $^{90}$yttrium.

In yet another aspect of the present invention, the particles of the targeting composition may also be conjugated to a receptor, such as streptavidin, for utilization in tumor pretargeting. Briefly, the composition-receptor conjugate is administered to the patient and unbound conjugate is removed from circulation with a clearing agent. A ligand, such as biotin, which is conjugated to a cytotoxic agent is then administered.

Imaging Agents and Detection

The targeting compositions of the present invention may further comprise an imaging agent. In other embodiments, antibodies and imaging agents may be conjugated together and used as a targeting composition without a solid substrate. Examples of imaging agents include, but are not limited to a radiologic contrast agent, diatrizoic acid sodium salt dihydrate, an iodine-containing agent, a barium-containing agent, a fluorescent imaging agent, Lissamine Rhodamine PE, a stain, a dye, a radioisotope, a metal, a ferromagnetic compound, a paramagnetic compound, gadolinium, a superparamagnetic compound, iron oxide, a diamagnetic compound, and barium sulfate.

More specifically, suitable imaging agents, according to the invention can include, but are not limited to those described by Molecular Probes (Handbook of fluorescent probes and research products), such as Rhodamine, fluorescein, Texas red, Acridine Orange, Alexa Fluor (various), Allophycocyanin, 7-aminoactinomycin D, BOB0-1, BODIPY (various), Calcien, Calcium Crimson, Calcium green, Calcium Orange, 6-carboxyrhodamine 6G, Cascade blue, Cascade yellow, DAPI, DiA, DiD, Dil, DiO, DiR, ELF 97, Eosin, ER Tracker Blue-White, EthD-1, Ethidium bromide, Fluo-3, Fluo4, FM1-43, FM4-64, Fura-2, Fura Red, Hoechst 33258, Hoechst 33342, 7-hydroxy-4-methylcoumarin, Indo-1, JC-1, JC-9, JOE dye, Lissamine rhodamine B, Lucifer Yellow CH, LysoSensor Blue DND-167, LysoSensor Green, LysoSensor Yellow/Blu, Lysotracker Green FM, Magnesium Green, Marina Blue, Mitotracker Green FM, Mitotracker Orange CMTMRos, MitoTracker Red CMXRos, Monobromobimane, NBD amines, NeruoTrace 500/525 green, Nile red, Oregon Green, Pacific Blue. POP-1, Propidium iodide, Rhodamine 110, Rhodamine Red, R-Phycoerythrin, Resorfin, RH414, Rhod-2, Rhodamine Green, Rhodamine 123, ROX dye, Sodium Green, SYTO blue (various), SYTO green (Various), SYTO orange (various), SYTOX blue, SYTOX green, SYTOX orange, Tetramethylrhodamine B, TOT-1, TOT-3, X-rhod-1, YOYO-1, and YOYO-3.

Also included within the scope of the present invention are metal ions generally used for chelation in paramagnetic Tl-type MIR contrast agents, and include di- and tri-valent cations selected from the group consisting of copper, chromium, iron, gadolinium, manganese, erbium, europium, dysprosium and holmium. Metal ions that can be chelated and used for radionuclide imaging according to the invention include, but are not limited to, metals selected from the group consisting of gallium, germanium, cobalt, calcium, indium, iridium, rubidium, yttrium, ruthenium, yttrium, technetium, rhenium, platinum, thallium and samarium. Additionally metal ions known to be useful in neutron-capture radiation therapy include boron and other metals with large nuclear cross-sections. Also included are metal ions useful in ultrasound contrast, and X-ray contrast compositions.

The imaging agent may be conjugated to each of the various substrate particles described herein and within the scope of the present invention using methods known to those of ordinary skill in the art. More specifically, radioactively labeled antibodies of the present invention may be produced according to well-known methods in the art. For instance, they can be iodinated by contact with sodium or potassium iodide and a chemical oxidizing agent such as sodium hypochlorite, or an enzymatic oxidizing agent, such as lactoperoxidase. Antibodies may also be labeled with technetium$^{99}$ by ligand exchange process, for example, by reducing pertechnate with stannous solution, chelating the reduced technetium onto a Sephadex column and applying the peptide to this column or by direct labeling techniques, e.g., by incubating pertechnate, a reducing agent such as SNCh, a buffer solution such as sodium-potassium phthalate solution, and the peptide. Intermediary functional groups which are often used to bind radioisotopes which exist as metallic ions to peptides are diethylenetriaminepentaacetic acid (DTPA) and ethylene diaminetetraacetic acid (EDTA).

In certain embodiments, the antibodies may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277, 437; 4,275,149 and 4,366,241.

Furthermore, in a specific embodiment, quantum dots may be used as an imaging agent itself because of their luminescent properties. In particular, a quantum dot may emit at visible light wavelengths, far-red, near-infrared, and infrared wavelengths, and at other wavelengths, typically in response to absorption below their emission wavelength.

Generally, quantum dots (which may also be referred to interchangeably as a "semiconductor nanocrystal" or a "fluorescent semiconductor nanocrystals") demonstrate quantum confinement effects in their luminescent properties. When quantum dots are illuminated with a primary energy source, a secondary emission of energy occurs of a frequency that corresponds to the band gap of the semiconductor material used in the quantum dot. In quantum confined particles, the band gap is a function of the size of the nanocrystal.

The narrow size distribution of the quantum dots allows the possibility of light emission in narrow spectral widths. Monodisperse quantum dots have been described in detail in Murray et al. (J. Am. Chem. Soc., 115:8706 (1993)); in the thesis of Christopher Murray, "Synthesis and Characterization of II-VI Quantum Dots and Their Assembly into 3-D Quantum Dot Superlattices", Massachusetts Institute of Technology, September 1995; and in U.S. patent application Ser. No. 08/969,302 entitled "Highly Luminescent Color-selective Materials".

The fluorescence of semiconductor nanocrystals results from confinement of electronic excitations to the physical dimensions of the nanocrystals. Quantum dots may have discrete optical transitions, which are tunable with size (U.S. patent application Ser. No. 08/969,302 entitled "Highly Luminescent Color-selective Materials"). Current technology allows good control of their sizes (for example, between about 12 to about 150 angstroms), and thus, enables construction of quantum dots that emit light at a desired wavelength throughout the UV-visible-IR spectrum with a quantum yield ranging from 30-50% at room temperature in organic solvents and 10-30% at room temperature in water.

Quantum dots are capable of fluorescence when excited by light. The ability to control the size of quantum dots enables one to construct quantum dots with fluorescent emissions at any wavelength in the UV-visible-IR region. Therefore, the emissions of quantum dots are tunable to any desired spectral wavelength. Furthermore, the emission spectra of monodisperse quantum dots have linewidths as narrow as 25-30 nm. The linewidths are dependent on the size heterogeneity of quantum dots in each preparation.

The imaging agents of the present invention may be detected using imaging methods and devices known to those of ordinary skill in the art. The particular imaging method and device depends on the type of imaging agent used to image a cancer cell. Imaging methods and devices include, but are not limited to, microscopy, position emission tomography, single photon emission computed tomography (SPECT), radioimaging, fluorescence imaging, color imaging, biophotonic imaging, magnetic resonance imaging (MRI), X-ray, and computer-assisted tomography.

Methods and Composition for Treatment of Cancer

The compositions of the present invention are useful in treating and/or preventing cancer including, but not limited to, lung, colon, liver, prostate, ovarian, breast, brain, thyroid, bone, kidney and skin (e.g., melanoma) cancers, as well as cancers such as leukemia and lymphoma. Further, more specific examples of cancer include, but are not limited to, malignant and non-malignant cell growth, leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), hairy cell leukemia, myelodyplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, pancreatic carcinoma, nasopharyngeal carcinoma, neural blastoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain, and the like.

In a specific embodiment, the methods and compositions of the present invention may be used to treat a primary tumor. In another embodiment, the methods and compositions of the present invention may be used to treat or prevent metastasis. In yet another embodiment, the methods and compositions of the present invention may be used to treat a secondary tumor. In an alternative embodiment, the methods and compositions of the present invention may be used to treat or prevent colon cancer. In a particular embodiment, the methods and compositions of the present invention may be used to treat or prevent pancreatic cancer. In a further embodiment, the methods and compositions of the present invention may be used to treat or prevent neural blastoma. In a specific embodiment, the methods and compositions of the present invention may be used to treat or prevent prostate cancer. In another embodiment, the methods and compositions of the present invention may be used to treat or prevent breast cancer. In several embodiments, the methods and compositions of the present invention may be used to treat or prevent any cancer in which any one or more of PCLP, CEA, or CD44v is expressed on tumor cells.

Routes of Administration

The compositions of the present invention may be administered by any particular route of administration including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means.

Pulmonary/Nasal Administration

There are a several desirable features of an inhalation device for administering a composition of the present invention. For example, delivery by the inhalation device is reliable, reproducible, and accurate. For pulmonary administration, at least one composition may be delivered in a particle size effective for reaching the lower airways of the lung or sinuses. The inhalation device can optionally deliver small dry particles, e.g. less than about 10 µm, including about 1-5 µm, for good respirability.

According to the invention, at least one composition can be delivered by any of a variety of inhalation or nasal devices known in the art for administration of a therapeutic agent by inhalation. Devices capable of depositing aerosolized formulations in the sinus cavity or alveoli of a patient include metered dose inhalers, nebulizers, dry powder generators, sprayers, and the like. Other devices suitable for directing pulmonary or nasal administration are also known in the art.

All such devices can be used for the administration of a composition in an aerosol. Such aerosols may comprise either solutions (both aqueous and non aqueous) or solid particles. Metered dose inhalers like the Ventolin® metered dose inhaler, typically use a propellant gas and require actuation during inspiration. See, e.g., WO 98/35888; WO 94/16970. Dry powder inhalers like Turbuhaler® (Astra), Rotahaler® (Glaxo), Diskus® (Glaxo), Spiros® inhaler (Dura), devices marketed by Inhale Therapeutics, and the Spinhaler® powder inhaler (Fisons), use breath-actuation of a mixed powder. See U.S. Pat. Nos. 5,458,135; 4,668,218; WO 97/25086; WO 94/08552; WO 94/06498; and EP 0 237 507, each entirely expressly incorporated herein by reference. Nebulizers like AERx®, Aradigm, the Ultravent® nebulizer (Mallinckrodt), and the Acom II® nebulizer (Marquest Medical Products), produce aerosols from solutions, while metered dose inhalers, dry powder inhalers, etc., generate small particle aerosols. These specific examples of commercially available inhalation devices are intended to be a representative of specific devices suitable for the practice of the invention, and are not intended as limiting the scope of the invention.

Formulations suitable for nasal administration, wherein the carrier is a solid, include a coarse powder having a particle size, for example, in the range of 0.001 to 5000 µm which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the composition.

A spray comprising a composition of the present invention can be produced by forcing a suspension or solution of a composition disclosed herein through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one composition delivered by a sprayer have a particle size in a range of about less than 1 nm to less than about 200 µm Compositions of the present invention suitable for use with a sprayer typically include a composition disclosed herein in an aqueous solution at a concentration of about 0.0001 µg to about 100 mg of a composition disclosed herein per ml of solution, or any range or value therein, including, but not limited to, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 µg/ml or mg/ml. The composition can include agents such as an excipient, a buffer, an isotonicity agent, a preservative, a surfactant, or other known agents of pharmaceutical compositions.

A composition of the present invention can also be administered by a nebulizer such as a jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation either directly or through a coupling fluid, creating an aerosol including the composition. Advantageously, the pharmaceutical composition delivered by a nebulizer have a particle size range of from about less than 1 nm to less than about 2000 µm.

Compositions of the present invention suitable for use with a nebulizer, either jet or ultrasonic, typically include a concentration of about 0.1 ng to about 100 mg of a composition disclosed herein per ml of solution, or any range or value therein including, but not limited to, the individual amounts disclosed for spray compositions. The composition can include other pharmaceutical agents such as an excipient, a buffer, an isotonicity agent, a preservative, a surfactant, and those known in the art for use in nebulizer administration.

In a metered dose inhaler (MDI), a propellant, a composition of the present invention, and any excipients or other additives are contained in a canister as a mixture including a liquefied, compressed gas. Actuation of the metering valve releases the mixture as an aerosol, preferably containing a particle size range of from about less than 1 nm to less than about 2000 µm.

The desired aerosol particle size can be obtained by employing a formulation of a composition of the present invention produced by various methods known to those of skill in the art including, but not limited to, jet-milling, spray drying, critical point condensation, and the like. Suitable metered dose inhalers include those manufactured by 3M or Glaxo and employing a hydrofluorocarbon propellant.

Compositions for use with a metered-dose inhaler device will generally include a finely divided powder containing a composition disclosed herein as a suspension in a non-aqueous medium, for example, suspended in a propellant with the aid of a surfactant. The propellant can be any conventional material employed for this purpose such as chlorofluorocarbon, a hydrochlorofluorocarbon, a hydrofluorocarbon, or a hydrocarbon including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like. In one embodiment, the propellant is a hydrofluorocarbon. The surfactant can be chosen to stabilize the composition of the present invention as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. One of ordinary skill in the art will recognize that the methods of the present invention can be achieved by pulmonary administration of a composition disclosed herein via devices not described herein.

For absorption through mucosal surfaces, the compositions and methods of the present invention for administering a composition disclosed herein include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles. See, e.g., U.S. Pat. No. 5,514,670. Mucous surfaces suitable for application of the emulsions of the present invention can include corneal, conjunctival buccal, sublingual, nasal, vaginal, pulmonary, abdominal, intestinal, and rectal routes of administration. Compositions for vaginal or rectal administration such as suppositories, can contain as excipients, for example, polyalkyleneglycols, vaseline, cocoa butter, and the like. Compositions for intranasal administration can be solid and contain excipients, for example, lactose or can be aqueous or oily solutions of nasal drops. For buccal administration, excipients include sugars, calcium stearate, magnesium stearate, pregelinatined starch, and the like. See, e.g., U.S. Pat. No. 5,849,695.

Transdermal Administration

In another embodiment, the pharmaceutical compositions of the present invention may be administered via transdermal routes using forms of transdermal skin patches well known to those of ordinary skill in that art. For transdermal administration, a composition of the present invention is encapsulated in a delivery device such as a liposome or polymeric nanoparticles, microparticle, microcapsule, or microspheres (referred to collectively as particles unless otherwise stated). A number of suitable devices are known, including particles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof. See, e.g., U.S. Pat. No. 5,814,599. To be administered in the form of a transdermal delivery system, the dosage administration may be, for example, continuous rather than intermittent throughout the dosage regimen.

Formulations suitable for topical administration to the skin may be presented as ointments, creams, gels and pastes comprising the ingredient to be administered in a pharmaceutical acceptable carrier. A preferred topical delivery system is a transdermal patch comprising a composition of the present invention.

Topical compositions containing a composition of the present invention may be admixed with a variety of carrier materials well known in the art including alcohols, aloe vera gel, allantoin, glycerine, vitamin A and E oils, mineral oil, PPG2 myristyl propionate and the like to form, for example, alcoholic solutions, topical cleansers, cleansing creams, skin gels, skin lotions, and shampoos in cream or gel formulations. Examples of such carriers and methods of formulation may be found in REMINGTON'S PHARMACEUTICAL SCIENCES (1990). Formulations may contain from about 0.001% to about 40% by weight of the active ingredient. In one embodiment, the formulations contain from about 0.001% to 10% by weight of the composition of the present invention.

Compounds of the present invention may be administered by bioactive agent delivery systems containing particles suspended in a polymer matrix. The particles may be microcapsules, microspheres, nanoparticles, nanospheres, etc., currently known in the art. The particles should be capable of being entrained intact within a polymer that is or becomes a gel once inside a biological environment. The particles can be biodegradable or non-biodegradable. Many microencapsulation techniques used to incorporate a bioactive agent into a particle carrier are taught in the art. See, e.g., U.S. Pat. Nos. 4,652,441; 5,100,669; 4,438,253; and 5,665,428.

A polymeric matrix will be biodegradable and exhibit water solubility at low temperature and will undergo reversible thermal gelation at physiological mammalian body temperatures. The polymeric matrix is capable of releasing the composition entrained within its matrix over time and in a controlled manner. The polymers are gradually degraded by enzymatic or non-enzymatic hydrolysis in aqueous or physiological environments. See, e.g., U.S. Pat. No. 6,287,588.

Compounds of the present invention may be administered by a drug delivery composition comprising particles comprising at least one chemotherapeutic agent and an antibody composition suspended in a polymer matrix. The particles may be microcapsules, microspheres, nanoparticles, or nanospheres currently known in the art. The particles should be biodegradable and stable in physiological environments. The particles also permit diffusion of the chemotherapeutic agent from the core through the matrix at a predetermined release rate. Ionic chemotherapeutic agents are suitable for use in the delivery composition of the invention. The drug delivery compositions may be delivered to a target site through a variety of known routes of administration. Dosages of the chemotherapeutic agent incorporated in the targeting composition will depend on individual needs, the desired effect and on the chosen route of administration. See, e.g., WO 98/50018.

Dosage Determinations

In general, the compositions disclosed herein may be used alone or in concert with other therapeutic agents at appropriate dosages defined by routine testing in order to obtain optimal efficacy while minimizing any potential toxicity. The dosage regimen utilizing a composition of the present invention may be selected in accordance with a variety of factors including type, species, age, weight, sex, medical condition of the patient; the severity of the condition to be treated; the route of administration; the renal and hepatic function of the patient; and the particular composition employed. A physician of ordinary skill can readily determine and prescribe the effective amount of the drug required to prevent, counter, or arrest the progress of the condition.

Optimal precision in achieving concentrations of drug within the range that yields maximum efficacy with minimal toxicity may require a regimen based on the kinetics of the composition's availability to one or more target sites. Distribution, equilibrium, and elimination of a drug may be considered when determining the optimal concentration for a treatment regimen. The dosages of a composition disclosed herein may be adjusted when combined to achieve desired effects. On the other hand, dosages of these various therapeutic agents may be independently optimized and combined to achieve a synergistic result wherein the pathology is reduced more than it would be if either agent were used alone.

In particular, toxicity and therapeutic efficacy of a composition disclosed herein may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effect is the therapeutic index and it may be expressed as the ratio $LD_{50}/ED_{50}$. Compositions exhibiting large therapeutic indices are preferred except when cytotoxicity of the composition is the activity or therapeutic outcome that is desired. Although compositions that exhibit toxic side effects may be used, a delivery system can target such compositions to the site of affected tissue in order to minimize potential damage to uninfected cells and, thereby, reduce side effects. Generally, the compositions of the present invention may be administered in a manner that maximizes efficacy and minimizes toxicity.

Data obtained from cell culture assays and animal studies may be used in formulating a range of dosages for use in humans. The dosages of such compositions lies preferably within a range of circulating concentrations that include the $ED_{50}$ with little or no toxicity. The dosage may vary within this range depending upon the dosage form employed and the route of administration utilized. For any composition used in the methods of the invention, the therapeutically effective dose may be estimated initially from cell culture assays. A dose may be formulated in animal models to achieve a circulating plasma concentration range that includes the $IC_{50}$ (the concentration of the test composition that achieves a half-maximal inhibition of symptoms) as determined in cell culture. Such information may be used to accurately determine useful doses in humans. Levels in plasma may be measured, for example, by high performance liquid chromatography.

Moreover, the dosage administration of the compositions of the present invention may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See WO 00/67776, which is entirely expressly incorporated herein by reference.

Dosages

More specifically, the compositions may be administered in a single daily dose, or the total daily dosage may be administered in divided doses of two, three, or four times daily. In the case of oral administration, the daily dosage of the compositions may be varied over a wide range from about 0.1 ng to about 1,000 mg per patient, per day. The range may more particularly be from about 0.001 ng/kg to 10 mg/kg of body weight per day, about 0.1-100 µg, about 1.0-50 µg or about 1.0-20 mg per day for adults (at about 60 kg).

The daily dosage of the pharmaceutical compositions may be varied over a wide range from about 0.1 ng to about 1000 mg per adult human per day. For oral administration, the compositions may be provided in the form of tablets containing from about 0.1 ng to about 1000 mg of the composition or 0.1, 0.2, 0.5, 1.0, 2.0, 5.0, 10.0, 15.0, 100, 150, 200, 250, 300, 350, 400, 450, 500, 550, 600, 650, 700, 800, 900, or 1000 milligrams of the composition for the symptomatic adjustment of the dosage to the patient to be treated. An effective amount of the composition is ordinarily supplied at a dosage level of from about 0.1 ng/kg to about 20 mg/kg of body weight per day. In one embodiment, the range is from about 0.2 ng/kg to about 10 mg/kg of body weight per day. In another embodiment, the range is from about 0.5 ng/kg to about 10 mg/kg of body weight per day. The compositions may be administered on a regimen of about 1 to about 10 times per day.

In the case of injections, it is usually convenient to give by an intravenous route in an amount of about 0.0001 µg-30 mg, about 0.01 µg-20 mg or about 0.01-10 mg per day to adults (at about 60 kg). In the case of other animals, the dose calculated for 60 kg may be administered as well.

Doses of a composition of the present invention can optionally include 0.0001 µg to 1,000 mg/kg/administration, or 0.001 µg to 100.0 mg/kg/administration, from 0.01 µg to 10 mg/kg/administration, from 0.1 µg to 10 mg/kg/administration, including, but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration or any range, value or fraction thereof.

As a non-limiting example, treatment of humans or animals can be provided as a one-time or periodic dosage of a composition of the present invention 0.1 ng to 100 mg/kg such as 0.0001, 0.001, 0.01, 0.1 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Specifically, the compositions of the present invention may be administered at least once a week over the course of several weeks. In one embodiment, the pharmaceutical compositions are administered at least once a week over several weeks to several months. In another embodiment, the pharmaceutical compositions are administered once a week over four to eight weeks. In yet another embodiment, the pharmaceutical compositions are administered once a week over four weeks.

More specifically, the compositions may be administered at least once a day for about 2 days, at least once a day for about 3 days, at least once a day for about 4 days, at least once a day for about 5 days, at least once a day for about 6 days, at least once a day for about 7 days, at least once a day for about 8 days, at least once a day for about 9 days, at least once a day for about 10 days, at least once a day for about 11 days, at least once a day for about 12 days, at least once a day for about 13 days, at least once a day for about 14 days, at least once a day for about 15 days, at least once a day for about 16 days, at least once a day for about 17 days, at least once a day for about 18 days, at least once a day for about 19 days, at least once a day for about 20 days, at least once a day for about 21 days, at least once a day for about 22 days, at least once a day for about 23 days, at least once a day for about 24 days, at least once a day for about 25 days, at least once a day for about 26 days, at least once a day for about 27 days, at least once a day for about 28 days, at least once a day for about 29 days, at least once a day for about 30 days, or at least once a day for about 31 days.

Alternatively, the compositions may be administered about once every day, about once every 2 days, about once every 3 days, about once every 4 days, about once every 5 days, about once every 6 days, about once every 7 days, about once every 8 days, about once every 9 days, about once every 10 days, about once every 11 days, about once every 12 days, about once every 13 days, about once every 14 days, about once every 15 days, about once every 16 days, about once every 17 days, about once every 18 days, about once every 19 days, about once every 20 days, about once every 21 days, about once every 22 days, about once every 23 days, about once every 24 days, about once every 25 days, about once every 26 days, about once every 27 days, about once every 28 days, about once every 29 days, about once every 30 days, or about once every 31 days.

The compositions of the present invention may alternatively be administered about once every week, about once every 2 weeks, about once every 3 weeks, about once every 4 weeks, about once every 5 weeks, about once every 6 weeks, about once every 7 weeks, about once every 8 weeks, about once every 9 weeks, about once every 10 weeks, about once every 11 weeks, about once every 12 weeks, about once every 13 weeks, about once every 14 weeks, about once every 15 weeks, about once every 16 weeks, about once every 17 weeks, about once every 18 weeks, about once every 19 weeks, about once every 20 weeks.

Alternatively, the compositions of the present invention may be administered about once every month, about once every 2 months, about once every 3 months, about once every 4 months, about once every 5 months, about once every 6 months, about once every 7 months, about once every 8 months, about once every 9 months, about once every 10 months, about once every 11 months, or about once every 12 months.

Alternatively, the compositions may be administered at least once a week for about 2 weeks, at least once a week for about 3 weeks, at least once a week for about 4 weeks, at least once a week for about 5 weeks, at least once a week for about 6 weeks, at least once a week for about 7 weeks, at least once a week for about 8 weeks, at least once a week for about 9 weeks, at least once a week for about 10 weeks, at least once a week for about 11 weeks, at least once a week for about 12 weeks, at least once a week for about 13 weeks, at least once a week for about 14 weeks, at least once a week for about 15 weeks, at least once a week for about 16 weeks, at least once a week for about 17 weeks, at least once a week for about 18 weeks, at least once a week for about 19 weeks, or at least once a week for about 20 weeks.

Alternatively the compositions may be administered at least once a week for about 1 month, at least once a week for about 2 months, at least once a week for about 3 months, at least once a week for about 4 months, at least once a week for about 5 months, at least once a week for about 6 months, at least once a week for about 7 months, at least once a week for about 8 months, at least once a week for about 9 months, at least once a week for about 10 months, at least once a week for about 11 months, or at least once a week for about 12 months.

Kits

The present invention also provides kits for use in treating and/or diagnosing cancer. The kits of the present invention include one or more containers comprising targeting compositions (or unit dosage forms and/or articles of manufacture), and in some embodiments, further comprise instructions for use in accordance with any of the methods described herein. The kit may further comprise a description of selecting an individual suitable or treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

In some embodiments, the kit comprises a) a targeting composition comprising a solid substrate, an antibody composition, and optionally a chemotherapeutic agent, and b) instructions for administering the targeting composition for treatment of a proliferative disease such as cancer.

The kits of the present invention are in suitable packaging. Suitable packaging include, but is not limited to, vials, bottles, jars, flexible packaging (e.g., sealed Mylar or plastic bags), and the like. Kits may optionally provide additional components such as buffers and interpretative information.

The instructions relating to the use of the compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of the composition as disclosed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compositions and instructions for use and packaged in quantities sufficient for storage and use in pharmacies, for example, hospital pharmacies and compounding pharmacies. Without further elaboration, it is believed that one skilled in the art, using the preceding description, can utilize the present invention to the fullest extent. The following examples are illustrative only, and not limiting of the remainder of the disclosure in any way whatsoever.

EXAMPLES

Materials and Methods

Adhesion Molecules. Antibodies and Reagents.

The chimeric form of E- and P-selectin-IgG Fc (E-selectin; P-selectin) consisting of the lectin, epidermal growth factor and consensus repeat domains for human E-selectin and P-selectin, respectively, linked to each arm of human IgGi, were obtained from Wyeth External Research (Cambridge, Mass.). Somers et al., 103 CELL 467-479 (2000). L-selectin-IgG Fc (L-selectin) was purchased from R&D Systems (Minneapolis, Minn.). Anti-PCLP mAb 3D3 was from Santa Cruz Biotechnology Inc. (Santa Cruz, Calif.). Fluorescein isothiocyanate (FITC)-conjugated anti-PCLP antibody 53Dll and isotype control were from MBL International (Woburn, Mass.). Alkaline phosphatase (AP)- and Horseradish peroxidase (HRP)-conjugated anti-mouse IgG and AP-conjugated anti-rat IgM were from Southern Biotech (Birmingham, Ala.). All other unlabeled and phycoerythrin (PE)- or FITC-conjugated antibodies were obtained from BD Biosciences Pharmingen (San Jose, Calif.) unless otherwise specified. All other reagents were from Sigma (St. Louis, Mo.) unless otherwise stated.

Cell Culture.

The human colorectal carcinoma cell line LSI 74T was obtained from the American Type Culture Collection (Manassas, Va.), and cultured in the recommended medium. Prior to cell lysis, LS 174T carcinoma cells were detached from culture flasks using Enzyme Free Cell Dissociation Media (15 min at 37° C.; Chemicon, Phillipsburg, N.J.). Napier et al., 282 J. BIOL. CHEM. 3433-3441 (2007). For flow cytometric and flow-based adhesion assays, LS174T cells were harvested by mild trypsinization (0.25% trypsin/EDTA for 5 min at 37° C.), and subsequently incubated (107 cells/ml) at 37° C. for 2 h to allow regeneration of surface glycoproteins. Burdick et al., 287 AM. J. PHYSIOL. CELL PHYSIOL. C539-547 (2004); Mannori et al., 55 CANCER RES. 4425-4431 (1995); and McCarty et al., 96 BLOOD 1789-1797 (2000). CHO cells, stably transfected with cDNA encoding full-length E-selectin (CHO-E) or with the phosphatidylinositol glycan-linked extracellular domain of P-selectin (CHO-P), were kindly donated by Affymax (Palo Alto, Calif.), and processed as previously described. Hanley et al., 65 CANCER RES. 5812-5817 (2005); Napier et al., 282 J. BIOL. CHEM. 3433-3441 (2007). Cell lines were routinely checked and confirmed to be negative for mycoplasma infection. Jadhav et al., 167 J. IMMUNOL. 5986-5993 (2001).

Colon Carcinoma Cell Lysis and Immunoprecipitation Assays.

Whole cell lysate was prepared by membrane disruption using 2% NP-40 followed by differential centrifugation. Aigner et al., 89 BLOOD 3385-3395 (1997); and Hofmann et al., 51 CANCER RES. 5292-5297 (1991). PCLP was immunoprecipitated from colon carcinoma cell lysate with an anti-PCLP mAb, 3D3, using recombinant Protein G agarose beads (Invitrogen, Carlsbad, Calif.). Hanley et al., 20 FASEB J. 337-339 (2006); Napier et al., 282 J. BIOL. CHEM. 3433-3441 (2007); and Thomas et al., 283 J BIOL CHEM 15647-15655 (2008). In view of immunoblot assays showing that LS174T cells do not express CD66d, CEA (CD66e) and CD66c were immunoprecipitated from LS174T colon carcinoma cell lysate with an anti-CD66de mAb, Col-1, and an anti-CD66c mAb, B6.2, respectively, using recombinant Protein G agarose beads (Invitrogen, Carlsbad, Calif.).

Purification and Mass Spectrometry Analysis of 180 kDa.

HECA-452-Reactive LS174T Protein. The putative selectin ligands corresponding to the HECA-452-reactive 180-kDa protein was isolated by performing affinity chromatography on the whole cell lysate of CD44-knockdown LS I 74T cells using KappaLock™ agarose supports (Invitrogen, Carlsbad, Calif.) crosslinked with bis(sulfosuccinimidyl) suberate (BS3 (Pierce Biotechnology, Rockford, Ill.) to HECA-452 mAb. Thomas et al., 283 J BIOL CHEM 15647-15655 (2008). Eluted proteins were then separated by SDS-PAGE and stained in gel with ProQ Emerald 300 glycoprotein stain (Invitrogen), which only binds to carbohydrate groups at glycosylation sites, thereby leaving the polypeptide core intact. Thomas et al., 283 J BIOL CHEM I 5647-I 5655 (2008). The stained band at 180-kDa was then excised and trypsin-digested gel fragments were submitted for analysis by nano-flow HPLC interfaced to electrospray ionization tandem mass spectrometry (HPLC-MS/MS) using a ThermoFinnigan LTQ mass spectrometer. Id. The MS data were searched against all taxonomies in the NCBI non-redundant protein database with a 95% significance threshold ($p<0.05$) using Mascot (Matrix Science) and with a $p<0.01$ confidence using the BioWorks 3.3 software featuring the SEQUEST algorithm (ThermoFinnigan).

SDS-PAGE and Western Blotting.

Whole cell lysate or immunopurified PCLP or CD66e was diluted with reducing sample buffer, and separated using 4-20% SDS-PAGE gels (Bio-Rad Laboratories, Hercules, Calif.). Napier et al., 282 J. BIOL. CHEM. 3433-3441 (2007). Resolved proteins were transferred to Sequi-blot or Immun-blot polyvinylidene difluoride (PVDF) and blocked with StartingBlock (Pierce Biotechnology, Rockford, Ill.) for 15 min. Immunoblots were stained with HECA-452, MECA-79, anti-PCLP (3D3), anti-CD66de (Col-I), or anti-CD66c (B6.2) mAbs, and rinsed with TBS/O. I % Tween 20. Subsequently, blots were incubated with appropriate AP- or HRP-conjugated secondary antibodies. Western Blue AP substrate (Promega, Madison, Wis.) and SuperSignal West Pico Chemiluminescent Substrate (Pierce Biotechnology, Rockford, Ill.) were used to develop the AP- and HRP-conjugated antibody-stained immunoblots, respectively.

Blot Rolling Assay.

Blots of immunopurified PCLP or CD66e from wild-type or CD44-knockdown LS174T whole cell lysate were stained with anti-PCLP (3D3), anti-CD66de (Col-I), anti-CD66c, or HECA-452 mAbs, and rendered translucent by immersion in 90% D-PBS/10% glycerol. Fuhlbrigge et al., I 68 J. IMMUNOL. 5645-5651 (2002). The blots were placed under a parallel-plate flow chamber, and human peripheral blood lymphocytes or CHO transfectants, re-suspended at $5 \times 10^6$ cells/ml in 90% D-PBS/I 0% glycerol, were perfused at the shear stress of 0.5 dyn/cm$^2$. Hanley et al., 20 FASEB J. 337-339 (2006); Napier et al., 282 J. BIOL. CHEM. 3433-3441 (2007); and Thomas et al., 283 J BIOL CHEM 15647-15655 (2008). Molecular weight markers were used as guides to aid placement of the flow chamber over stained bands of interest. The number of interacting cells per lane was averaged over 10× fields of view (0.55 mm$^2$ each) for 5 min within each stained region. Non-specific adhesion was assessed by perfusing 5 mM EDTA in the flow medium.

Preparation of PCLP-Coated and CD66e-Coated Microspheres.

Immunoprecipitated PCLP or CD66e from wild-type or CD44-knockdown LS 174T whole cell lysate was diluted to desired concentrations with binding buffer (0.2 M carbonate/bicarbonate buffer, pH 9.2), and incubated with 10 μm polystyrene microspheres ($2.5 \times 10^7$ microspheres/ml; Polysciences Inc., Warrington, Pa.) overnight at 4° C. with constant rotation. Hanley et al., 20 FASEB J. 337-339 (2006); Napier et al., 282 J. BIOL. CHEM. 3433-3441 (2007); and Thomas et al., 283 J BIOL CHEM 15647-15655 (2008). Microspheres were washed 2× with D-PBS, and subsequently blocked with D-PBS/1% BSA for 30 min at RT. Microspheres were resuspended ($2 \times 10^6$ microspheres/ml) in D-PBS/0.1% BSA for use in flow cytometric and flow chamber assays. Site densities of PCLP-coated microspheres were determined by flow cytometry. Hanley et al., 20 FASEB J. 337-339 (2006); Napier et al., 282 J. BIOL. CHEM. 3433-3441 (2007); and Thomas et al., 283 J BIOL CHEM 15647-15655 (2008).

Enzymatic Treatments.

To remove terminal sialic acid residues, wild-type LS174T PCLP-coated or CD66e-coated microspheres were incubated with 0.1 U/ml *Vibrio cholerae* sialidase (Roche Molecular Biochemicals) for 90 min at 37° C. Hanley et al., 20 FASEB J. 337-339 (2006); Napier et al., 282 J. BIOL. CHEM. 3433-3441 (2007). In select experiments, PCLP-coated microsphere suspensions ($5 \times 106$ microspheres/ml) were incubated for 2 h at 37° C. with 120 mg/ml of 0-sialoglycoprotein endopeptidase (OSGE; Accurate Chemical & Scientific, Westbury, N.Y.) to specifically cleave glycoproteins with O-glycosylation on serine and threonine residues. Hanley et al., 117 J CELL SCI. 2503-2511 (2004). To cleave N-glycans from CD66e, LS174T whole cell lysate was pretreated with 8 U/ml N-glycosidase F (EMD Biosciences, San Diego, Calif.) for 48 h at 37° C., as described previously before immunoprecipitation. Hanley, et al., 20(2) FASEB J. 20(2), 337-339 (2006); and Napier, et al., 282(6) J. BIOL. CHEM. 3433-3441 (2007). Site densities of PCLP or CD66e adsorbed onto microspheres following enzymatic treatments were determined by flow cytometry before use in flow-based adhesion assays.

Inhibitor Treatments.

Prior to metabolic inhibitor studies, LS174T cell suspensions ($10^7$ cells/ml) were pre-treated with 0.1 U/ml *Vibrio cholerae* sialidase for 60 min at 37° C. to remove terminal sialic acid residues, and ensure de nova synthesis of newly generated HECA-452 reactive carbohydrate structures. Hanley et al., 20 FASEB J. 337-339 (2006); and Napier et al., 282 J. BIOL. CHEM. 3433-3441 (2007). Complete removal of sialylated structures was confirmed via flow cytometry using the mAb HECA-452 that recognizes sialic acid-bearing epitopes. Subsequently, LS174T cells were cultured for 48 h at 37° C. in medium containing either 2 mM benzyl-2-acetamido-2-deoxy-a-D-galactopyranoside (benzyl-GalNAc) to inhibit O-linked glycosylation, or 1 mM deoxymannojirimycin (DMJ) to disrupt N-linked processing. Hanley et al., 20 FASEB J. 337-339 (2006); and Napier et al., 282 J. BIOL. CHEM. 3433-3441 (2007). D-PBS diluting was used for control untreated cells.

Flow Cytometry.

PCLP, CD66e, CD66c, and HECA-452 site densities on microspheres were quantified by single-color immunofluorescence and flow cytometry (FACSCalibur, BD Biosciences) using FITC-conjugated anti-PCLP (53Dll), PE-conjugated antiCD66 (Bl.I), anti-CD66c (B6.2), or HECA-452 mAbs. Similarly, PCLP expression by colon carcinoma cells was monitored by using the FITC-conjugated anti-PCLP antibody 53D11. CEACAM expression on colon carcinoma cells was studied by using primary anti-CD66 mAbs (CD66a, GM8G5; CD66b, 80H3; CD66c, 9A6; CD66de, Col-1; CD66f, BAP3; CEACAM7, BAC2) with appropriate PE-conjugated secondary and isotype control antibodies. Background levels were determined by incubating cell or microsphere suspensions with properly matched FITC-conjugated isotype control antibodies. Hanley et al., 20 FASEB J. 337-339 (2006); and Napier et al., 282 J. BIOL. CHEM. 3433-3441 (2007).

Flow-Based Adhesion Assays.

To simulate the physiological shear environment of the vasculature, PCLP-coated or CD66e-coated microspheres suspended in D-PBS/0.1% BSA were perfused over immobilized IgG- or E-, L- or P-selectin-coated dishes at prescribed wall shear stresses using a parallel-plate flow chamber (250 μm channel depth, 5.0 mm channel width). Hanley et al., 20 FASEB J. 337-339 (2006); and Napier et al., 282 J. BIOL. CHEM. 3433-3441 (2007). The extent of adhesion was quantified by perfusing cells/microspheres at $1 \times 10^6$/ml and enumerating the total number of tethering events in a single 10× field of view during a 2 min period. Average rolling velocities were computed as the distance traveled by the centroid of the translating cell/microsphere divided by the time interval at the given wall shear stress. Burdick et al., 287 AM. J. PHYSIOL. CELL PHYSIOL. C539-547 (2004); Burdick et al., 284 AM. J. PHYSIOL. CELL PHYSIOL. C977-987 (2003); and McCarty et al., 96 BLOOD 1789-1797 (2000). A minimum of 30 cells was tracked for each condition. In select experiments, PCLP-coated microspheres, wildtype and CD44-knockdown LS174T cells, or CD66e-coated microspheres were perfused over substrates with 5 mM EDTA in the flow medium.

Preparation of CD66e siRNA Oligonucleotides.

Short interfering (si) RNA oligonucleotides targeting CD66e were generated using the WI siRNA design program (Whitehead Institute, Massachusetts Institute of Technology). Napier, et al., 282(6) J. BIOL. CHEM. 3433-3441 (2007). The siRNA sequences were used to construct 60-mer short hairpin (sh)RNA oligonucleotides, which were then synthesized (Operon, Inc., Huntsville, Ala.), and ligated into the pSUPER.puro.gfp expression vector (Oligoengine, Inc, Seattle, Wash.) under the control of the HI promoter. The following oligonucleotide was used (underlined: sense and antisense sequences; bold: restriction enzyme sites; italicized: Pol III termination signal; bold/italicized: loop with linker):

(SEQ ID NO: 5)
(5'-GATCCCCGGACCCTCACTCTATTCAATTCAAGAGATTGAATAGAG
TGAGGGTCCTTTTTC-3').

The ligated product was transformed into competent DH5a E. coli cells, amplified m the presence of ampicillin, and the plasmid was purified using the EndoFree Maxi Kit (Qiagen, Valencia, Calif.). Sequence insertion was verified by restriction digestion, and confirmed by direct sequencing. An empty vector was used as a negative control in all shRNA experiments.

Generation of Stable CD66e-knockdown and CD66e/CD44-double-knockdown Colon Carcinoma Cell Lines. About $8 \times 10^6$ wildtype or CD44-knockdown LS174T cells were plated in 100-mm dishes and grown overnight reaching a 50% confluency. The cells were then transfected with 32 μg of pSUPER.puro.gfp.CD66e using Lipofectamine 2000 for 24 h. Upon reaching confluency, transfected cells were passed and $5 \times 10^6$ cells seeded per Petri dish in growth medium in triplicate. After 24 h, the medium was replaced by a fresh aliquot containing 2.5 μg/ml puromycin. Cells were then grown continually without passaging for 15 days, replenishing the puromycin-containing medium every 2-3 days. Single cell colonies were isolated and cultured using standard techniques.

Statistical Analysis.

Data are expressed as the mean±SEM for at least 3 independent experiments. Statistical significance of differences between means was determined by ANOVA. If means were shown to be significantly different ($p<0.05$), multiple comparisons were performed by the Tukey test.

Example 1

Sialofucosylated PCLP Expressed by LS174T Colon Carcinoma Cells is an E-/L-, but not P-, Selectin Ligand Blot rolling assays revealed the presence of alternative sialofucosylated glycoprotein(s) with an apparent molecular mass of 170-180-kDa, which can mediate selectin binding in CD44-knockdown LS174T colon carcinoma cells. Id. To identify and characterize the putative selectin ligand(s), immunoaffinity chromatography was performed in order to purify the 180-kDa sialofucosylated glycoprotein from whole cell lysates of CD44-knockdown LSI 74T cells using KappaLock™-agarose supports crosslinked with a HECA-452 mAb. See FIG. 1. Eluted proteins were separated by SDS-PAGE and stained in gel using ProQ Emerald 300 glycoprotein stain, which fluorescently labels periodate-oxidized glycans while leaving the polypeptide backbone intact. Alternatively, the proteins were transferred to PVDF membranes and immunoblotted using HECA-452 to confirm the retention of the putative glycoprotein targets throughout purification. This purification process retained the 180 kDa HECA-452-reactive band in both stained gels and western blots. See FIG. 3A. This band was then excised and submitted for HPLC-MS/MS analysis of trypsin-digested fragments. Bioinformatics analysis of the MS data revealed peptide fragment matches for PCLP (podocalyxin-like isoform I precursor, accession number NP_001018121; podocalyxin-like isoform 2 precursor, accession number NP_005388).

Figure 3A:
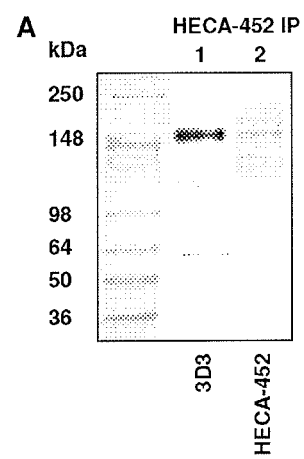
FIGS. 3A-3C provides Western blot results from PCLP experiments. A: Western blots of HECA-452 immunoaffinity product from CD44-knockdown LS174T colon carcinoma cell lysate stained with the anti-PCLP (3D3) (lane 1) or HECA-452 (lane 2) mAbs. Western blots reveal that PCLP is a 180-kDa molecule recovered after HECA-452 immunoaffinity chromatography of CD44-knockdown LS174T whole cell lysate. Panel B: Western blots of whole cell lysate from wild-type (lane I) and CD44-knockdown (lane 2) LSI 74T colon carcinoma cells stained with the anti-PCLP mAB 3D3. Panel C: Western blots of immunoprecipitated PCLP from CD44-knockdown LS174T whole cell lysate stained with the anti-PCLP (3D3) (lane 1) or HECA-452 (lane 2) mAbs demonstrating that PCLP is a 180 kDa sialofucosylated glycoprotein.
Figure 3B:
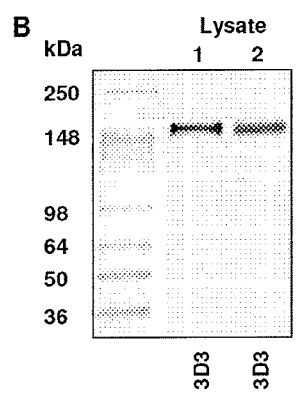
Figure 3C:
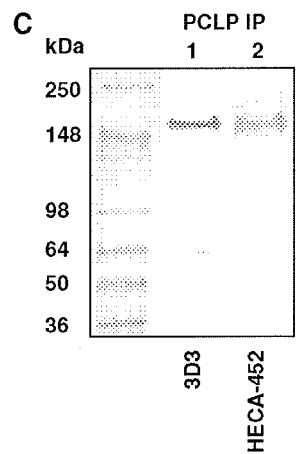

A series of experiments were next performed to validate that PCLP is indeed a selectin ligand in LSI 74T colon carcinoma cells. As a first step, Western blots of HECA-452 immunoaffinity product from CD44-knockdown LS174T cell lysate stained with either an anti-PCLP mAb, 3D3, or HECA-452 mAb revealed that PCLP is an 180-kDa protein recovered by affinity chromatography (FIG. 3A). Immunoblot analysis using an anti-PCLP mAb, 3D3, also disclosed the presence of PCLP with an apparent molecular mass of 180-kDa in whole cell lysates from both wild-type and CD44-knockdown LS174T colon carcinoma cells (FIG. 3B). Using immunopurified PCLP from wild-type (data not shown) and CD44-knockdown LS I 74T cell lysates (FIG. 3C) blotted with HECA-452 mAb, it was demonstrated that PCLP expressed by these cells is sialofucosylated.

Using a blot rolling assay, the ability of immunopurified PCLP to support selectin-dependent adhesion in shear flow was evaluated. To this end, E- and P-selectin-expressing CHO cells as well as L-selectin-expressing human peripheral blood lymphocytes were perfused over the SDS-PAGE resolved immunopurified PCLP protein band from CD44-knockdown LS 174T cells under physiologically relevant levels of shear stress. This assay revealed that E- and L-, but not P-, selectin-expressing cells tethered appreciably over the 180 kDa region (Table 2, below), which corresponds to sialofucosylated PCLP, thereby suggesting that PCLP possesses E-/L-, but not P-, selectin ligand activity.

TABLE 2

E-, P- and L-selectin-dependent adhesion to SDS-PAGE resolved immunopurified PCLP protein band under flow.

| Blot Condition | CHO-E (E-selectin) | CHO-P (P-selectin) | Lymphocyte (L-selectin) |
| --- | --- | --- | --- |
| Immunopurified PCLP | +++++ | – | *** |

E- or P-selectin-expressing CHO cells or L-selectin-expressing peripheral blood lymphocytes were perfused at 0.5 dyn/cm2 over SDS-PAGE immunoblots of immunopurified PCLP from whole cell lysate of CD44-knockdown LS174T colon carcinoma cells. The number of interacting cells per mm2 was quantified over five fields of view surrounding the 180-kDa region that marked the center of the PCLP band. Each "+" represents 50 stationary cells/mm2, while an "*" represents 50 transient tethered/rolling cells/mm2. A "–" indicates no adhesion.

Example 2

PCLP Serves as an Alternative Glycosylation Acceptor on Colon Carcinoma Cells

Figures 4A, 4B:
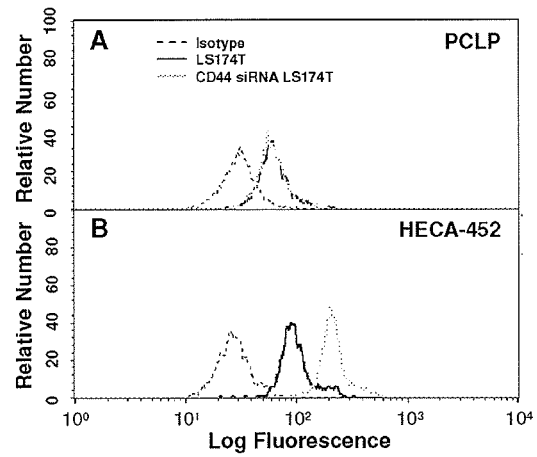
FIGS. 4A-4E presents results from flow-based adhesion assays using PCLP. A and B: Representative flow cytometric histograms of (A) PCLP and (B) HECA-452 expression on microbeads coated with PCLP immunopurified from wild-type (black line) and CD44-knockdown (gray line) LS 174T cells. Microspheres were stained with the FITC-conjugated anti-PCLP mAb 53Dl 1 (A), FITC-conjugated HECA-452 mAb (B), or FITC-conjugated isotype control antibody (dashed lines). C: Extent of adhesion of microbeads ($10^6$/ml) coated with PCLP immunopurified from wild-type or CD44-knockdown LS174T cells over 10 µg/ml E-(black bars), L-(white bars), or P-selectin at a wall shear stress level of 1 dyn/cm$^2$ for 2 min. Data represent the mean±SEM. *p<0.05 with respect to microbeads coated with PCLP immunopurified from wild-type LSI 74T cells. D and E: Average rolling velocities of microspheres ($10^6$/ml) coated with PCLP immunopurified from wild-type or CD44-knockdown LS 174T cells over 10 µg/ml (D) E-selectin or (E) L-selectin over a range of shear stresses. Data represent the mean±SEM. *p<0.05 with respect to microbeads coated with PCLP immunopurified from wild-type LS 174T cells.
Figure 4C:
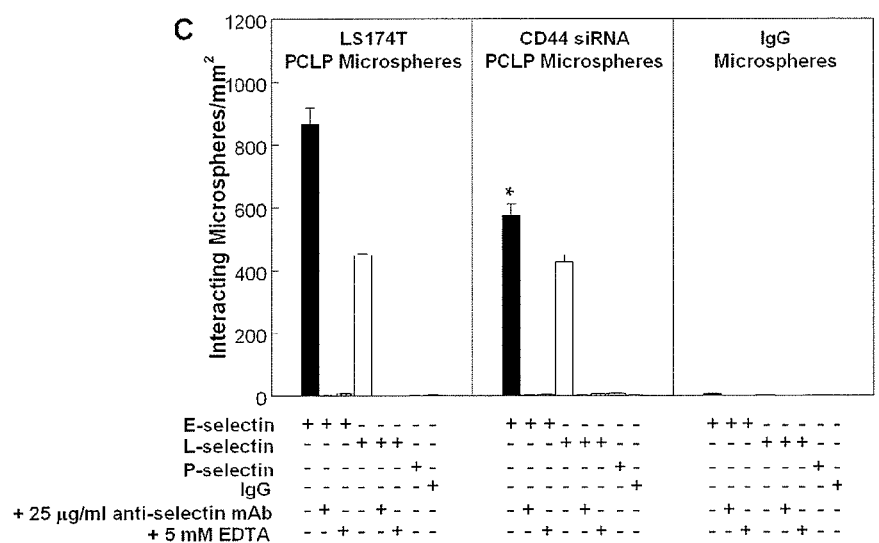
Figure 4D:
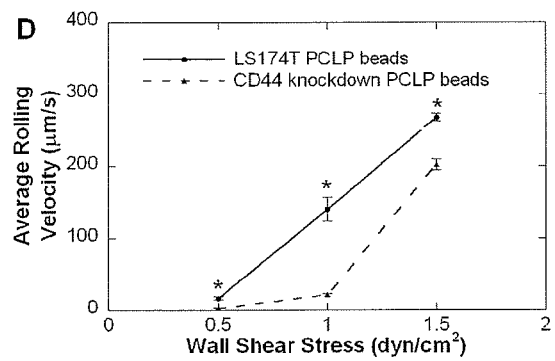
Figure 4E:
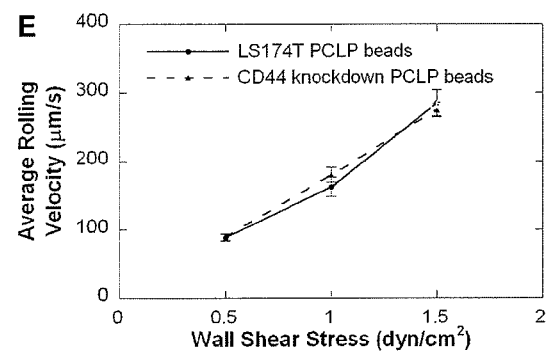

A cell-free flow-based adhesion assay was used to validate that PCLP is an E-/L-, but not P-, selectin ligand, and to compare the adhesion of microbeads coated with PCLP immunoprecipitated from wild-type versus CD44-knockdown LS174T colon carcinoma cells to purified selectin substrates under flow. Burdick et al., 287 AM. J. PHYSIOL. CELL PHYSIOL. C539-547 (2004); Napier et al., 282 J. BIOL. CHEM. 3433-3441 (2007); and Thomas et al., 283 J BIOL CHEM I 5647-15655 (2008). This technique allows quantitative comparisons of PCLP-mediated adhesion to selectin substrates at prescribed PCLP and selectin site densities in shear flow. Burdick et al., 287 AM. J. PHYSIOL. CELL PHYSIOL. C539-547 (2004); Napier et al., 282 J. BIOL. CHEM. 3433-3441 (2007); and Thomas et al., 283 J BIOL CHEM 15647-15655 (2008). By coating microbeads with equivalent levels of PCLP from each cell type (FIG. 4A), it was found that PCLP on CD44-knockdown LS174T cells exhibits higher HECA-452 immunoreactivity than PCLP on wild-type LS174T cells (FIG. 4B), thereby suggesting that PCLP serves as an alternative glycosylation acceptor on colon carcinoma cells. Because sialofucosylated structures are pivotal to selectin binding function (Burdick et al., 284 AM. J. PHYSIOL. CELL PHYSIOL. C977-987 (2003); Simon et al., 7 ANNU REV BIOMED ENG 151-185 (2005); and Varki et al., 100 J CLIN INVEST S31-35 (1997)), it was hypothesized that this difference in biochemical reactivity would directly impact the biophysics of selectin-PCLP interactions. This hypothesis was tested by perfusing PLCP-coated microbeads from each cell type over selectin substrates at a wall shear stress of 1 dyn/cm2. As expected from blot rolling assays, microbeads coated with PCLP from either cell type were capable of tethering and rolling over E- and L-, but not P-, selectin, albeit with varying efficiencies (FIG. 4C). The specificity of PCLP-selectin binding in these assays was disclosed through the use of nonspecific IgG-bearing microbeads and by preincubating the selectin-coated dishes with the respective function-blocking anti-selectin mAb prior to the perfusion of PCLP-coated microbeads. As an additional control, EDTA (5 mM) was added to the perfusion medium in select experiments. In all three control experiments, no microbeads tethered to the selectin substrates in shear flow. It is noteworthy that the extent of interaction of CD44-knockdown LS174T PCLP-decorated microbeads with E-selectin was significantly less than that of microbeads coated with PCLP from wild-type LS174T cells (FIG. 4C). This difference is ascribed to the lower average rolling velocities of the former microbeads (and thus lower number of microspheres entering the field of observation (41)) relative to wild-type LS174T PCLP-coated microspheres over a wide range of wall shear stresses (FIG. 4D). On the other hand, no difference was noted in either the extent of microbead binding (FIG. 4C) or the average rolling velocities (FIG. 4E) of microbead coated with PCLP from either cell type over L-selectin.

Example 3

Figure 5A:
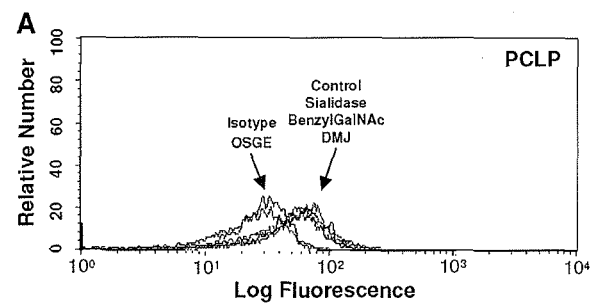
FIGS. 5A-5D shows results from PCLP-coated microsphere and flow cytometry experiments. A and B: Site densities of (A) PCLP and (B) sLex on wild-type LS174T PCLP-bearing polystyrene microbeads, pretreated with enzymes or metabolic inhibitors, determined by flow cytometry. Wild-type LS174T PCLP-absorbed microspheres were treated with *Vibrio cholerae* sialidase (0.1 U/ml) or OSGE (120 µg/ml). In other experiments, microbeads were coated with PCLP immunoprecipitated from wild-type LS174T whole cell lysate pretreated with DMJ or benzyl-GalNAc. Site densities of adsorbed PCLP were quantified using the FITC-conjugated anti-PCLP mAb 53D11. Site densities of HECA-452-reactive epitopes on untreated (control) and treated wild-type LS174T PCLP-coated microbeads were determined by flow cytometry using a HECA-452 mAb. C and D: Extent of adhesion of wild-type LS174T PCLP-coated polystyrene microbeads pretreated with sialidase or microbeads coated with PCLP immunopurified from the whole cell lysate of wild-type LS174T cells cultured in benzyl-GalNAc or DMJ-containing media to 10 µg/ml (C) E-selectin or (D) L-selectin at a wall shear stress level of 1 dyn/cm$^2$ for 2 min. Data represent the mean±SE. *p<0.05 by ANOVA.
Figure 5B:
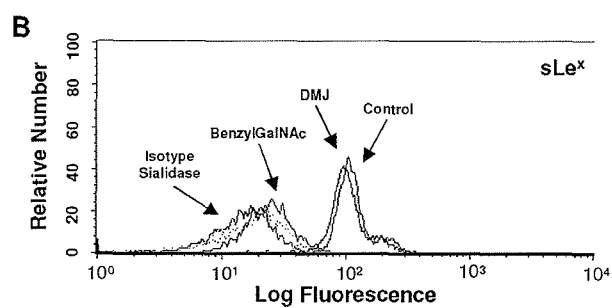
Figure 5C:
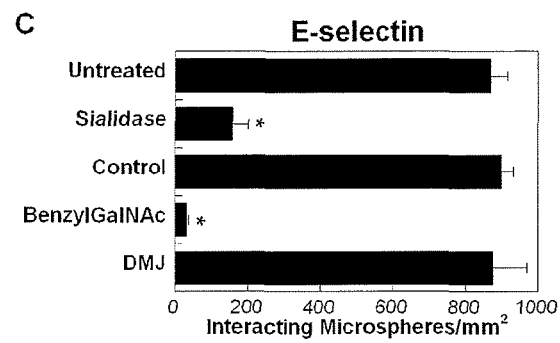

The Selectin Binding Determinants of PCLP are Displayed on Sialofucosylated O-Linked Glycans To characterize the structural linkage-bearing selectin binding determinants on PCLP, PCLP-coated microbeads were treated with highly selective enzymes that cleave specific carbohydrate moieties from the PCLP glycoprotein. Treatment of wild-type LS174T PCLP-coated microbeads with sialidase eliminated HECA-452 reactivity (FIG. 5B) without affecting the PCLP site density on the bead surface (FIG. 5A). This intervention nearly abolished microbead adhesion to L-selectin and reduced binding to E-selectin by 80% (FIG. 5C). It is noteworthy that sialidase treatment converted the remaining interactions between PCLP-bearing microbeads and E-selectin from stable rolling to swift tethers.

To assess the potential contribution of N-linked glycans to PLCP-selectin interactions, microbeads were generated using PCLP immunopurified from LS174T cells cultured for 48 h in medium containing deoxymannojirimycin (DMJ) (1 mM) to disrupt N-linked processing (17, 44). This treatment did not alter the PCLP site density on the bead surface (FIG.

Figure 5D:
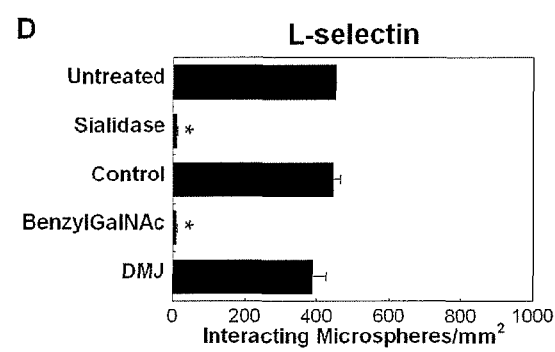

5A) or the HECA-452-reactivity (FIG. 4B), or the extent of bead tethering to E- and L-selectin substrates under flow (FIGS. 5C, 5D).

To determine the potential role of 0-glycans in PCLP-selectin binding, microbeads were prepared using PCLP immunoprecipitated from colon carcinoma cells cultured for 48 h in medium containing 2 mM benzyl-GalNAc to inhibit O-linked glycosylation. Hanley et al., 20 FASEB J. 337-339 (2006); and Napier et al., 282 J. BIOL. CHEM. 3433-3441 (2007). Site densities of adsorbed PCLP were verified by flow cytometry to be similar to those of untreated to controls (FIG. 5A). However, benzyl-GalNAc treatment eliminated HECA-452 reactive epitopes from LS174T PCLP (FIG. 5B), suggesting that the majority of sLex displayed on PCLP are O-linked glycans. Moreover, PCLP-coated microspheres from benzyl-GalNAc-treated LS174T cells bound minimally to E- and L-selectin in shear flow (FIG. 5D), suggesting that the selectin-binding determinants on PCLP from LS174T colon carcinoma cells are sialofucosylated structures displayed on O-linked glycans. The presence of a high level of O-linked glycans on the LS174T PCLP is further substantiated by the fact that enzymatic treatment of PCLP-bearing microbeads with OSGE completely eliminated PCLP detection on the bead surface by flow cytometry (FIG. 5A).

Prior work suggested that PCLP on HEVs is a MECA-79-reactive (sulfated glycan) L-selectin ligand. Sassetti et al., 187 J EXP MED 1965-1975 (1998). To determine whether PCLP on colon carcinoma cells is MECA-79-reactive, immunopurified PCLP from wild-type LS174T cells was resolved by SDS-PAGE and stained with MECA-79 via Western blotting. Surprising, in contrast to PCLP expressed by HEVs as reported previously (Id.), PCLP expressed by LS 174T colon carcinoma cells is not MECA-79-reactive (data not shown).

Example 4

Identification of CEA as an E- and L-Selectin Ligand Expressed by Wildtype and CD44-Knockdown LS174T Colon Carcinoma Cells The presence of a 170-180 kDa sialofucosylated glycoprotein(s) in CD44-knockdown LS174T colon carcinoma cells that was capable of mediating selectin binding under flow was identified. Napier, et al., 282(6) J. BIOL. CHEM. 3433-3441 (2007). To delineate the identity of the selectin ligand(s), the putative target was purified from CD44-knockdown LS174T colon carcinoma cell lysates by affinity chromatography using KappaLock™ agarose beads coated with a HECA-452 mAb (FIG. 1), which detects sialofucosylated epitopes. Eluted samples were separated by SDS-PAGE and immunoblotted with HECA-452 to confirm the retention of the putative target throughout purification. Replica gels were incubated with ProQ Emerald 300 glycoprotein stain, which fluorescently labels periodate-oxidized glycans while leaving the polypeptide backbone intact. The ProQ Emerald 300-stained gel band corresponding to the 180 kDa HECA-452-reactive protein(s) was excised and digested in-gel with trypsin (FIG. 1). Extracted peptides were then analyzed by nano-flow HPLC interfaced to electrospray ionization MS/MS (FIG. 1). Bioinformatics analysis of the MS data revealed peptide fragment matches for carcinoembryonic antigen (CEA; CD66e) in two separate sample submissions.

Figure 6A:
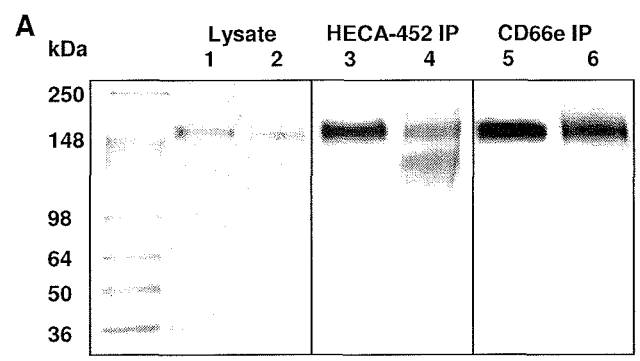
FIGS. 6A-6B provides the Western blot results from CD66e experiments. A: Western blots of whole cell lysate or immunopurified HECA-452-reactive epitopes or immunopurified CD66e from CD44-knockdown LS174T colon carcinoma cells. Anti-CD66de (Col-1) (lanes 1, 3 and 5) or HECA-452 (lanes 2, 4 and 6) mAbs were used to stain Western blots of CD44-knockdown LS174T whole cell lysate (lanes 1 and 2), immunoprecipitated HECA-452-reactive epitopes (lanes 3 and 4), and immunoprecipitated CD66e (lanes 5 and 6) from CD44-knockdown LSI 74T cells. B: Selectin-dependent adhesion to SDS-PAGE resolved and blotted CEA immunoprecipitated from CD44-knockdown LS174T whole cell lysate. CHO-E cells, lymphocytes or CHO-P cells were perfused at the wall shear stress level of 0.5 dyn/cm$^2$ over SDS-PAGE immunoblots of immunopurified CD66e from whole cell lysate of CD44-knockdown LSI 74T cells. In select experiments, CHO-E cells and lymphocytes were pre-treated with an anti-E-selectin or an anti-L-selectin function blocking mAb (20 µg/ml), respectively, before use in blot rolling assays. The saturating concentration of the mAb (20 µg/ml) was maintained in the perfusion assays. Data represent the mean±S.E. of n≥3 experiments.

A series of experiments were performed to confirm the identity of the selectin ligand. Immunoblot analysis using an anti-CD66de mAb, Col-1, revealed the presence of CEA with an apparent molecular mass of 180 kDa in CD44-knockdown LS174T cell lysate, and the lack of CD66d immuno-reactivity at 35 kDa (FIG. 6A, lane 1). CEA is enriched in HECA-452-immunoprecipitated specimens relative to whole cell lysates (FIG. 6A, lane 3). The presence of HECA-452 reactivity on CEA was also disclosed by staining immunopurified CEA with a HECA-452 mAb (FIG. 6A, lanes 5 and 6).

Figure 6B:
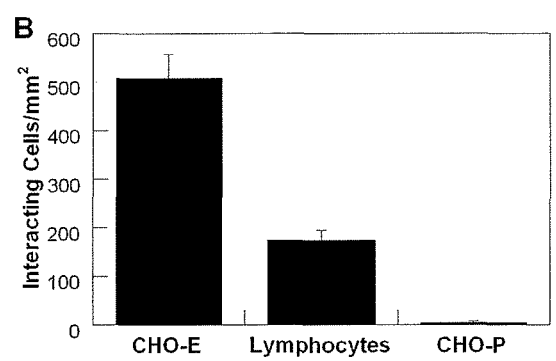

Although previous studies have reported that CEA and CEA-family members such as CD66c (Kuijpers, et al., 118(2) J CELL BIOL. 457-466 (1992)) bind E-selectin under static/no-flow conditions, the capacity of CEA to interact with E-selectin under physiologically relevant flow conditions as well as its potential cross-reactivity with L- and P-selectin have yet to be examined. To address these issues, E-selectin- and P-selectin-transfected CHO cells as well as L-selectin-expressing human peripheral blood lymphocytes were perfused over the SDS-PAGE resolved immunopurified CEA protein band. The data reveals that E- and L-, but not P-, selectin expressing cells bind avidly and extensively to immunopurified CEA from CD44-knockdown colon carcinoma cells (FIG. 6B), suggesting that CEA possesses E- and L-, but not P-, selectin ligand activity. The specificity of these adhesive interactions was assessed by incubating CHO-E cell suspensions or lymphocytes with an anti-E-selectin or an anti-L-selectin function-blocking mAb, respectively (FIG. 6B). Moreover, CHO-E cells or lymphocytes suspended in flow medium containing 5 mM EDTA failed to adhere to any region of the blot (data not shown).

Figure 7A:
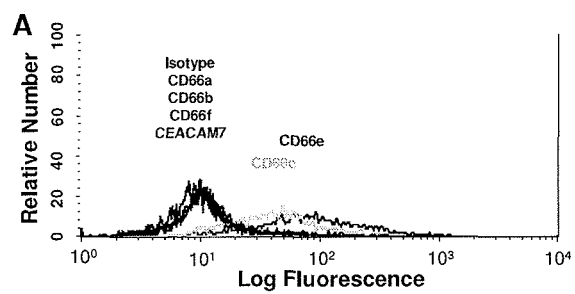
FIGS. 7A-7C presents results from flow-based adhesions assays using CD66e. A: Representative flow cytometric histograms of CEACAM expression by wildtype LS 174T cells. CEACAM expression on colon carcinoma cells was investigated by using primary anti-CD66 mAbs (CD66a, GM8G5; CD66b, 80H3; CD66c, 9A6; CD66de, Col-I; CD66f, BAP3; CEACAM7, BAC2) in conjunction with appropriate PE-conjugated secondary and isotype control antibodies. B: Western blots of whole cell lysate or immunoprecipitated CEA from wildtype LS 1 74T colon carcinoma cells. Anti-CD66de (Col-1) (lanes 1 and 3) or HECA-452 (lanes 2 and 4) mAbs were used to stain Western blots of whole cell lysate (lanes 1 and 2) and immunoprecipitated CEA (lanes 3 and 4) from wildtype LS174T colon carcinoma cells. C: Western blots of whole cell lysate or immunoprecipitated CD66c from wildtype LS174T colon carcinoma cells. Anti-CD66c (B6.2) (lanes 1 and 3) or HECA-452 (lanes 2 and 4) mAbs were used to stain Western blots of whole cell lysate (lanes 1 and 2) and immunoprecipitated CD66c (lanes 3 and 4) from wildtype LS174T cells.
Figure 7B:
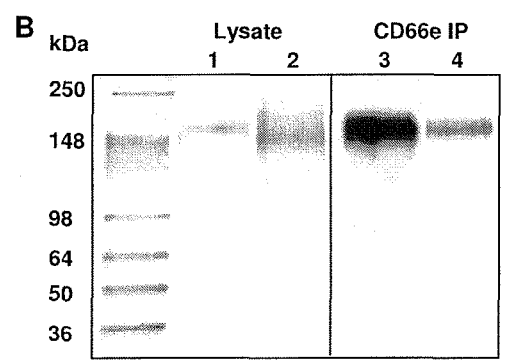
Figure 7C:
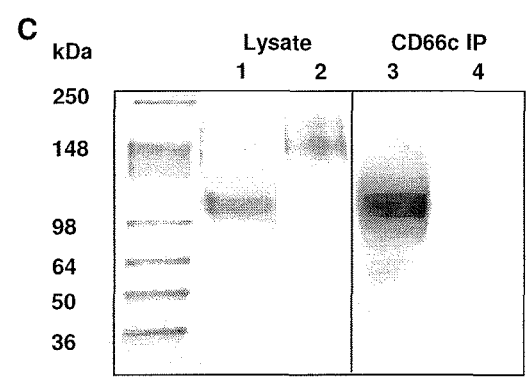

Using mAbs specific for the various members of the CEA family of immunoglobulins (CD66a, b, c, e, f, and CEACAM7) along with indirect single-color immunofluorescence flow cytometry, it was determined that CEA (CD66e) and CD66c, but not CD66a, b, for CEACAM7, are expressed on the surface of wildtype LS 174T colon carcinoma cells (FIG. 3A). Similarly, only CEA and CD66c are present on the surface of CD44-knockdown LS174T cells at levels equivalent to those on wildtype controls (data not shown). The presence of CEA and CD66c in wildtype LS174T cell lysate was confirmed by immunoblot analysis (FIG. 7B, 7C). In accord with our data using CD44-knockdown colon carcinoma cells, CEA is HECA-452 positive with a molecular mass of 180 kDa (FIG. 7B). In contrast, CD66c is HECA-452 negative (FIG. 7C).

Example 5

Figure 9A:
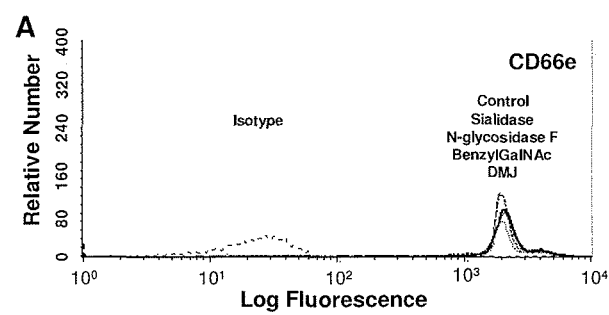
Figure 9B:
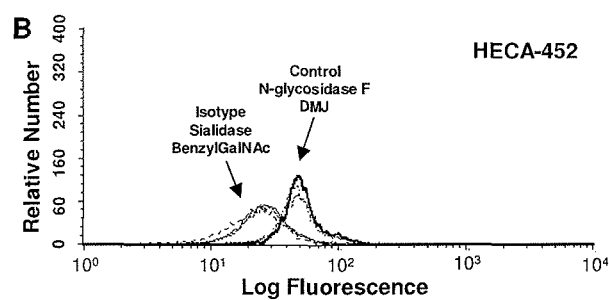
Figure 9C:
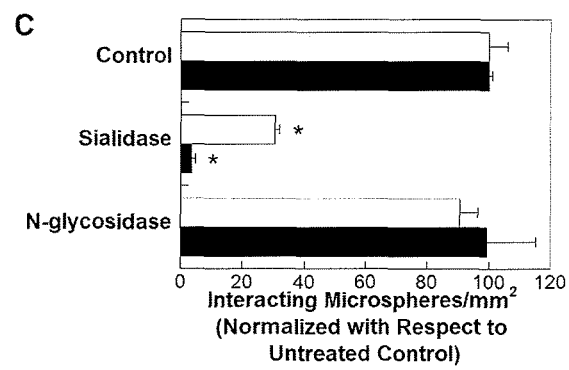

The Selectin Binding Determinants of CD66e are Displayed on Sialofucosylated a-Linked Glycans To characterize the structural linkage-bearing selectin binding determinants on CD66e, CD66e coated microspheres were treated with highly selective enzymes that cleave specific carbohydrate moieties from the CD66e glycoprotein. Treatment of wildtype LS174T CD66e coated microspheres with sialidase eliminated HECA-452 reactivity (FIG. 9B) without affecting the CD66e site density on the bead surface (FIG. 9A). This pharmacological intervention nearly abolished microsphere adhesion to L-selectin and reduced binding to E-selectin by ~70% (FIG. 9C). It is noteworthy that sialidase treatment converted the remaining interactions between CD66e-bearing microspheres and E-selectin from stable rolling to swift tethers.

Figure 9D:
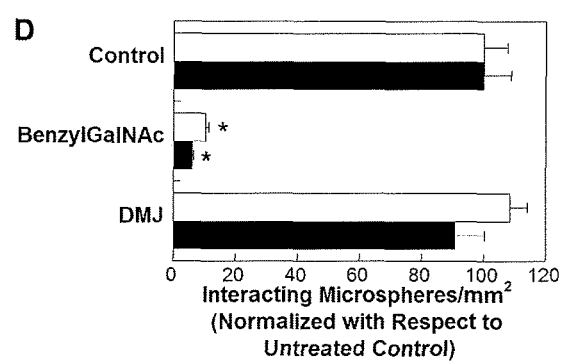

To assess the potential contribution of N-linked glycans to CD66e-selectin interactions, microspheres were coated with wildtype LS174T CD66e immunoprecipitated from N-glycosidase F-treated membrane lysate prior to their perfusion over E- and L-selectin substrates. Alternatively, microspheres were generated using CD66e immunopurified from LS174T cells cultured for 48 h in medium containing deoxymannojirimycin (DMJ) (1 mM) to disrupt N-linked processing. Hanley, et al., 20(2) FASEB J. 20(2), 337-339 (2006); and Napier, et al., 282(6) J. BIOL. CHEM. 3433-3441 (2007). These treatments did not alter the CD66e site density on the bead surface (FIG. 9A) or the HECA-452-reactivity (FIG. 9B), or the extent of bead tethering to E- and L-selectin substrates under flow (FIGS. 9C, 9D).

To determine the potential role of 0-glycans in CD66e-selectin binding, microspheres were prepared using CD66e immunoprecipitated from colon carcinoma cells cultured for 48 h in medium containing 2 mM benzyl-GalNAc to inhibit a-linked glycosylation. Hanley, et al., 20(2) FASEB J. 20(2), 337-339 (2006); and Napier, et al., 282(6) J. BIOL. CHEM. 3433-3441 (2007). Site densities of adsorbed CD66e were verified by flow cytometry to be similar to those of untreated controls (FIG. 9A). However, benzyl-GalNAc treatment eliminated HECA-452 reactive epitopes from LS 174T CD66e (FIG. 9B), suggesting that the majority of sLex displayed on CD66e are O-linked glycans. Moreover, CD66e-coated microspheres from benzyl-GalNAc-treated LS 174 T cells bound minimally to E- and L-selectin in shear flow (FIG. 9D), suggesting that the selectin-binding determinants on CD66e from LS174T colon carcinoma cells are sialofucosylated structures displayed on O-linked glycans.

Example 6

Figures 8A, 8B:
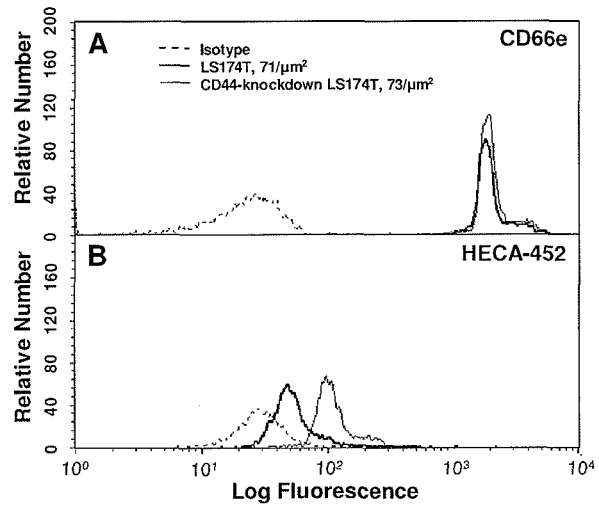
FIGS. 8A-8E show results from CD66e and blot-rolling assays. A and B: Site densities of CD66e (A) and HECA-452-reactive epitopes (B) on polystyrene microspheres coated with CD66e immunopurified from either wildtype (bold line) or CD44-knockdown (thin line) LS174T cells. Microspheres were stained with PE-conjugated anti-CD66 B1.1(A), FITC-conjugated HECA-452 (B), or PE- or FITC-conjugated isotype control antibodies (dashed lines). C: Extent of adhesion of microspheres ($10^6$/ml) coated with CD66e immunopurified from wildtype (black bars) or CD44-knockdown (white bars) LS174T colon carcinoma cells to 10 µg/ml E-, L-, or P-selectin at a wall shear stress level of 1 dyn/cm$^2$ for 2 min. Data represent the mean±S.E.

CEA, but not CD66c, is a Sialofucosylated Selectin Ligand on LS174T Colon Carcinoma Cells A cell-free flow-based adhesion assay (Hanley, et al., 20(2) FASEB J. 20(2), 337-339 (2006); Napier, et al., 282(6) J. BIOL. CHEM. 3433-3441 (2007)) was used to compare the adhesion of microspheres coated with CEA immunopurified from wildtype versus CD44-knockdown LS174T colon carcinoma cells to selectin substrates in shear flow. This technique allows quantitative comparisons of CEA-mediated adhesion to selectin substrates at prescribed CEA and selectin site densities under physiological flow conditions. By coating microspheres with equivalent levels of CEA from wildtype and CD44-knockdown LS 174T cells (FIG. 8A), it was determined that CEA from CD44-knockdown cells is much more densely decorated with HECA-452-reactive epitopes relative to wildtype LS174T CEA (FIG. 8B). Taken together, these data suggest that CEA serves as an alternative glycosylation acceptor on colon carcinoma cells.

Figure 8C:
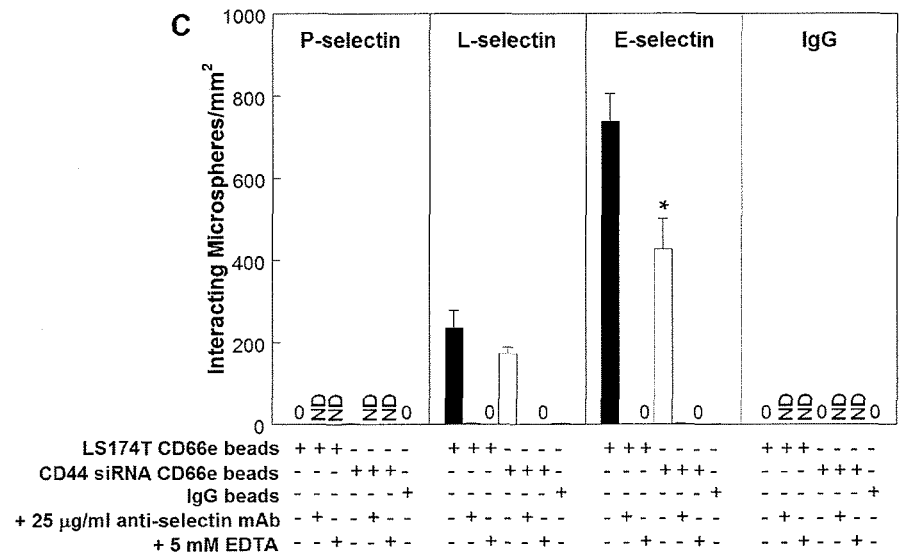
Figure 8D:
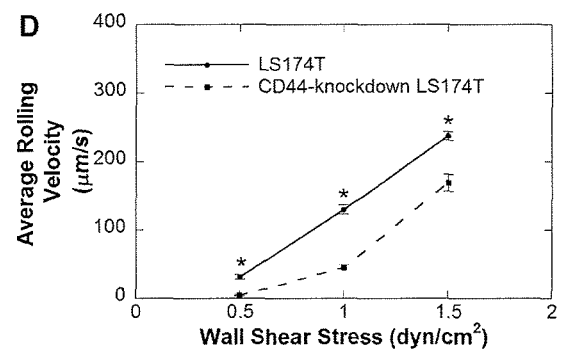
Figure 8E:
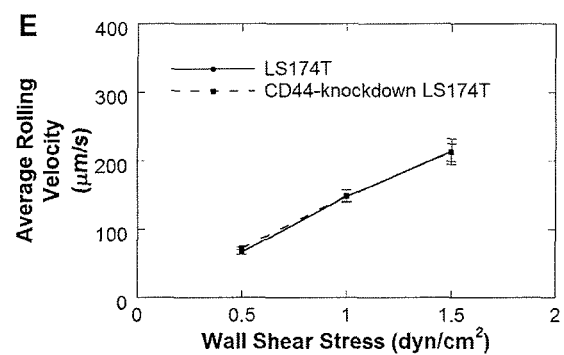

It was hypothesized that the difference in HECA-452 immunoreactivity of CEA in wildtype and CD44-knockdown cells could impact the biophysics of CEA-selectin interactions in shear flow. To test this hypothesis, the CEA-coated microspheres were perfused over purified selectin substrates under prescribed wall shear stress levels. As expected from blot rolling assays, microspheres coated with CEA from either cell type were capable of tethering and rolling over E- and L-, but not P-, selectin substrates, albeit with varying efficiencies (FIG. 8C-E). Most importantly, the extent of tethering of CD44-knockdown LS174T CEA-coated microspheres to E-selectin was lower than that of microspheres decorated with CEA from wildtype LS174T cells (FIG. 8C). This difference is attributed to the slower average rolling velocities of the former microspheres (and thus lower number of beads entering the field of observation (McCarty, et al., 96 BLOOD 1789-1797 (2000))) relative to wildtype LSI 74T CEA-coated beads over E-selectin over a wide range of wall shear stresses varying from 0.5 to 1.5 dyn/cm2 (FIG. 8D). In contrast, no difference was detected in either the extent of tethering (FIG. 8C) or the average rolling velocities (FIG. 8E) of microspheres coated with CEA from either cell type over L-selectin. The specificity of CEA-selectin interactions in these assays was evaluated through the use of nonspecific IgG-coated microspheres and by pre-incubating the selectin-functionalized dishes with the respective function-blocking anti-selectin mAb prior to the perfusion of CEA-coated microspheres. In both cases, no microsphere tethered to selectin substrates during the entire length of the flow experiment (FIG. 8C). As an additional control experiment, CEA-bearing microspheres, perfused over selectin substrates in the presence of 5 mM EDTA in the perfusion buffer, failed to tether to either E- or L-selectin under flow (FIG. 8C).

It was next determined whether CD66c on LS174T cells serves as a selectin ligand. CD66c was immunopurified from the whole cell lysate of wildtype and CD44-knockdown LSI 74T colon carcinoma cells using the anti-CD66c mAb B6.2. Microspheres coated with CD66c from either cell type failed to tether to E-selectin substrates beyond background levels under flow (data not shown). Cumulatively, these data suggest that the HECA-452-negative CD66c (FIG. 7C) does not possess E-selectin-ligand activity in LS174T colon carcinoma cells.

Example 7

Figure 10A:
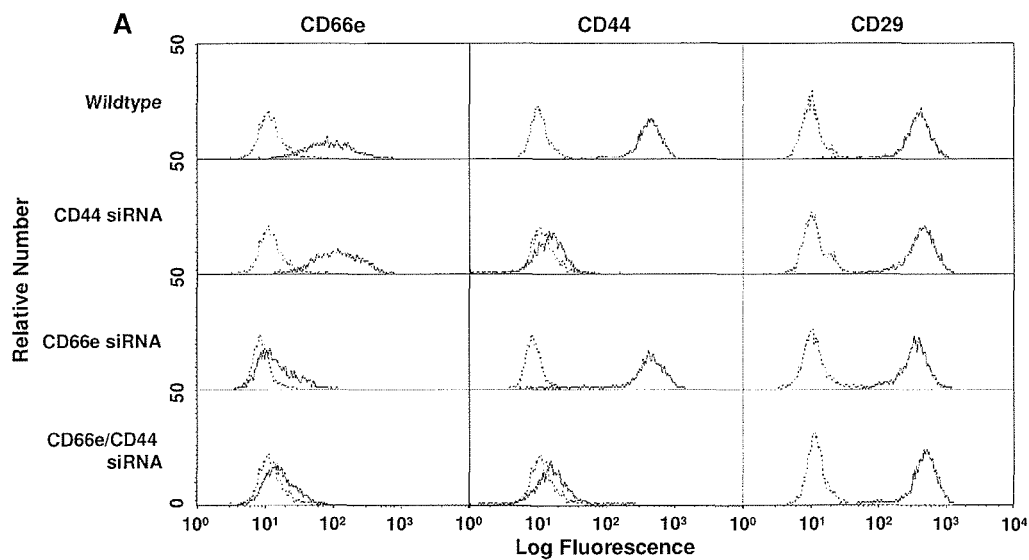

CEA and CD44 Cooperate to Mediate Colon Carcinoma Cell Adhesion to E- and L-Selectin at Elevated Shear Stresses To assess the functional role of CEA in the adhesion of colon carcinoma cells to selectins under flow, stable CEA-knockdown and CEA/CD44-double knockdown LS174T cell lines were generated by transfecting wildtype and CD44-knockdown cells, respectively, with a CEA shRNA plasmid, isolating single cell clones and propagating these clones in puromycin-containing media. As shown in FIG. 10A, this procedure resulted in the generation of CEA-knockdown and CEA/CD44-double knockdown LS174T cells with markedly reduced CEA surface expression (>95% decrease in MFI) relative to wildtype and CD44-knockdown LS174T cells transfected with a control plasmid, as evidenced by flow cytometry using the anti-CD66de mAb Col-I. Evidence for the specificity of this genetic intervention was provided by the flow cytometric analysis of other LS 174T cell surface adhesion molecules such as CD29 (FIG. 10A).

Figure 10B:
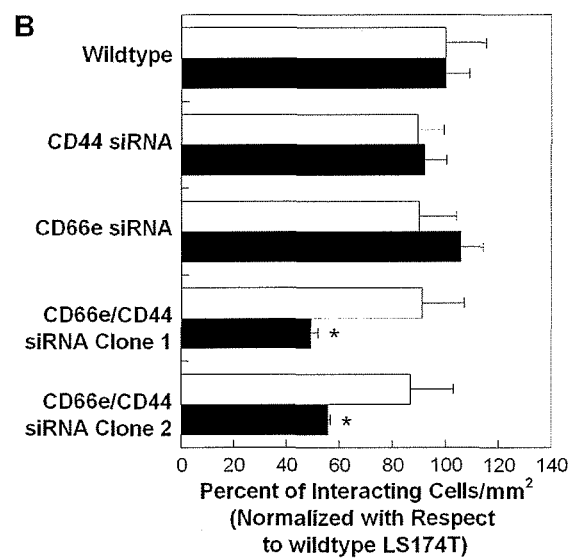
Figure 10C:
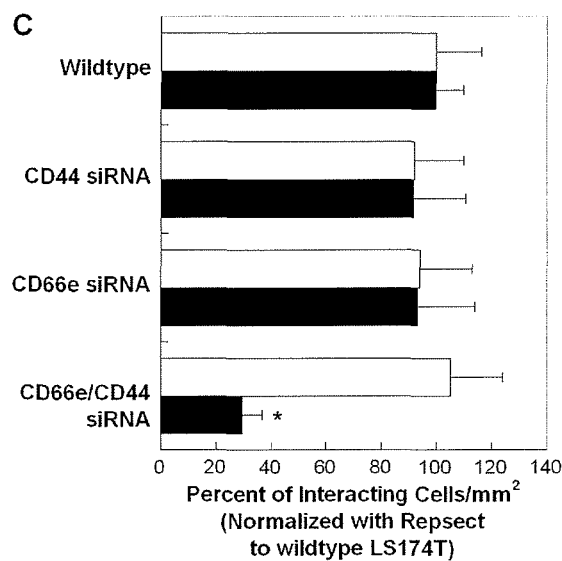
Figure 10D:
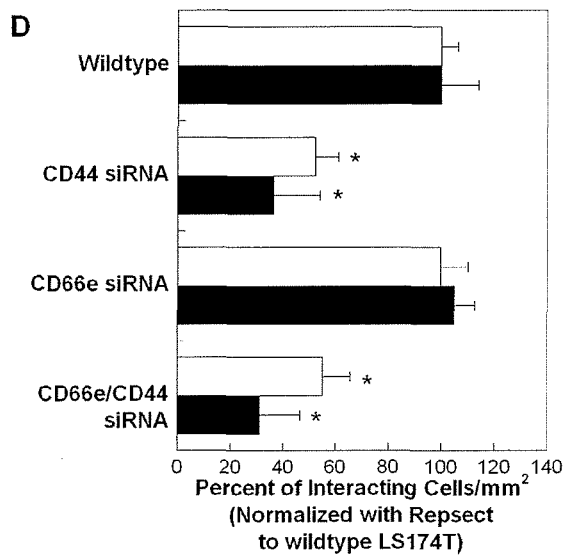

In flow-based adhesion assays, CEA-knockdown LS174T colon carcinoma cells tethered to E-, L-, and P-selectin substrates under flow at levels comparable to those of wildtype controls (FIGS. 10B, 10C, 10D). However, CEA knockdown significantly increased the average rolling velocity of colon carcinoma cells on L-selectin (Table 3), but not on E-selectin (Table 4) or P-selectin (data not shown), relative to wildtype cells. On the other hand, CEA/CD44-double knockdown LSI 74T colon carcinoma cells displayed a markedly reduced capacity to tether and roll on purified E-selectin (50% of control) and L-selectin (70% of control), but not P-selectin, substrates at a wall shear stress of 2.0 dyn/cm$^2$, whereas no difference was observed at 10 dyn/cm$^2$ (FIGS. 10B, 10C, 10D). These results were reproducible using two distinct CEA/CD44-double knockdown cell lines (FIG. 10B). Moreover, CEA/CD44-knockdown LS174T colon carcinoma cells rolled with higher rolling velocities over E-selectin relative to wildtype, CD44-knockdown and CEA-knockdown LS174T cells at 2 dyn/cm$^2$, while no difference was evident at 10 dyn/cm$^2$ (Table 3). Although CEA/CD44-double knockdown rolled faster than wildtype controls on L-selectin, no significant difference was detected between double, CEA- or CD44-knockdown cells. Taken altogether, these data indicate that CEA serves as an auxiliary L-selectin ligand, which is engaged in the stabilization of LS174T cell rolling on L-selectin against fluid shear. Moreover, CEA and CD44 cooperate to mediate colon carcinoma cell adhesion to E- and L-selectin at elevated shear stresses.

TABLE 3

Average rolling velocities (μm/s) of wildtype, CD44-knockdown, CEA-knockdown, CEA/CD44-double knockdown LS174T cells (10$^6$/ml) perfused over a surface coated with 1.5 μg/ml L-selectin at the physiological shear stress levels of 1.0 or 2.0 dyn/cm$^2$.

| | Average Rolling Velocity (μm/s) | |
|---|---|---|
| | 1.0 dyn/cm$^2$ | 2.0 dyn/cm$^2$ |
| Wildtype LS174T | 182 ± 9 | 320 ± 10 |
| CD44-knockdown LS174T | 236 ± 8* | 440 ± 10* |
| CEA-knockdown LS174T | 245 ± 7* | 400 ± 10* |
| CEA/CD44-knockdown LS174T | 238 ± 8* | 440 ± 20* |

Data resent the mean ± S.E.
*$p < 0.05$ with respect to wildtype LS174T cells.

TABLE 4

Average rolling velocities (μm/s) of wildtype, CD44-knockdown, CEA-knockdown, CEA/CD44-double knockdown LS174T cells (10$^6$/ml) perfused over a surface coated with 0.75 μg/ml E-selectin at the physiological shear stress levels of 1.0 or 2.0 dyn/cm$^2$.

| | Average Rolling Velocity (μm/s) | |
|---|---|---|
| | 1.0 dyn/cm$^2$ | 1.0 dyn/cm$^2$ |
| Wildtype LS174T | 5.3 ± 0.3 | 7.2 ± 0.4 |
| CD44-knockdown LS174T | 5.1 ± 0.3 | 6.9 ± 0.5 |
| CEA-knockdown LS174T | 5.2 ± 0.4 | 7.1 ± 0.5 |
| CEA/CD44-knockdown LS174T | 5.2 ± 0.4 | 10 ± *†§ |

Data represent the mean ± S.E.
*$p < 0.05$ with respect to wildtype LS174T cells.
†$p < 0.05$ with respect to CD44-knockdown LS174T cells.
§$p < 0.05$ with respect to CEA-knockdown LS174T cells.

Example 8

Cancer Cell-Sorting to Prescribed Antibody-Coated Microdomains

Utilizing a microfabricated surface to capture antigen-specific cells and triggering their release at later time point could be a valuable research tool for immunology and cancer research. Zhu et al., 64 COLLOIDS SURF. B. BIONTERFACES 260268 (2008). By using a serial combination of μCP and microfluidics, multifunctional surfaces presenting discrete patches of different proteins on an inert poly(ethylene glycol) (PEG)-functionalized background (FIG. 11) were prepared. Ghosh et al., 24 LANGMUIR 8I 34-8142 (2008). This method permitted the entrapment of CD44-expressing LS174T colon cancer cells onto discrete microregions of the anti-CD44-antibody patterned glass substrate from a static adhesion assay, with only weak nonspecific adhesion to the nonactive area. Using this μCP/microfluidic approach, a glass slide was also patterned with anti-PSGL I and anti-CEA monoclonal antibodies (targeting PSGL1 on leukocytes and CEA on colon carcinoma cells, respectively), in discrete microdomains surrounded by inert PEG-functionalized microdomains. Driven by the high affinity antibody-antigen binding, LS174T colon carcinoma cells were effectively sorted from PMNs into prescribed patches under both static and physiological flow conditions (FIG. 12). Using a microfluidic platform, Toner and colleagues were able to capture CTCs onto anti-epithelial cell adhesion molecule (anti-EpCAM)-coated microposts from peripheral blood of cancer patients. Nagrath et al., 450 NATURE 1235-1239 (2007). Novel adhesion molecules that are selectively expressed on the surface of different metastatic tumor cell types (e.g. pancreatic, colon carcinoma, breast carcinoma and neuroblastoma cells) are used in the design of biosensor devices for detecting CTCs in the blood of cancer patients.

Example 9

Iodide-Labelling of Antibodies

The antibodies of the present invention may be labeled with a radioisotope like iodine. Iodide-125 (supplied as NaI) is oxidized to form iodine-125, which attacks tyrosyl and histidyl side chains. The iodinated antibodies are easily detected and quantitated using gamma counters or film.

IODO-GEN (Thomson Fisher Scientific, Inc. (Rockford, Ill.)) is dissolved at 0.5 μg/ml in chloroform. The IODO-GEN solution is dispensed into appropriate tubes (e.g., two 6-mm soda glass or 1.5-ml conical tubes) at 100 μl and 20 μl per tube. The chloroform is allowed to evaporate overnight in a fume hood. Immediately before the iodination, a gel filtration column is prepared to separate the labeled antibody from the iodotyrosine generated during the addition of the IODO-GEN stop buffer. A gel matrix with an exclusion limit of 20,000-50,000 for globular proteins is used with medium-sized beads (100 μm in diameter). The column is prepared with 1 ml of bead volume according to the manufacturer's instructions (swelling, etc.). A convenient column for one-time use is be prepared either in a 1-ml or 2-ml syringe barrel with a glass fiber filter cut to fit the bottom of the barrel, or in a disposable pipet with a portion of the cotton plug or some glass wool pushed to the bottom of the pipet.

To keep the nonspecific binding of the iodinated proteins to a minimum, the column is pre-run with at least 10 column volumes of 1% BSA in PBS with 0.02% sodium azide. The column is then washed with 10 column volumes of PBS with 0.02% sodium azide to remove the BSA. Alternatively, the beads can be swelled in buffer containing BSA, and washed with PBS with 0.02% sodium azide before use.

The column is allowed to run until the buffer level drops to just below the top of the bed resin. The flow of the column is stopped either by using a valve at the bottom of the column or by plugging the end with modeling clay. Immediately before the iodination, 50 μl of IODO-GEN stop buffer is added to a 1.5-ml conical tube. This is the "stop tube" that will be used to terminate the oxidation and capture all of the unincorporated iodine.

Behind appropriate shielding in a fume hood, 50 μl of antibody (0.2-1 mg/ml in 0.5 M sodium phosphate, pH 7.5) is added to an IODO-GEN-coated tube at room temperature.

Other buffers can be used with the antibody, but no reducing agents are included. 500 µCi of Na125I is added to the IODO-GEN tube with the antibody. The pipetting tip is disposed in a container for $^{125}$I solid waste. The tube is incubated for 2 minutes, although longer incubation times can be used, but may increase the chances of oxidative damage.

Using a Pasteur pipet, the contents of the tube are transferred to the 50 µl of IODO-GEN stop buffer prepared above and gently mixed. The pipetting tip is disposed in a container for $^{125}$I solid waste. The reaction mixture is carefully applied in the stop solution to the column prepared above. The pipetting tip is disposed in a container for $^{125}$I solid waste.

The tubes are monitored using a minimonitor to identify the peaks of $^{125}$I-labeled antibody and unincorporated label. The fractions containing the iodinated antibody are pooled. The antibody should come off in approximately the second to fourth fraction, well ahead of the blue xylenecyanol, which should run with the unincorporated label. It is often convenient to dispose of the unincorporated label by leaving it on the column and putting the entire column into the $^{125}$I solid waste.

The labeled antibody may be stored in the column buffer of 1% PBS in BSA with 0.02% sodium azide at 4° C. The antibody is stable, but the radioactive iodine is not, so the antibody is used within 6 weeks of preparation. Up to 90% of the input iodine can be incorporated. This labeling procedure yields specific activities between 1 µCi/µg and 45 µCi/µg. These levels can be adjusted by varying the input iodine and protein concentrations.

See COLD SPRING HARB. PROTOC. (2006). See also Fraker, P. J. and Speck Jr., J. C., 80 BIOCHEM. BIOPHYS. RES. COMMUN. 849-857 (1978) ("Protein and cell membrane iodinations with a sparingly soluble chloroamide, 1,3,4,6-tetra-chloro-3a,6a-diphenylglycoluril").

We claim:

1. A composition comprising at least an antibody to PCLP, an antibody to CEA and an antibody to CD44v, wherein each of the antibodies is conjugated with one of at least three different imaging agents, wherein each of the antibodies is different and binds to a different ligand antigen, and wherein each of the antibodies is conjugated with a different imaging agent.

2. The composition of claim 1, wherein the at least three different imaging agents are radioactive isotopes.

3. The composition of claim 1, wherein one of the at least three different imaging agents is Iodine 131.

4. The composition of claim 1, wherein the at least three antibodies are selected from the group consisting of a polyclonal antibody, a monoclonal antibody, a recombinant antibody, a humanized antibody, a single chain antibody, and a Fab fragment.

5. A method for imaging a cancer cell in a targeted tissue or a biological fluid of a patient comprising:
   a. administering to the targeted tissue or biological fluid the composition of claim 1;
   b. wherein the at least three different antibodies, each conjugated with a different one of the at least three different imaging agents bind to different ligand antigens present on cancer cells to form resultant complexes each resultant complex having a different one of the at least three different imaging agents;
   c. detecting the resultant complexes having the at least three different imaging agents at the targeted tissue or biological fluid; and
   c. determining the presence of a cancer cell at the targeted tissue or the biological fluid based on the detection of the resultant complexes.

6. The method of claim 5, wherein the at least three different imaging agents are selected from the group consisting of a radiologic contrast agent, diatrizoic acid sodium salt dihydrate, an iodine-containing agent, a barium-containing agent, a fluorescent imaging agent, Lissamine Rhodamine PE, a stain, a dye, a radioisotope, a metal, a ferromagnetic compound, a paramagnetic compound, gadolinium, a superparamagnetic compound, iron oxide, a diamagnetic compound, and barium sulfate.

7. The method of claim 5, wherein the at least three different antibodies are selected from the group consisting of a polyclonal antibody, a monoclonal antibody, a recombinant antibody, a humanized antibody, a single chain antibody, and a Fab fragment.

8. The method of claim 5, wherein the detecting step comprises using an imaging device.

* * * * *